United States Patent [19]
Hirai et al.

[11] Patent Number: 5,554,581
[45] Date of Patent: Sep. 10, 1996

[54] TETRAHYDROPHTHALAMIDE DERIVATIVE, INTERMEDIATE FOR PRODUCING THE SAME, PRODUCTION OF BOTH, AND HERBICIDE CONTAINING THE SAME AS ACTIVE INGREDIENT

[75] Inventors: Kenji Hirai; Tomoko Matsukawa; Tomoyuki Yano; Emiko Ejiri; Kiyomi Aizawa; Koichi Shikakura, all of Kanagawa; Tomoko Yoshii, Shizuoka; Sadayuki Ugai, Shizuoka; Osamu Yamada, Shizuoka; Shigeki Kishi, Shizuoka, all of Japan

[73] Assignees: Sagami Chemical Research Center; Kaken Pharmaceutical Co., Ltd., both of Japan

[21] Appl. No.: 450,344

[22] Filed: May 25, 1995

Related U.S. Application Data

[62] Division of Ser. No. 302,881, filed as PCT/JP93/00360, Mar. 25, 1993, Pat. No. 5,506,190.

[30] Foreign Application Priority Data

Mar. 25, 1992 [JP] Japan ........................................ 4-97462
Jan. 28, 1993 [JP] Japan ........................................ 5-31132

[51] Int. Cl.$^6$ ........................... A01N 43/12; C07D 307/87
[52] U.S. Cl. ........................ 504/298; 504/220; 504/224; 504/235; 504/249; 504/266; 504/287; 540/607; 544/176; 544/391; 546/226; 548/200; 548/539; 549/303; 549/466; 564/191
[58] Field of Search .................................. 504/299, 298; 549/466, 303

[56] References Cited

U.S. PATENT DOCUMENTS

| | | | |
|---|---|---|---|
| 3,990,880 | 11/1976 | Mumford | 504/298 |
| 4,328,367 | 5/1982 | Nagase | 564/155 |
| 5,180,587 | 1/1993 | Moore | 424/408 |
| 5,205,853 | 4/1993 | Wolf et al. | 504/247 |

FOREIGN PATENT DOCUMENTS

| | | |
|---|---|---|
| 2409983 | 6/1979 | France . |
| 54-76557 | 6/1979 | Japan . |
| 55-159949 | 12/1980 | Japan . |
| 54-65384 | 12/1980 | Japan . |
| 58-216181 | 12/1983 | Japan . |
| 59-51250 | 3/1984 | Japan . |

*Primary Examiner*—Shailendra Kumar
*Attorney, Agent, or Firm*—Nixon & Vanderhye

[57] ABSTRACT

The present invention relates to 3,4,5,6-tetrahydrophthalamide derivatives and 3,4,5,6-tetrahydroisophthalimide derivatives having excellent effects as effective active ingredients of herbicides, and processes for preparing the same, and provides the compounds having a more efficient herbicidal activity, and efficient and industrial processes for the preparation thereof.

More specifically, the tetrahydrophthalimide derivative obtained by reacting a halogen-substituted 5-cycloalkyloxyaniline derivative with a 3,4,5,6-tetrahydrophthalic anhydride, or the tetrahydroisophthalimide derivative of the present invention is reacted with various types of amines to prepare a tetrahydrophthalamide derivative represented by the general formula (I):

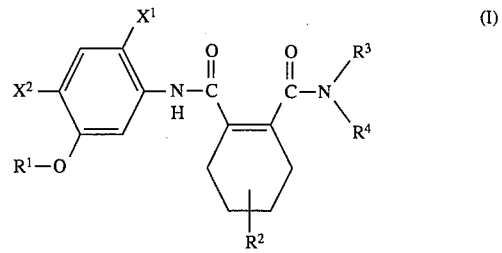

These tetrahydrophthalamide derivatives and the tetrahydroisophthalimide derivatives exhibit excellent herbicidal activities in the soil treatment in the paddy field and field and the stem-foliar treatment. The tetrahydroisophthalimide derivatives are also useful as intermediates for the preparation of the tetrahydrophthalamide derivatives, etc.

4 Claims, No Drawings

5,554,581

1

TETRAHYDROPHTHALAMIDE DERIVATIVE, INTERMEDIATE FOR PRODUCING THE SAME, PRODUCTION OF BOTH, AND HERBICIDE CONTAINING THE SAME AS ACTIVE INGREDIENT

This is a division of application Ser. No. 08/302,881, filed Sept. 19, 1994, now U.S. Pat. No. 5,506,190; which is a 371 of PCT/JP/93/00360.

TECHNICAL FIELD

In recent years, chemical agricultural agents have been essential materials for modern agriculture, and, as social demands for these chemical agricultural agents including herbicides, agents having low toxicity and residue and high selectivity to crops are desired. The present invention is to provide novel herbicides which meet the above-described social demands.

More specifically, the present invention relates to a 3,4,5,6-tetrahydrophthalamide derivative represented by the general formula (I):

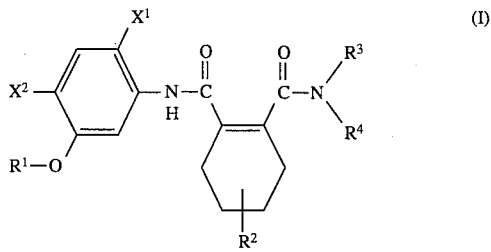

wherein $X^1$ represents a halogen atom, $X^2$ represents a hydrogen atom or a halogen atom, $R^1$ represents a cycloalkyl group having from 3 to 8 carbon atoms which may be substituted, $R^2$ represents a hydrogen atom, a chlorine atom or a methyl group, $R^3$ and $R^4$ each independently represents a hydrogen atom, an alkyl group having from 1 to 12 carbon atoms, a cycloalkyl group having from 3 to 9 carbon atoms, an aryl group having from 6 to 10 carbon atoms, an alkenyl group having from 3 to 5 carbon atoms or an alkynyl group having from 3 to 5 carbon atoms, or $R^3$ and $R^4$ may form, together with the nitrogen atom to which they are attached, a substituted or unsubstituted alicyclic heterocyclic ring; a process for preparing the same; and a herbicide containing the same as an active ingredient.

Further, the present invention relates to a 3,4,5,6-tetrahydroisophthalimide derivative represented by the general formula (V):

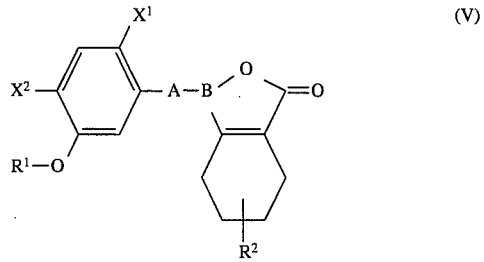

wherein $X^1$ represents a halogen atom, $X^2$ represents a hydrogen atom or a halogen atom, $R^1$ represents a cycloakyl group having from 3 to 8 carbon atoms which may be substituted, A—B represents NH—C(OH) or N=C, and $R^2$ represents a hydrogen atom, a chlorine atom or a methyl group; a process for preparing the same; and a herbicide containing the same as an active ingredient.

2

Also, the 3,4,5,6-tetrahydroisophthalimide derivatives represented by the general formula (V) per se are useful as active ingredients of the herbicide, and also, for example, 3,4,5,6-tetrahydrophthalimideohydroxy derivatives represented by the general formula (V) wherein A—B represents NH—C(OH) can be easily converted by dehydration reaction under heating into the 3,4,5,6-tetrahydrophthalimide derivatives represented by the general formula (II) which are useful as active ingredients for the herbicides disclosed in Japanese Patent Publication (Kokai) No. 4-164067. (Refer to Reference Example 19 below.)

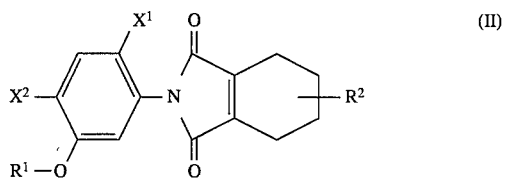

Furthermore, the 3,4,5,6-tetrahydroisophthalimide derivatives represented by the general formula (IV) can be easily converted by reacting with various amines into the 3,4,5,6-tetrahydrophthalamide derivatives represented by the general formula (I) which are the compounds of the present invention and are useful as active ingredients as herbicides.

TECHNICAL BACKGROUND

Hithertofore, as 3,4,5,6-tetrahydrophthalimide derivatives having an herbicidal activity, for example, Japanese Patent Publication (Kokai) Nos. 54-154737, 55-157546 (Japanese Patent Publication No. 63-13981), 59-51250, 60-252457, 61-43160, or U.S. Pat. No. 4,613,675 have been known, but the compounds having a cycloalkyloxy group at the 5-position of the phenyl ring on the nitrogen atom thereof have not been known.

Also, it is conventionally known that the 3,4,5,6-tetrahydrophthalamic derivatives having a carboxylic acid residual group and an amido group which are synthesized by reacting an aniline derivative with 3,4,5,6-tetrahydrophthalic anhydride (for example, the compounds disclosed in Japanese Patent Publication (Kokai) Nos. 48-44425, 54-125640 and 59-67255) exhibit a herbicidal activity, but the 3,4,5,6-tetrahydroisophthalimide hydroxy derivatives represented by the structure of the general formula (V') having a cycloalkyloxy group at the 5-position of the phenyl ring on the nitrogen atom thereof have not been known.

Further, as 3,4,5,6-tetrahydroisophthalimide derivatives, for example, the-compounds disclosed in Japanese Patent Publication (Kokai) No. 53-23962, Japanese Patent Publication No. 3-69907, Japanese Patent Publication No. 4-7347, and U.S. Pat. No. 3,990,880 have been known, but the compounds having a cycloalkyloxy group at the 5-position of the phenyl ring on the nitrogen atom thereof have not been known.

Development of excellent herbicides is required for protecting important crops, for example, rice, soybean, corn, wheat or cotton or beat from weeds, and, further, increasing the productivity of these crops, and contributes to the labor-saving of the agricultural works and hence to the stabilization of the food economy. For such herbicides, development of agents having the following conditions is required.

That is, from the viewpoint of effects, agents having a broad herbicidal spectrum and at the same time a high safety to crops, and also having a high activity to perennial weeds which are difficult to remove are desirable, and, from the viewpoint of labor-saving of works, agents which are effective with a less number of treating times with the agent, and the effect thereof lasts for an appropriate period of time are desirable.

The conventionally known 3,4,5,6-tetrahydrophthalamide derivatives or 3,4,5,6-tetrahydroisophthalimide derivatives per se exhibits good herbicidal effects, but it cannot be said that these derivatives necessarily satisfy the desirable requirements. Further, the above-described known compounds exhibit markedly different strength in the herbicidal activity or selectivity to crops by slight difference in the structure thereof (for example, the type and position of substituents), and, therefore, it is difficult to predict herbicidal activities and selectivities of new compounds merely from the similarity in the chemical structure.

The present invention provides compounds which exhibit an excellent herbicidal activity in the treatment at a low amount and a high safety, and which are further useful as active ingredients of herbicides having an excellent selectivity to the crops.

As a result of extensive studies from the above viewpoints, the present inventors found that the 3,4,5,6 -tetrahydrophthalaimide derivatives in which a cycloalkyloxy group as a substituent has been introduced into the 5-position of the phenyl ring, represented by the general formula (I):

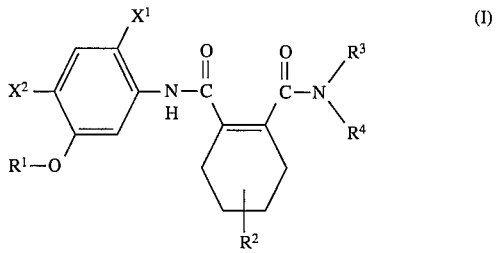

(I)

wherein $X^1$, $X^2$, $R^1$, $R^2$, $R^3$ and $R^4$ have the same meanings as above, and the 3,4,5,6-tetrahydroisophthalimide derivatives in which a cycloalkyloxy group as a substituent has been introduced at the 5-position of the phenyl ring, represented by the general formula (V):

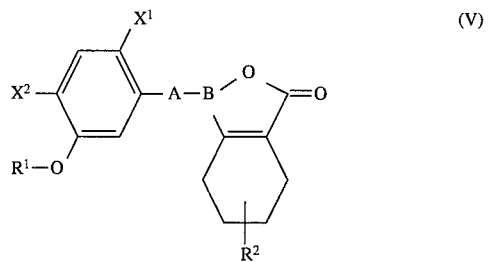

(V)

wherein $X^1$, $X^2$, $R^1$ and $R^2$ have the same meanings as above, have a high herbicidal activity against weeds by the treatment at a low dose and, also, a markedly reduced detrimental effect by the agent on main crops.

The compounds of the present invention exhibit markedly excellent herbicidal activities in the treatment at a low dose in the stem-foliar treatment and the soil treatment in the field on various troublesome weeds, for example, broad leaf weeds such as *Chenopodium album, Amaranthus viridis, Abutilon theophrasti, Stellaria media, Persicaria longiseta* and *Ambrosia elatior,* and grass weeds such as *Echinochloa crus-galli, Setaria viridis, Digitalia ciliaris, Eleusine indica* and *Alopecurus aequalis,* but do not exhibit any troublesome detrimental effect by the agent on main crops, e.g., broad leaf crops such as soybean, cotton and beat, grass crops such as corn and wheat.

Also, the compounds of the present invention exhibit markedly excellent herbicidal activities in the treatment at a low dose on various troublesome weeds in the paddy field, for example, grass weeds such as *Echinochloa oryzicola* and *Echinochloa crus-galli,* broad leaf weeds such as *Lindernia pyxidaria, Rotala indica, Callitriche fallax* and *Monochoria vaginalis,* Cyperus weeds such as *Scirpus juncoides, Eleocharis acicularis, Cyperus difformis, Cyperus serotinus* and *Eleocharis kuroguwai,* and *Sagittaria pygmaea,* whereas these compounds exhibit only very slight detrimental effects by the agent on the transplanted rice plants in the paddy field.

Such a high selectivity of the compounds of the present invention can not be totally expected from conventional 3,4,5,6-tetrahydrophthalamide derivatives, and this characteristic is apparently brought about by introducing a cycloalkyloxy group into the 5-position of the phenyl ring thereof.

In the compounds (I) and (V) of the present invention, examples of the halogen atoms represented by $X^1$ and $X^2$ include a fluorine atom, a chlorine atom and a bromine atom.

Examples of the cycloalkyl group represented by $R^1$ include a cyclopropyl group, a cyclopentyl group, a cyclohexyl group, and a cyclooctyl group, and these groups may be substituted with a lower alkyl group having from 1 to 4 carbon atoms such as a methyl group, an ethyl group and an isopropyl group, or a halogen atom such as a fluorine atom and a chlorine atom.

In the compounds (I) of the present invention, the alkyl group represented by $R^3$ and $R^4$ may be a straight chain or a branched chain and further may have an alicyclic structure on the chain, and examples thereof include a methyl group, an ethyl group, a propyl group, an isopropyl group, a butyl group, an isobutyl group, a sec-butyl group, a tert-butyl group, a pentyl group, a neopentyl group, an isopentyl group, a tert-pentyl group, a 1,2-dimethylpropyl group, a 1-methylbutyl group, a hexyl group, an isohexyl group, a heptyl group, a 1-ethylhexyl group, an octyl group, a decyl group, an undecyl group, a dodecyl group, a cyclopropylmethyl group, a cyclohexylmethyl group, a cyclohexenylmethyl group, a 1-adamantylmethyl group and a myrtanyl group.

These alkyl groups may be substituted with one or more of a halogen atom, a lower alkoxy group, a hydroxy group, a carboxyl group, a lower alkyloxycarbonyl group, a substituted amino group and a cyano group, and examples of these substituted alkyl groups include a 2-chloroethyl group, a 2-bromoethyl group, a 3-fluoropropyl group, a 3-bromopropyl group, a 3,3,3-trifluoropropyl group, a 2 -hydroxyethyl group, a 1-hydroxymethyl-2-methylpropyl group, a 1-hydroxymethyl-2-methylbutyl group, a 1-hydroxymethyl-3 -methylbutyl group, a 1,1-di(hydroxymethyl)ethyl group, a 1-hydroxymethyl-1-methylethyl group, a 1,5-dimethyl-5 -hydroxyhexyl group, a 2-(2-hydroxyethoxy)ethyl group, a 2-methoxyethyl group, a 3-methoxypropyl group, a 1 -methoxy-1-methylpropyl group, a 3-ethoxypropyl group, a 3-isopropoxypropyl group, a 3-propoxypropyl group, a 3 -butoxypropyl group, a methoxycarbonylmethyl group, a 1 -(methoxycarbonyl)ethyl group, a 1-(methoxycarbonyl)propyl group, a 2-methoxycarbonyl-2-methylpropyl group, a 1 -methoxycarbonyl-3-methylbutyl group, a 1-methoxycarbonyl- 2,2-dimethylpropyl group, an ethoxycarbonylmethyl group, a 2-ethoxycarbonyl-2-methylpropyl group, a 1-carboxyethyl group, a 1-carboxypropyl group, a 2-carboxy-2-methylpropyl group, a 1-carboxy-3-methylbutyl group, a 2-(memthoxycarbonyl)ethyl group, a 2-carboxyethyl group, a 6 -carboxyhexyl group, a 4-carboxycyclohexylmethyl group, a 3-dimethylaminopropyl group, a 1-methyl-4-diethylaminobutyl group, a 1-ethoxycarbonyl-4-piperidyl group, and a cyanoethyl group.

Also, the above-described alkyl groups may be substituted with an aromatic group or an alicyclic heterocyclic group which may be substituted with one or more of a halogen atom, a lower alkyl group, a lower alkoxy group, a hydroxy group, a carboxyl group, a lower alkyloxycarbonyl group, a nitro group and a cyano group.

Specific examples of these substituted alkyl groups include a benzyl group, a chlorobenzyl group, a 3-chlorobenzyl group, a 4-chlorobenzyl group, a 4-t-butylbenzyl group, a 4-methylbenzyl group, a 4-methoxybenzyl group, a 1-phenylethyl group, an R-(+)-1-phenylethyl group, an S-(–)-1-phenylethyl group, a 1-(4-chlorophenyl)ethyl group, a 1-(4-methoxyphenyl)ethyl group, a 2-phenylethyl group, a 2-(3,4-dimethoxyphenyl)ethyl group, a 1-methyl-1-phenylethyl group, a 1-methyl-1-(3-chlorophenyl)ethyl group, a 1-methyl-1-(3-fluorophenyl)ethyl group, a 1-methyl-1-(3-trifluoromethylphenyl)ethyl group, a 1-methyl-1-(4-methylphenyl)ethyl group, a 1-methyl-2-(2-hydroxyphenyl)ethyl group, a 1-methyl-1-(4-chlorophenyl)ethyl group, a 1-methyl-1-(4-fluorophenyl)ethyl group, a 1-methyl-1-(4-bromophenyl)ethyl group, a 1-methyl-1-phenylpropyl group, a 1-methyl-1-(4-chlorophenyl)propyl group, a 1-methyl-1-(4-methoxyphenyl)ethyl group, a 1-methyl-1-(2,4-dichlorophenyl)ethyl group, a 1-(1-naphthyl)ethyl group, a 1-(2-naphthyl)ethyl group, a (2-naphthyl)methyl group, a 2-pyridylmethyl group, a 2-(2-pyridyl)ethyl group, a 2-picolyl group, a 3-picolyl group, a furfuryl group, a tetrahydrofurfuryl group, a 2-thiophenemethyl group, a 2-(1-methyl-2-pyrrol-2-yl)ethyl group, a 2-(1-methylpyrrolidinyl)ethyl group, a 2-(1-pyrrolidinyl)ethyl group, a 2-morpholinoethyl group, a 3-morpholinopropyl group and a 2-piperidinoethyl group.

Examples of the cycloalkyl group represented by $R^3$ and $R^4$ include a cyclopropyl group, a cyclopentyl group, a cyclohexyl group, a cyclooctyl group, a 2-norbornyl group, a norbornen-2-yl group, a 2-bicyclo[3.2.1]octyl group, a 3-noradamantyl group, a 1-adamantyl group and a 2-adamantyl group. These cycloalkyl groups may be substituted with a lower alkyl group, a halogen atom, a hydroxy group, or an amino group, etc., and examples thereof include a 2-methylcyclohexyl group, a 2-aminocyclohexyl group, a 2-hydroxycyclohexyl group, and a 1-(hydroxymethyl)cyclopentyl group.

Examples of the alkenyl group or the alkynyl group represented by $R^3$ and $R^4$ include an allyl group, a methallyl group, a crotyl group, a purenyl group, a propargyl group and a 1-butyn-3-yl group. Also, these alkenyl groups and alkynyl groups may be substituted with a halogen atom such as a fluorine atom or a chlorine atom.

Examples of the aryl group represented by $R^3$ and $R^4$ includes a phenyl group and a naphthyl group. These aryl groups may be substituted with a lower alkyl group, a halogen atom, a lower alkoxy group, a hydroxymethyl group, a trifluoromethyl group, a carboxy group, a cyano group, etc., and examples thereof include a 2-chlorophenyl group, a 2-fluorophenyl group, a 4-chlorophenyl group, a 4-fluorophenyl group, a 4-tert-butylphenyl group, a 4-methylphenyl group, a 4-isopropylphenyl group, a 2-hydroxymethylphenyl group, a 3-hydroxymethylphenyl group, a 4-hydroxymethylphenyl group, a 3-chloro-4-cyanochlorophenyl group, a 4-carboxy-3-chlorophenyl group, a 5-chloro-2-trifluoromethylphenyl group, a 4-chloro-2-trifluoromethylphenyl group, a 2-chloro-5-trifluoromethylphenyl group and a 4-chloro-3-trifluoromethylphenyl group.

Examples of substituted or unsubstituted alicyclic heterocyclic ring formed with the nitrogen atom to which $R^3$ and $R^4$ are bonded include those illustrated in terms of the amines represented by the corresponding general formula (III), as well as aziridine, azetidine, piperidine, pyrrolidine, piperazine, morpholine, thiomorpholine, 2-pyrroline, 3-pyrroline, 1,2,3,6-tetrahydropyridine, pyrazolidine, pyrazoline, 1,2-piperazine, 1,3-piperazine, thiazolidine, oxazolidine, isooxazolidine, tetrahydropyridazine and hexahydropyridazine.

These alicyclic heterocyclic rings may be substituted with a lower alkyl group, a phenyl group, a substituted phenyl group, a benzyl group, an acetyl group, a hydroxy group, a hydroxymethyl group, a carboxyl group, an acetamido group, a lower alkyloxycarbonyl group, etc., and examples thereof include, as specifically illustrated in terms of the amines (III), methylaziridine, 2,5-dimethylpyrrolidine, 3-hydroxypyrrolidine, proline, perhydroindole, 3-acetamidopyrrolidine, 4-carboxythiazolidine, 3,5-dimethylpiperidine, 3,3-dimethylpiperidine, isonipecotic acid, 3-hydroxypiperidine, 2,6-dimethylpiperidine, ethyl 2-pipecolate, ethyl 3-nipecotate, ethyl isonipecotate, 4-benzylpiperidine, 1-phenylpiperazine, 1-(2-methylphenyl)piperazine, 1-methylpiperazine, 1-benzylpiperazine, 1-(2-methoxyphenyl)piperazine, 1-(2-chlorophenyl)piperazine, 1-(2-fluorophenyl)piperazine, 1-(4-fluorophenyl)piperazine and 1-ethoxycarbonylpiperazine.

The amines (III) having a substituent as illustrated above are commercially available compounds or compounds which can be easily synthesized by a conventional process.

Processes for preparing the compounds of the present invention, 3,4,5,6-tetrahydrophthalamide derivatives (I), and the compounds of the present invention, 3,4,5,6-tetrahydroisophthalimide derivatives (V) which are also starting materials therefor are described below.

The compounds of the present invention represented by the general formula (I) can be prepared by reacting a 3,4,5,6-tetrahydrophthalimide derivative represented by the general formula (II):

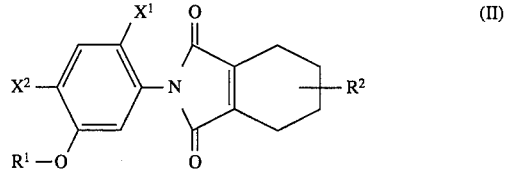

wherein $X^1$, $X^2$, $R^1$ and $R^2$ have the same meanings as defined above, with an amine represented by the general formula (III):

wherein $R^3$ and $R^4$ have the same meanings as defined above. In this reaction, the compounds of the present invention (I) can be obtained in good yields by reacting generally 0.5 molar equivalent or more, preferably from 0.9 to 1.5 molar equivalent of the amine (III) to the 3,4,5,6-tetrahydrophthalimide derivative (II).

The reaction can be conducted in a solvent, for example, a halogenated hydrocarbon solvent such as methylene chloride, chloroform, carbon tetrachloride and chlorobenzene, a hydrocarbon solvent such as benzene, toluene, xylene, hexane, octane and cyclohexane, an ether solvent such as diethyl ether, dioxane, tetrahydrofuran and dimethoxyethane, a ketone solvent such as acetone and methyl ethyl ketone, an inert solvent such as acetonitrile, ethyl acetate and dimethylformamide, or a mixed solvent thereof.

The reaction temperature is generally selected from a range of from 0° C. to 100° C. The reaction time varies depending upon the type of reaction materials, and generally the reaction is completed within 5 minutes to 24 hours.

Also, the reaction can be carried out by adding a catalyst for the purpose of promoting the reaction. The catalyst which is generally used includes a basic compound such as triethylamine, N-methylmorpholine, pyridine, N,N-dimethylaniline, potassium carbonate and sodium carbonate.

The tetrahydrophthalimide derivatives represented by the above general formula (II) which are starting materials for the preparation of the compounds of the present invention can be easily prepared according to the process described in Japanese Patent Publication (Kokai) No. 4-164067. More specifically, these compounds can be prepared by reacting an aniline derivative represented by the general formula (VI):

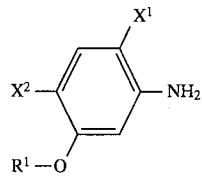
(VI)

wherein $X^1$, $X^2$ and $R^1$ have the same meanings as defined above, with a 3,4,5,6-tetrahydrophthalic anhydride represented by the general formula (VII):

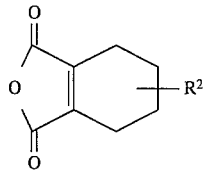
(VII)

wherein $R^2$ has the same meaning as defined above, in an organic solvent, preferably while heating at 50° to 120° C. (refer to Reference Example 17 and 18 described hereinafter).

Examples of the 3,4,5,6-tetrahydrophthalimide derivatives represented by the above-described general formula (II) which can be prepared as described above and which are starting materials for the preparation of the compounds of the present invention include N-(2-fluoro- 4-chloro-5-cyclopropyloxyphenyl)-3,4,5,6-tetrahydrophthalimide, N-(2-fluoro-4-chloro-5-cyclopentyloxyphenyl)- 3,4,5,6-tetrahydrophthalimide, N-{2-fluoro-4-chloro-5-(2-methylcyclopentyl)oxyphenyl}-3,4,5,6-tetrahydrophthalimide, N-{2-fluoro-4-chloro-5-(3-methylcyclopentyl)oxyphenyl)- 3,4,5,6-tetrahydrophthalimide, N-(2-fluoro-4-chloro-5 -cyclohexyloxyphenyl)-3,4,5,6-tetrahydrophthalimide, N-{2-fluoro-4-chloro-5-(2-chlorocyclohexyl)oxyphenyl}- 3,4,5,6-tetrahydrophthalimide, N-(2-fluoro-4-chloro-5 -cyclooctyloxyphenyl)-3,4,5,6-tetrahydrophthalimide, N-(2-fluoro-4-bromo-5-cyclopropyloxyphenyl)-3,4,5,6 -tetrahydrophthalimide, N-(2-fluoro-4-bromo-5-cyclopentyloxyphenyl)- 3,4,5,6-tetrahydrophthalimide, N-{2-fluoro-4-bromo-5-(2-methylcyclopentyl)oxyphenyl}-3,4,5,6 -tetrahydrophthalimide, N-{2-fluoro-4-bromo-5-(3 -methylcyclopentyl)oxyphenyl}-3,4,5,6-tetrahydrophthalimide, N-(2-fluoro-4-bromo-5-cyclohexyloxyphenyl)-3,4,5,6 -tetrahydrophthalimide, N-(2,4-dichloro-5-cyclopropyloxyphenyl)- 3,4,5,6-tetrahydrophthalimide, N-(2,4-dichloro-5-cyclopentyloxyphenyl)- 3,4,5,6-tetrahydrophthalimide, N-{2,4-dichloro-5-(2-methylcyclopentyl)oxyphenyl}-3,4, 5,6 -tetrahydrophthalimide, N-{2,4-dichloro-5-(3-methylcyclopentyl)oxyphenyl}-3,4,5,6-tetrahydrophthalimide, N-(2, 4-dichloro-5-cyclohexyloxyphenyl)-3,4,5,6-tetrahydrophthalimide, N-(2,4-dichloro-5-cyclooctyloxyphenyl)- 3,4,5,6-tetrahydrophthalimide, N-(2-fluoro-4-chloro-5 -cyclopentyloxyphenyl)-3-methyl-3,4,5, 6-tetrahydrophthalimide, N-(2-fluoro-4-chloro-5-cyclopentyloxyphenyl)- 4-methyl-3,4,5,6-tetrahydrophthalimide, N-(2-fluoro-4-chloro-5-cyclopentyloxyphenyl)-4-chloro-3,4,5,6-tetrahydrophthalimide, N-{2-fluoro-4-chloro-5-(3-methylcyclopentyl)oxyphenyl}-3-methyl-3,4,5,6-tetrahydrophthalimide, N-{2-fluoro-4-chloro-5-(3-methylcyclopentyl)oxyphenyl}-4 -methyl-3,4,5,6-tetrahydrophthalimide, N-(2-fluoro-5-cyclopentyloxyphenyl)- 3,4,5,6-tetrahydrophthalimide, N-{2-fluoro- 5-(2-methylcyclopentyl)oxyphenyl}-3,4,5,6-tetrahydrophthalimide, N-{2-fluoro-5-(3-methylcyclopentyl)oxyphenyl- 3,4,5,6-tetrahydrophthalimide, and N-(2-fluoro-5-cyclohexyloxyphenyl)-4-methyl-3,4,5,6 -tetrahydrophthalimide.

Also, the compounds of the present invention represented by the general formula (I) can be prepared by reacting a 3,4,5,6-tetrahydroisophthalimide derivative which is a compound of the present invention represented by the general formula (IV):

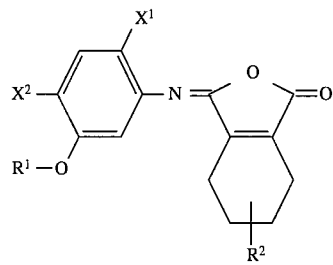
(IV)

wherein $X^1$, $X^2$, $R^1$ and $R^2$ have the same meanings as defined above, with an amine presented by the general formula (III):

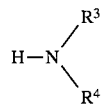
(III)

wherein $R^3$ and $R^4$ have the same meanings as defined above. In this reaction, the compounds of the present invention (I) can be obtained in good yields by reacting generally 0.5 molar equivalent or more, preferably from 0.9 to 1.5 molar equivalent of the amine (III) to the 3,4,5,6-tetrahydroisophthalimide derivative (IV).

The reaction can be conducted in a solvent, for example, a halogenated hydrocarbon solvent such as methylene chloride, chloroform, carbon tetrachloride and chlorobenzene, a hydrocarbon solvent such as benzene, toluene, xylene, hexane, octane and cyclohexane, an ether solvent such as diethyl ether, dioxane, tetrahydrofuran and dimethoxyethane, a ketone solvent such as acetone and methyl ethyl ketone, an inert solvent such as acetonitrile, ethyl acetate and dimethylformamide, or a mixed solvent thereof.

The reaction temperature is generally selected from a range of from 0° C. to 100° C. The reaction time varies depending upon the type of reaction materials, and generally the reaction is completed within 5 minutes to 24 hours.

Also, the reaction can be carried out by adding a catalyst for the purpose of promoting the reaction. The catalyst which is generally used includes a basic compound such as triethylamine, N-methylmorpholine, pyridine, N,N-dimethylaniline, potassium carbonate and sodium carbonate.

Further, the tetrahydroisophthalimide derivatives of the present invention represented by the above general formula (IV) which are starting mterials of the compounds (I) of the present invention can be prepared according to the process shown by the following formulae:

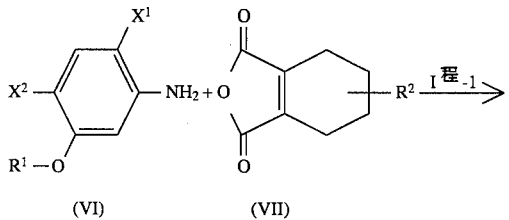

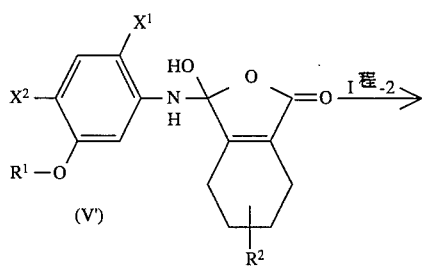

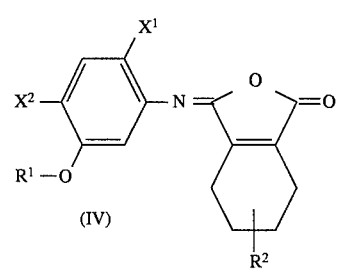

wherein $X^1$, $X^2$ and $R^1$ have the same meanings as defined above.

More specifically, Step-1 is a step of reacting an aniline derivative presented by the general formula (VI) with a 3,4,5,6-tetrahydrophthalic anhydride represented by the general formula (VII) in an organic solvent at a low temperature to convert it into a 3,4,5,6-tetrahydroisophthalimidohydroxy derivative represented by the general formula (V').

The organic solvent used in the reaction of Step-1 may be any solvents which do not adversely affect the reaction, and examples of the solvent which can be used include ketones such as acetone, methyl ethyl ketone, methyl isobutyl ketone and cyclohexanone, aromatic hydrocarbons such as benzene, toluene, xylene, chlorobenzene and dichlorobenzene, aliphatic hydrocarbons such as hexane, heptane, octane and petroleum ether, ethers such as diethyl ether, diisopropyl ether, dioxane, tetrahydrofuran and ethylene glycol dimethyl ether, esters such as ethyl acetate, butyl acetate and methyl formate, nitriles such as acetonitrile and isobutyronitrile, carboxylic acids such as acetic acid and propionic acid, or a mixed solvent thereof.

The reaction temperature is selected between 0° C. and 100° C., but the reaction is preferably conducted at a low temperature below 50° C. from the standpoint of good yields. After completion of the reaction, usual post-treatments are performed and, if necessary, the product can be purified by the procedure such as chromatography and recrystallization.

Generally, in the reaction of the aniline derivative represented by the general formula (VI) with the 3,4,5,6-tetrahydrophthalic anhydride represented by the general formula (VII), the reaction chemically provides a ring-opened 3,4,5,6-tetrahydrophthalamic acid derivative represented by the following general formula (VIII):

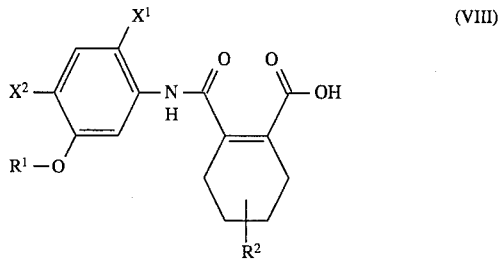

wherein $X^1$, $X^2$, $R^1$ and $R^2$ have the same meanings as defined above, due to attack of the amino group to the carbonyl group of the acid anhydride, but, in the case of using the aniline derivative (VI) having a cycloalkyloxy group at the 5-position of the phenyl ring, it is considered that an intramolecular cyclization further occurs easily due to steric and electronic factors whereby the product is obtained as a more stable 3,4,5,6-tetrahydroisophthalimidohydroxy derivative represented by the general formula (V').

Step-2 is a step of reacting a 3,4,5,6-tetrahydroisophthalimidohydroxy derivative represented by the general formula (V') in the presence of a dehydrating agent in an organic solvent to produce a 3,4,5,6-tetrahydroisophthalimide derivative represented by the general formula (IV).

The organic solvent used in this step may be any solvents which do not adversely affect the reaction, and examples of the solvent which can be used include ketones such as acetone, methyl ethyl ketone, methyl isobutyl ketone and cyclohexanone, aromatic hydrocarbons such as benzene, toluene, xylene, chlorobenzene and dichlorobenzene, aliphatic hydrocarbons such as hexane, heptane, octane and petroleum ether, ethers such as diethyl ether, diisopropyl ether, dioxane, tetrahydrofuran and ethylene glycol dimethyl ether, esters such as ethyl acetate, butyl acetate and methyl formate, nitriles such as acetonitrile and isobutyronitrile, carboxylic acids such as acetic acid and propionic acid, or a mixed solvent thereof.

Examples of the dehydrating agent include carbodiimides such as dicyclohexylcarbodiimide, diisopropylcarbodiimide and diethylcarbodiimide, halogenating agents such as thionyl chloride, 2,4,6-triisopropylbenzenesulfonyl chloride, mesitylenesulfonyl chloride, phosphorus oxychloride and phosgene, and polyphosphoric acid esters. Although the amount of the dehydrating agent to be used is not limited, the use of about 1 to 3 molar equivalents relative to the starting material is preferred from the standpoint of good yields and easy post-treatment.

The reaction temperature is selected between −30° and 100°, the reaction is preferably conducted at a low temperature of from about 0° to room temperature from the standpoint of good yields. After completion of the reaction, usual post-treatments are performed and, if necessary, the product can be purified by the procedure such as chromatography and recrystallization.

Examples of the 3,4,5,6-tetrahydroisophthalimide derivatives represented by the above-described general formula (IV) which can be prepared as described above and which are starting materials for the preparation of the compounds of the present invention include N-(2-fluoro-4 -chloro-5-cyclopropyloxyphenyl)-3,4,5,6-tetrahydroisophthalimide, N-(2-fluoro-4-chloro-5-cyclopentyloxyphenyl)- 3,4,5,6-tetrahydroisophthalimide, N-{2-fluoro-4-chloro-5 -(2-methylcyclopentyl)oxyphenyl}-3,4,5,6-tetrahydroisophthalimide, N-{2-fluoro-4-chloro-5-(3-methylcyclopentyl)oxyphenyl)-3,4,5,6-tetrahydroisophthalimide, N-(2-fluoro-4-chloro-5-cyclohexyloxyphenyl)-3,4,5,6 -tetrahydroisophthalimide, N-{2-fluoro-4-chloro-5-(2 -chlorocyclohexyl)oxyphenyl}-3,4,5,6-tetrahydroisophthalimide, N-(2-fluoro-4-chloro-5-cyclooctyloxyphenyl)- 3,4,5,6-tetrahydroisophthalimide, N-(2-fluoro- 4-bromo-5-cyclopropyloxyphenyl)-3,4,5,6-tetrahydroisophthalimide, N-(2-fluoro-4-bromo-5-cyclopentyloxyphenyl)- 3,4,5,6-tetrahydroisophthalimide, N-{2-fluoro- 4-bromo-5-(2-methylcyclopentyl)oxyphenyl}-3,4, 5,6 -tetrahydroisophthalimide, N-{2-fluoro-4-bromo-5-(3 -methylcyclopentyl)oxyphenyl}-3,4,5,6-tetrahydroisophthalimide, N-(2-fluoro-4-bromo-5-cyclohexyloxyphenyl)-3,4,5,6-tetrahydroisophthalimide, N-(2,4-dichloro-5-cyclopropyloxyphenyl)- 3,4,5,6-tetrahydroisophthalimide, N-(2, 4-dichloro-5-cyclopentyloxyphenyl)-3,4,5,6-tetrahydroisophthalimide, N-{2,4-dichloro-5-(2-methylcyclopentyl)oxyphenyl}- 3,4,5,6- tetrahydroisophthalimide, N-{2,4-dichloro-5-(3-methylcyclopentyl)oxyphenyl]-3,4,5,6 -tetrahydroisophthalimide, N-(2,4-dichloro-5-cyclohexyloxyphenyl)- 3,4,5,6-tetrahydroisophthalimide, N-(2,4-dichloro- 5-cyclooctyloxyphenyl)-3,4,5,6-tetrahydroisophthalimide, N-(2-fluoro-4-chloro-5-cyclopentyloxyphenyl)-3-methyl- 3,4,5,6-tetrahydroisophthalimide, N-(2-fluoro-4-chloro-5 -cyclopentyloxyphenyl)-4-methyl-3,4,5,6-tetrahydroisophthalimide, N-(2-fluoro-4-chloro-5-cyclopentyloxyphenyl)- 4-chloro-3,4,5,6-tetrahydroisophthalimide, N-{2-fluoro-4 -chloro-5-(3-methylcyclopentyl)oxyphenyl}-3-methyl-3,4,5,6 -tetrahydroisophthalimide, N-{2-fluoro-4-chloro-5-(3-methylcyclopentyl)oxyphenyl}-4-methyl-3,4,5,6-tetrahydroisophthalimide, N-(2-fluoro-5-cyclopentyloxyphenyl)-3, 4,5,6 -tetrahydroisophthalimide, N-{2-fluoro-5-(2-methylcyclopentyl)oxyphenyl- 3,4,5,6-tetrahydroisophthalimide, N-{2-fluoro- 5-(3-methylcyclopentyl)oxyphenyl-3,4,5,6-tetrahydroisophthalimide, and N-(2-fluoro-5-cyclohexyloxyphenyl)- 4-methyl-3,4,5,6-tetrahydroisophthalimide.

Also, the aniline derivatives represented by the general formula (VI) which are starting materials for the production of the tetrahydrophthalimide derivatives (II) or the 3,4,5,6-tetrahydroisophthalimide derivative (IV) of the present invention can be prepared, for example, in accordance with the process of Reference Examples described in the specification of Japanese Patent Publication (Kokai) No. 4-164067, but they can also be prepared, for example, according to the process illustrated by the following reaction scheme (refer to Reference Examples 1 to 7 described hereinafter):

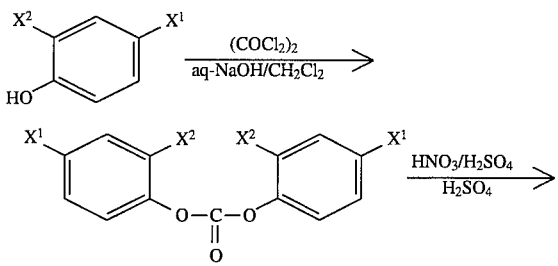

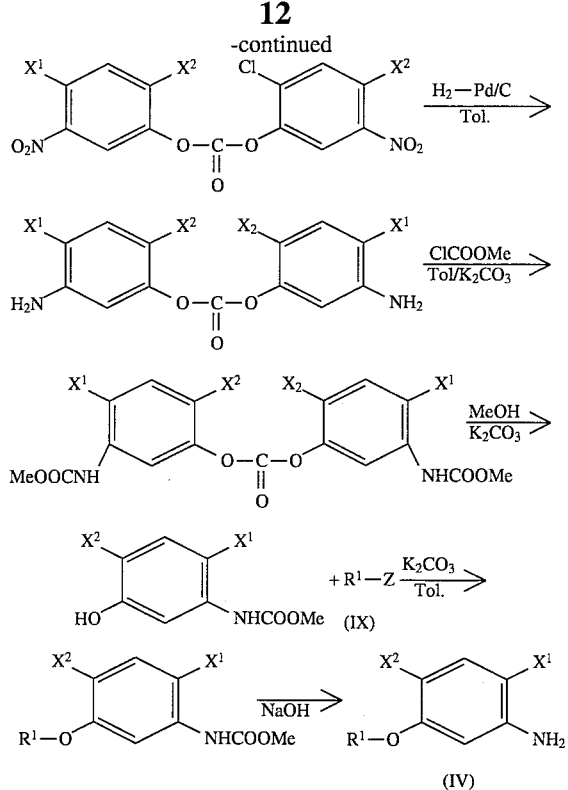

wherein $X^1$, $X^2$ and $R^1$ have the same meanings as defined above, and Z represents a removable group such as a halogen atom such as a bromine atom or an iodine atom or a sulfonyloxy group such as a p-toluenesulfonyloxy group, a benzenesulfonyloxy group and a methanesulfonyloxy group.

Further, the aniline derivatives represented by the general formula (VI) can be easily prepared by reacting a hydroxyaniline derivative represented by the general formula (X) (for example, Japanese Patent Publication No. 2-26622) and a cycloalkylating agent represented by the general formula $R^1Z$ (IX) in the presence of a phase transition catalyst, for example, by reacting in a two-layer system of a sodium hydroxide aqueous solution and toluene under heating, or by reacting in the presence of a base, for example, potassium carbonate, in a solvent such as dimethylformamide under heating (refer to Reference Examples 8 to 16 hereinafter described).

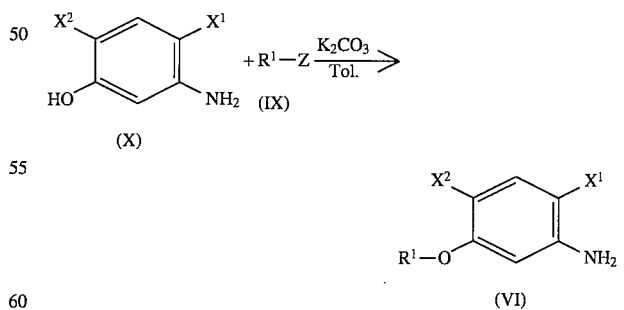

wherein $X^1$, $X^2$ and $R^1$ have the same meanings as defined above, and Z represents a removable group such as a halogen atom such as a bromine atom or an iodine atom or a sulfonyloxy group such as a p-toluenesulfonyloxy group, a benzenesulfonyloxy group and a methanesulfonyloxy group.

Further, the amines represented by the above general formula (III) which are starting materials for preparing the compounds of the present invention can be commercially available compounds or compounds which can be synthesized by using ordinary chemical synthesis procedures, and these amines may be used in a free form or in a form of a salt which does not adversely affect the reaction. Salts of the amines (III) which can be used include salts of inorganic or organic acids, for example, a hydrogen halide such as hydrogen chloride or hydrogen bromide, sulfuric acid, acetic acid, and p-toluenesulfonic acid.

The present invention is further described in greater detail by the following examples and reference examples, but the present invention is not limited to these examples.

EXAMPLE 1

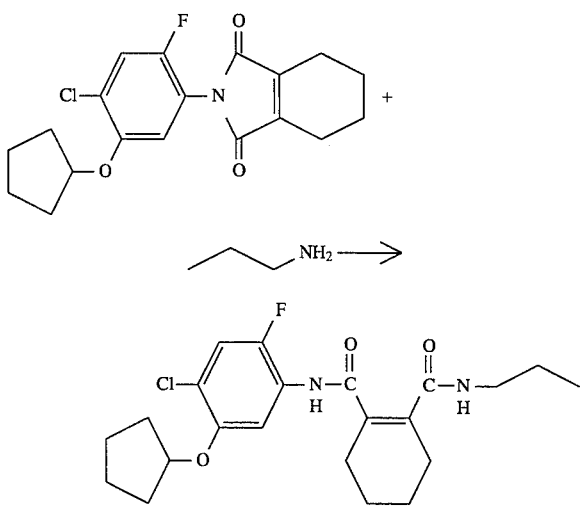

N-(2-Fluoro-4-chloro-5-cyclopentyloxyphenyl)- 3,4,5,6-tetrahydrophthalimide (1.00 g, 2.75 mmol), propylamine (0.190 g, 3.21 mmol) and benzene (25 ml) as a solvent were placed into a round bottom flask (50 cc) and stirred for 6 hours at room temperature. After completion of the reaction, the precipitated crystals were isolated by filtration. The crystals were washed with hexane and dried to obtain N-(2-fluoro-4-chloro-5-cyclopentyloxyphenyl)-N'-propyl- 3,4,5,6-tetrahydrophthalamide as white crystals (0.360 g, 30.9% yield).

Melting point: 138°–140° C.

$^1$N-NMR(CDCl$_3$,TMS,ppm): δ0.78(3H,t,J=6.0Hz), 1.40(2H,m), 1.70(4H,m), 1,87(8H,m), 2.37(4H,m), 3.18(2H,dt, J=6.0 and 6.0Hz), 4.80(1H,m), 5.85(1H,m), 7.11(1H, d, J$_{HF}$=10.5Hz), 7.97 (1H, brs), 8.08 (1H, d, J$_{HF}$=7.5Hz).

IR(KBr disk, cm$^{-1}$): 1200, 1390, 1485, 1500, 1620, 1640, 2950, 3520.

EXAMPLE 2

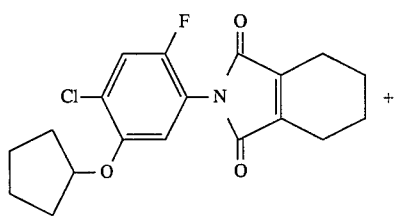

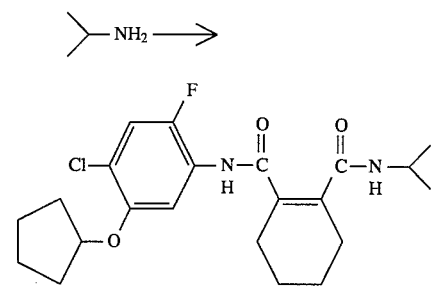

N-(2-Fluoro-4-chloro-5-cyclopentyloxyphenyl)- 3,4,5,6-tetrahydrophthalimide (1.00 g, 2.75 mmol), isopropylamine (0.600 g, 10.2 mmol) and benzene (25 ml) as a solvent were placed into a round bottom flask (50 cc) and stirred overnight at room temperature. After completion of the reaction, the precipitated crystals were isolated by filtration. The crystals were washed with hexane and dried to obtain N-(2-fluoro-4-chloro-5-cyclopentyloxyphenyl)-N'-isopropyl- 3,4,5,6-tetrahydrophthalamide as white crystals (0.700 g, 60.0% yield).

Melting point: 169°–171° C.

$^1$H-NMR(CDCl$_3$,TMS,ppm): δ1.00(6H,d,J=6.0Hz), 1.67(4H,m), 1.82(8H,m), 2.37(4H,m), 4.05(1H,d&sep,J=6.0 and 6.0Hz), 4.80(1H,m), 5.65(1H,d,J=6.0Hz), 7.10(1H, d, J$_{HF}$=10.5Hz), 7.95(1H, brs), 8.14(1H, d, J$_{HF}$=7.5Hz)

IR(KBr disk, cm$^{-1}$): 870, 1200, 1420, 1495, 1525, 1630, 1650, 2950, 3300.

EXAMPLE 3

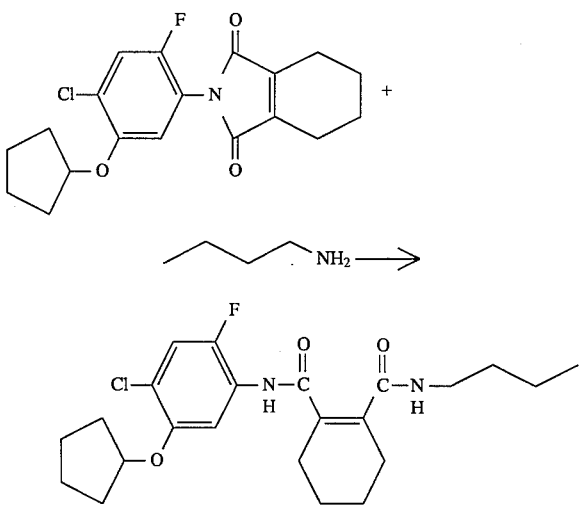

N-(2-Fluoro-4-chloro-5-cyclopentyloxyphenyl)- 3,4,5,6-tetrahydrophthalimide (1.50 g, 4.12 mmol), butylamine (0.420 g, 5.74 mmol) and benzene (25 ml) as a solvent were placed into a round bottom flask (50 cc) and stirred overnight at room temperature. After completion of the reaction, the precipitated crystals were isolated by filtration. The crystals were washed with hexane and dried to obtain N-(2-fluoro-4-chloro-5-cyclopentyloxyphenyl)-N'-butyl- 3,4,5,6-tetrahydrophthalamide as white crystals (1.11 g, 61.7% yield).

Melting point: 142°–144° C.

$^1$H-NMR(CDCl$_3$,TMS,ppm): δ0.75(3H,t,J=7.0Hz), 1.27(4H,m), 1.70(4H,m), 1.90(8H,m), 2.37(4H,m), 3.20(2H,m), 4.82(1H,m), 5.83(1H,m), 7.10(1H,d, J$_{HF}$=10.5Hz), 8.00(1H,brs), 8.12(1H,d,J$_{HF}$=7.5Hz)

IR(KBr disk, cm$^{-1}$): 670, 860, 1195, 1250, 1410, 1490, 1520, 1640, 2950, 3300.

EXAMPLE 4

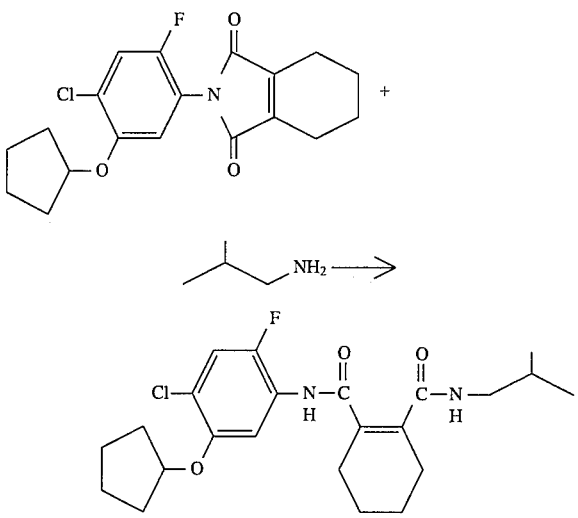

N-(2-Fluoro-4-chloro-5-cyclopentyloxyphenyl)- 3,4,5,6-tetrahydrophthalimide (1.00 g, 2.75 mmol), isobutylamine (0.240 g, 3.28 mmol), triethylamine (0.310 g, 3.06 mmol) and benzene (25 ml) as a solvent were placed into a round bottom flask (50 cc) and stirred overnight at room temperature. After completion of the reaction, the precipitated crystals were isolated by filtration. The crystals were washed with hexane and dried to obtain N-( 2-fluoro-4-chloro-5-cyclopentyloxyphenyl)-N'-isobutyl- 3,4,5,6-tetrahydrophthalamide as white crystals (0.936 g, 77.8% yield).

Melting point: 161°–163° C.

$^1$H-NMR(CDCl$_3$,TMS,ppm): δ0.77(6H,d,J=6.0Hz), 1.5–2.1(13H, m), 2.40(4H,m), 3.07(2H,dd,J=6.0Hz), 4.80(1H, m), 5.95(1H,brt,J=6.0Hz), 7.18(1H,d, J$_{HF}$=10.5Hz), 8.10(1H, brs), 8.20(1H, d, J$_{HF}$=7.5Hz)

IR(KBr disk, cm$^-$): 860, 1180, 1240, 1410, 1480, 1530, 1610, 1670, 2940, 3270.

EXAMPLE 5

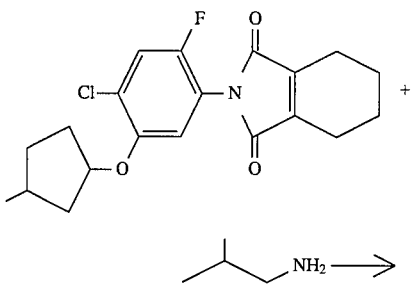

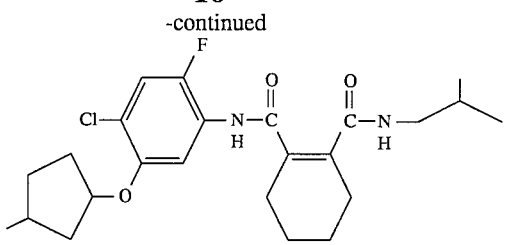

N-{2-Fluoro-4-chloro-5-(3-methylcyclopentyl)oxyphenyl}-3,4,5,6-tetrahydrophthalimide (1.20 g, 3.18 mmol), isobutylamine (0.360 g, 4.92 mmol), triethylamine (0.450 g, 4.44 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-{2-fluoro-4-chloro-5-(3-methylcyclopentyl)oxyphenyl}-N'-isobutyl-3,4,5,6-tetrahydrophthalamide as white crystals (0.700 g, 48.7% yield).

Melting point: 144°–147° C.

$^1$H-NMR(CDCl$_3$,TMS,ppm): δ0.78(6H,d,J=6.0Hz), 1.03 and 1.10(total 3H, each d,J=6.0Hz), 1.30–2.30(12H,m), 2.35(4H,m), 3.03(2H,dd,J=6.0 and 6.0Hz), 4.75(1H, m), 6.03(1H,brt,J=6.0Hz), 7.08(1H,d,J$_{HF}$=10.5Hz), 8.05(1H,d, J$_{HF}$=7.5Hz), 8,12(1H,brs).

IR(KBr disk, cm$^{-1}$): 860, 1190, 1410, 1490, 1520, 1640, 2950, 3300.

EXAMPLE 6

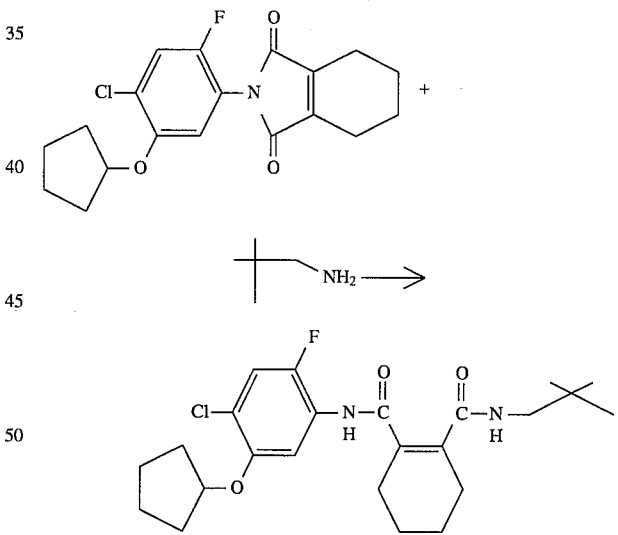

N-(2-Fluoro-4-chloro-5-cyclopentyloxyphenyl)- 3,4,5,6-tetrahydrophthalimide (1.00 g, 2.75 mmol), 2,2-dimethylpropylamine (0.310 g, 3.56 mmol), triethylamine (0.280 g, 2.77 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 2,2-dimethylpropyl)-3,4,5,6-tetrahydrophthalamide as white crystals (0.660 g, 53.1% yield).

Melting point: 173°–175° C.

$^1$H-NMR(CDCl$_3$,TMS,ppm): δ0.82(9H, s), 1.72(4H,m), 1.85(8H, m), 2.37(4H,m), 3.00(2H,d,J=7.5Hz), 4.73(1H, m), 5.83(1H, t,J=7.5Hz), 7.07(1H,d, J$_{HF}$=10.5Hz), 8.00(1H,brs), 8,07(1H,d,J$_{HF}$=7.5Hz).

IR(KBr disk, cm$^{-1}$): 680, 860, 1190, 1490, 1640, 2950, 3300.

EXAMPLE 7

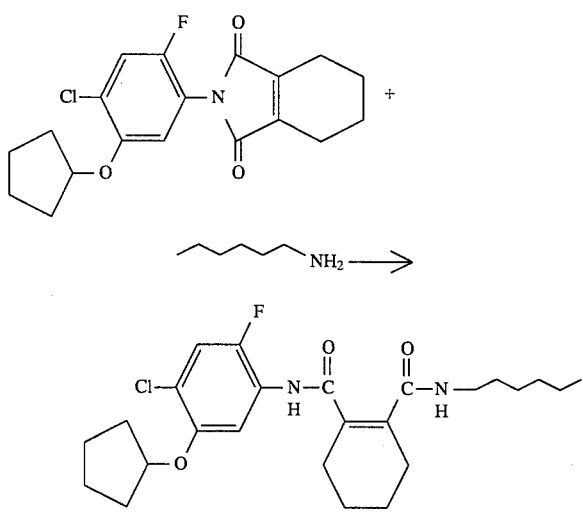

N-(2-Fluoro-4-chloro-5-cyclopentyloxyphenyl)- 3,4,5,6-tetrahydrophthalimide (1.00 g, 2.75 mmol), hexylamine (0.330 g, 3.26 mmol), triethylamine (0.310 g, 3.06 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-( 2-fluoro-4-chloro-5-cyclopentyloxyphenyl)-N'-hexyl- 3,4,5,6-tetrahydrophthalamide as white crystals (1.06 g, 83.3% yield).

Melting point: 128°–130° C.

$^1$H-NMR(CDCl$_3$,TMS,ppm): δ0.82(3H, t,J=6.0Hz), 1.13(8H,m), 1.70(4H,m), 1.87(8H,m), 2.33(4H,m), 3.18(2H,dt, J=6.0 and 6.0Hz), 4.77(1H,m), 5.88(1H,m), 7.10(1H, d, J$_{HF}$=10.5Hz), 8.00(1H,brs), 8.12(1H,d, J$_{HF}$=7.5Hz).

IR(KBr disk, cm$^{-1}$): 858, 1185, 1400, 1480, 1510, 1640, 2900, 3270.

EXAMPLE 8

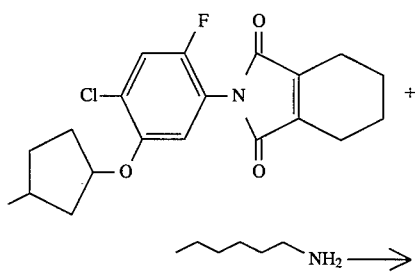

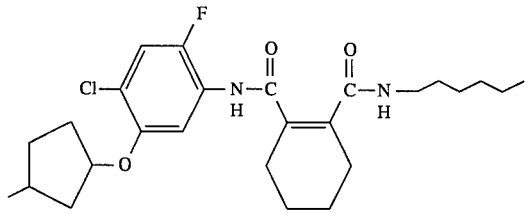

N-{2-Fluoro-4-chloro-5-(3-methylcyclopentyl)oxyphenyl}- 3,4,5,6-tetrahydrophthalimide (1.26 g, 3.33 mmol), hexylamine (0.410 g, 4.05 mmol), triethylamine (0.380 g, 3.76 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-{2-fluoro-4-chloro-5-(3-methylcyclopentyl)oxyphenyl}-N'-hexyl-3,4,5,6-tetrahydrophthalamide as white crystals (1.29 g, 80.8% yield).

Melting point: 127°–129° C.

$^1$H-NMR(CDCl$_3$,TMS,ppm): δ0.82(3H,brt), 1.00–2.20(22H,m), 2.40(4H,m), 3.22(2H,dt,J=6.0 and 6.0Hz), 4.85(1H, m), 5.90(1H,m), 7.18(1H,d,J$_{HF}$=10.5Hz), 8.07(1H,brs), 8.18 (1H, d, J$_{HF}$=7.5Hz).

IR(KBr disk, cm$^-$): 860, 1190, 1410, 1490, 1520, 1640, 2950, 3200.

EXAMPLE 9

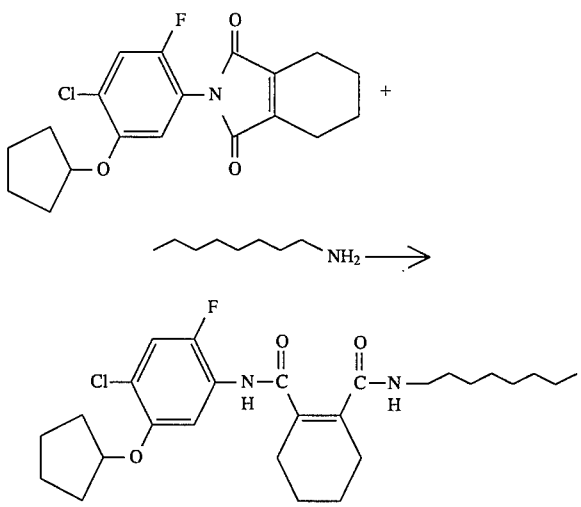

N-(2-Fluoro-4-chloro-5-cyclopentyloxyphenyl)- 3,4,5,6-tetrahydrophthalimide (1.00 g, 2.75 mmol), octylamine (0.460 g, 3.56 mmol), triethylamine (0.310 g, 3.06 mmol) and benzene (25 ml) as a solvent were placed into a round bottom flask (50 cc) and stirred overnight at room temperature. After completion of the reaction, the reaction mixture was poured into 1N hydrochloric acid (50 ml), and the mixture was extracted with ethyl acetate (50 ml×3 portions). The organic layer was dried over anhydrous magnesium sulfate, and the solvent was distilled off under reduced pressure. The resulting crude product was recrystallized from ether to obtain N-(2-fluoro-4-chloro- 5-cyclopentyloxyphenyl)-N'-octyl-3,4,5,6-tetrahydrophthalamide as white crystals (0.410 g, 30.2% yield).

Melting point: 127°–130° C.

¹H-NMR(CDCl₃, TMS, ppm): δ0.86 (3H, t, J=6.0Hz), 1.48 (12H, m), 1.68(4H,m), 1.87(8H,m) 2.37(4H,m), 3.18(2H,dt,J=6.0 and 6.0Hz), 4.77(1H,m), 5.90(1H,t,J=6.0Hz), 7.08(1H, d, J$_{HF}$=10.5Hz), 8.03 (1H, brs), 8.09 (1H, d, J$_{HF}$=7.5Hz).

IR(KBr disk, cm⁻): 680, 850, 970, 1020, 1180, 1250, 1290, 1400, 1480, 1520, 1620, 2900, 3250.

EXAMPLE 10

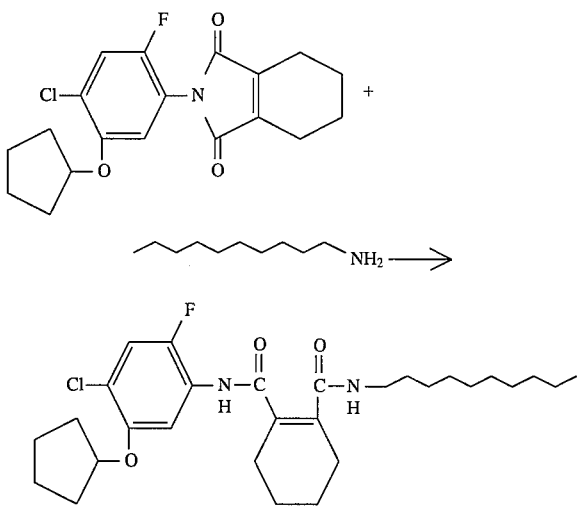

N-(2-Fluoro-4-chloro-5-cyclopentyloxyphenyl)- 3,4,5,6-tetrahydrophthalimide (1.00 g, 2.75 mmol), decylamine (0.520 g, 3.31 mmol), triethylamine (0.310 g, 3.06 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-( 2-fluoro-4-chloro-5-cyclopentyloxyphenyl)-N'-decyl- 3,4,5,6-tetrahydrophthalamide as white crystals (1.06 g, 73.8% yield).

Melting point: 128°–130° C.

¹H-NMR(CDCl₃,TMS,ppm): δ0.72(3H,brt,J=6.0Hz), 1.22(16H,m), 1.70(4H,m), 1.88(8H,m) 2.37(4H,m), 3.17(2H,dt, J=6.0 and 6.0Hz), 4.75(1H,m), 5.83(1H,brt,J=6.0Hz), 7.07(1H,d, J$_{HF}$=10.5Hz), 7.97(1H,brs), 8.07(1H,d, J$_{HF}$=7.5Hz).

IR(KBr disk, cm⁻¹): 860, 1190, 1250, 1410, 1490, 1520, 1640, 2925, 3300.

EXAMPLE 11

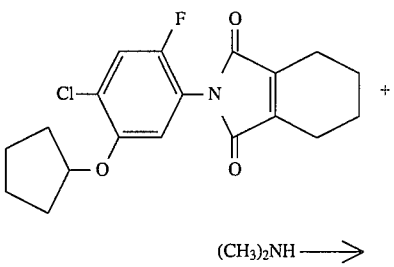

(CH₃)₂NH ⟶

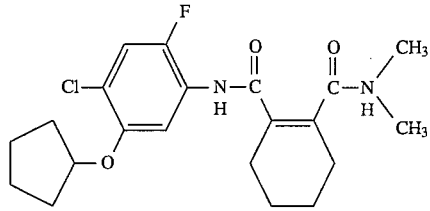

N-(2-Fluoro-4-chloro-5-cyclopentyloxyphenyl)- 3,4,5,6-tetrahydrophthalimide (1.00 g, 2.75 mmol), a 40% aqueous solution of dimethylamine (0.410 g, 3.64 mmol), and carbon tetrachloride (25 ml) were placed into a round bottom flask (50 cc) and stirred overnight at room temperature. After completion of the reaction, the solvent was distilled off under reduced pressure, and the resulting semi-solid product was recrystallized by adding hexane to obtain N-(2-fluoro-4-chloro-5-cyclopentyloxyphenyl)-N',N'-dimethyl- 3,4,5,6-tetrahydrophthalamide as white crystals (0.410 g, 36.4% yield).

Melting point: 136°–138° C.

¹H-NMR(CDCl₃,TMS,ppm): δ1.73(4H,m), 1.85(8H,m), 2.33(4H, m), 2.91(3H,s), 4.77(1H,m), 7.05(1H,d,J$_{HF}$=10.5Hz), 7.93(1H,d,J$_{HF}$=7.5Hz), 8.30(1H,brs).

IR(KBr disk, cm⁻¹): 870, 1190, 1280, 1395, 1500, 1620, 2950, 3200.

EXAMPLE 12

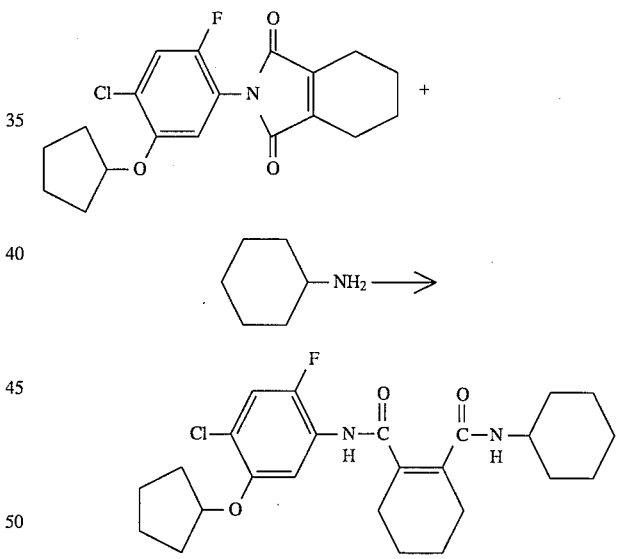

N-(2-Fluoro-4-chloro-5-cyclopentyloxyphenyl)- 3,4,5,6-tetrahydrophthalimide (1.00 g, 2.75 mmol), cyclohexylamine (0.360 g, 3.63 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-cyclohexyl- 3,4,5,6-tetrahydrophthalamide as white crystals (0.579 g, 45.5% yield).

Melting point: 209°–211° C.

¹H-NMR(CDCl₃, TMS, ppm): δ0.8–2.1 (22H, m), 2.37 (4H, m), 3.75(1H,m), 4.78(1H,m), 5.70(1H,brd,J=7.5Hz), 7.10 (1H, d, $J_{HF}$=10.5Hz), 7.93 (1H, brs), 8.13 (1H, d, $J_{HF}$=7.5Hz).

IR(KBr disk, cm$^{-1}$): 860, 1180, 1240, 1400, 1480, 1510, 1605, 1640, 2900, 3270.

EXAMPLE 13

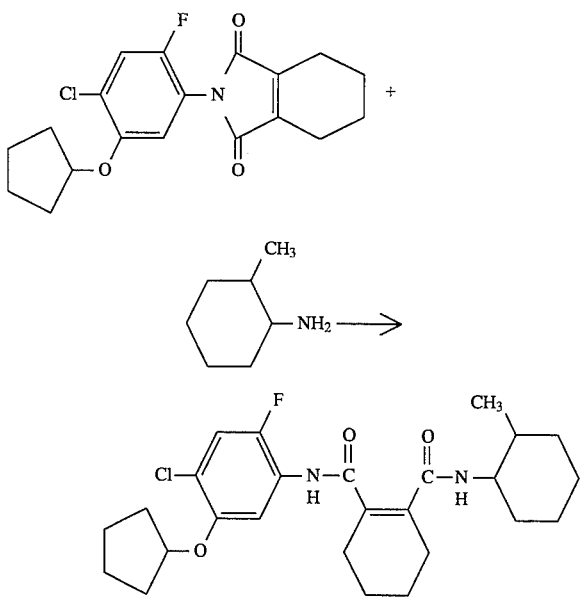

N-(2-Fluoro-4-chloro-5-cyclopentyloxyphenyl)- 3,4,5,6-tetrahydrophthalimide (1.00 g, 2.75 mmol), 2-methylcyclohexylamine (0.620 g, 5.48 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(2-methylcyclohexyl)-3,4,5,6-tetrahydrophthalamide as white crystals (0.373 g, 28.4% yield).

Melting point: 192°–195° C.

400 MHz $^1$H-NMR(CDCl$_3$,TMS,ppm): δ0.73 and 0.74(total 3H, each d,J=7.0Hz), 1.10–2.10(21H,m), 2.40(4H,m), 3.43 and 4.02(total 1H, each m), 4.77(1H,m), 5.59 and 5.84(total 1H, each brd, J=6.5 and 8.5Hz), 7,097 and 7,099(total 1H, each d, $J_{HF}$=10.5Hz and 10.5Hz), 8.01 and 8.10(total 1H, each brs), 8.14 and 8.17(total 1H, each d,$J_{HF}$=7.5 and 7.5Hz).

IR(KBr disk, cm$^{-1}$): 860, 1190, 1250, 1410, 1490, 1520, 1620, 1642, 2940, 3300.

EXAMPLE 14

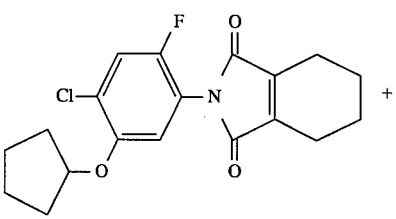

-continued

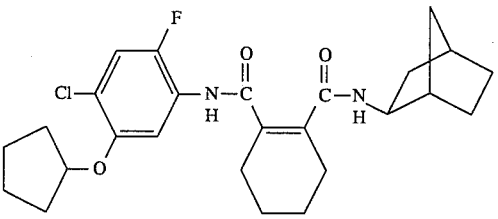

N-(2-Fluoro-4-chloro-5-cyclopentyloxyphenyl)- 3,4,5,6-tetrahydrophthalimide (1.00 g, 2.75 mmol), exo- 2-aminonorbornane (0.390 g, 3.51 mmol), triethylamine (0.310 g, 3.06 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(exo-norbornyl)- 3,4,5,6-tetrahydrophthalamide as white crystals (0.474 g, 36.3% yield).

Melting point: 231°–233° C.

$^1$H-NMR(CDCl$_3$,TMS,ppm): δ0.90–2.20(22H,m), 2.30(4H,m), 3.70(1H,m), 4.83(1H,m), 5.75(1H,d,J=7.5Hz), 7.18(1H,d,$J_{HF}$=10.5Hz), 8.00(1H,brs), 8.23(1H, d, $J_{HF}$=7.5Hz).

IR(KBr disk, cm$^-$): 680, 860, 1190, 1240, 1410, 1520, 1610, 1640, 1678, 2950, 3300.

EXAMPLE 15

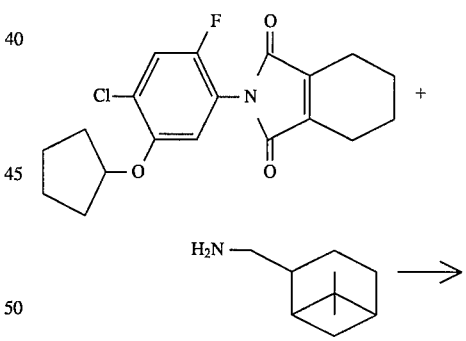

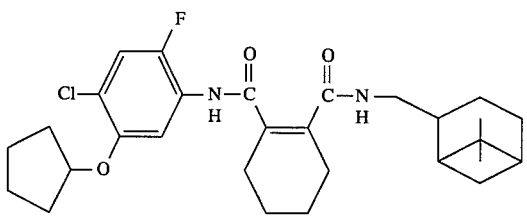

N-(2-Fluoro-4-chloro-5-cyclopentyloxyphenyl)- 3,4,5,6-tetrahydrophthalimide (1.00 g, 2.75 mmol), (–)-cis-myrtanylamine (0.460 g, 3.00 mmol), triethylamine (0.310 g, 3.06 mmol) and benzene (20 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro- 4-chloro-5-cyclopentyloxyphenyl)-N'-cis-myrtanyl- 3,4,5,6-tetrahydrophthalamide as white crystals (0.780 g, 56.0% yield).

Melting point: 175°–177° C.

Optical rotation: $[\alpha]_D = -1.03(c=0.962, CHCl_3, 20° C.)$ $^1$H-NMR(CDCl$_3$,TMS,ppm): δ0.93(3H,s), 1.10(3H,s), 1.20–2.10(27H,m), 2.35(4H,m), 3.18(2H,dd,J=6.0 and 1.5Hz), 4.73(1H,m), 5.80(1H,m), 7.05(1H,d, $J_{HF}$=10.5Hz), 7.92(1H,brs), 8.08(1H, d, $J_{HF}$=7.5Hz).

IR(KBr disk, cm$^{-1}$): 860, 1180, 1240, 1400, 1520, 1620, 2950, 3250.

EXAMPLE 16

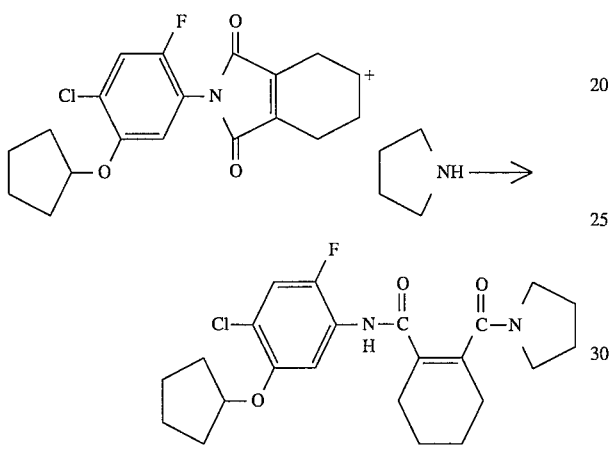

N-(2-Fluoro-4-chloro-5-cyclopentyloxyphenyl)- 3,4,5,6-tetrahydrophthalimide (0.700 g, 1.92 mmol), pyrrolidine (0.200 g, 2.81 mmol) and benzene (25 ml) as a solvent were placed into a round bottom flask (50 cc) and stirred overnight at room temperature. After completion of the reaction, the reaction mixture was poured into 1N hydrochloric acid (50 ml), and the mixture was extracted with ethyl acetate (50 ml×3 portions). The organic layer was dried over anhydrous magnesium sulfate, and the solvent was distilled off under reduced pressure. The resulting crude product was recrystallized from ether/hexane to obtain N-(2-fluoro-4-chloro-5-cyclopentyloxyphenyl)-N',N'-tetramethylene- 3,4,5,6-tetrahydrophthalamide as white crystals (0.610 g, 72.9% yield).

Meltingg point: 132°–134° C.

$^1$H-NMR(CDCl$_3$,TMS,ppm): δ1.1–2.1(16H,m), 2.38(4H, m), 3.38 (4H, brt, J=7.5Hz), 4.77 (1H, m), 7.08 (1H, d, $J_{HF}$=10.5Hz), 8.01(1H,d,$J_{HF}$=7.5Hz), 8.33(1H,brs).

IR(KBr disk, cm$^{-1}$): 860, 1190, 1275, 1385, 1440, 1490, 1600, 2920, 3150.

EXAMPLE 17

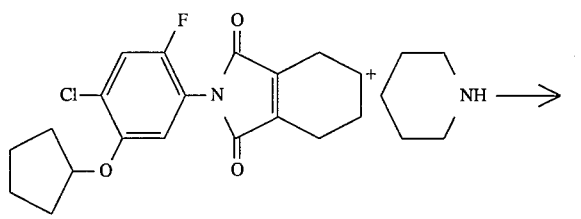

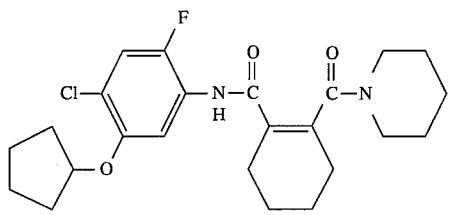

N-(2-Fluoro-4-chloro-5-cyclopentyloxyphenyl)- 3,4,5,6-tetrahydrophthalimide (0.700 g, 1.92 mmol), piperidine (0.210 g, 2.47 mmol) and benzene (25 ml) as a solvent were placed into a round bottom flask (50 cc) and stirred overnight at room temperature. After completion of the reaction, the reaction mixture was poured into 1N hydrochloric acid (50 ml), and the mixture was extracted with ethyl acetate (50 ml×3 portions). The organic layer was dried over anhydrous magnesium sulfate, and the solvent was distilled off under reduced pressure. The resulting crude product was recrystallized from ether/hexane to obtain N-(2-fluoro-4-chloro-5-cyclopentyloxyphenyl)-N',N'-pentamethylene- 3,4,5,6-tetrahydrophthalamide as white crystals (0.263 g, 30.5% yield).

Melting point: 113°–116° C.

$^1$H-NMR(CDCl$_3$,TMS,ppm): δ1,50(6H,m), 1.75(4H,m), 1.87(8H, m), 2.33(4H,m), 3.30(2H,m), 3.53(2H,m), 4.77(1H, m), 7.07(1H,d,$J_{HF}$=10.5Hz, 8.10(1H,d,$J_{HF}$=7.5Hz), 8.43(1H,brs).

IR(KBr disk, cm$^{-1}$): 860, 1180, 1250, 1400, 1480, 1520, 1615, 1650, 2900, 3250.

EXAMPLE 18

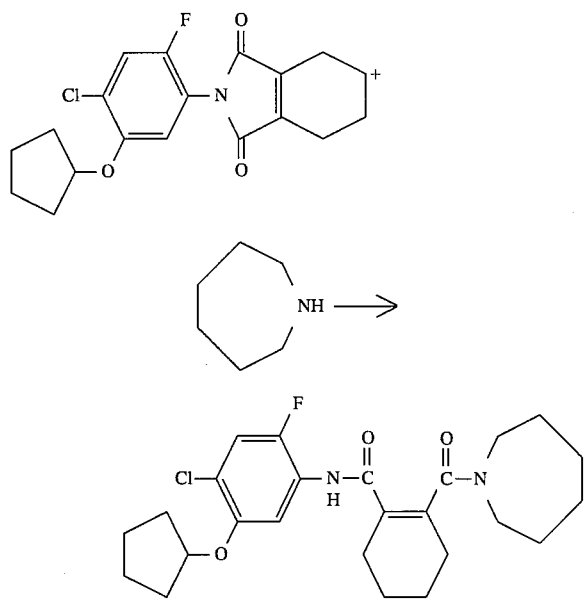

N-(2-Fluoro-4-chloro-5-cyclopentyloxyphenyl)- 3,4,5,6-tetrahydrophthalimide (1.50 g, 4.12 mmol), hexamethyleneimine (0.610 g, 6.15 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration.

The crystals were washed with hexane and dried to obtain N-(2-fluoro-4-chloro-5-cyclopentyloxyphenyl)-N',N'-hexamethylene-3,4,5,6-tetrahydrophthalamide as white crystals (1.55 g, 81.1% yield).

Melting point: 130°–132° C.

$^1$H-NMR(CDCl$_3$,TMS,ppm): δ1.25–2.10(20H,m), 2.33(4H,m), 3.25–3.65 (4H, m), 4.77 (1H, m), 7.08 (1H, d, J$_{HF}$=10.5Hz), 8.17(1H,d,J$_{HF}$=7.5Hz), 8.63(1H,brs).

IR(KBr disk, cm$^{-1}$): 675, 860, 1190, 1240, 1405, 1490, 1520, 1600, 1670, 2900, 3300.

EXAMPLE 19

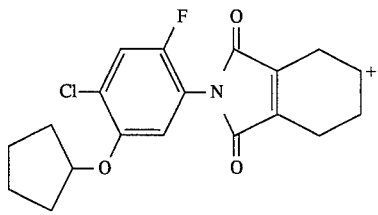

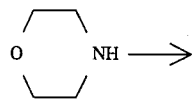

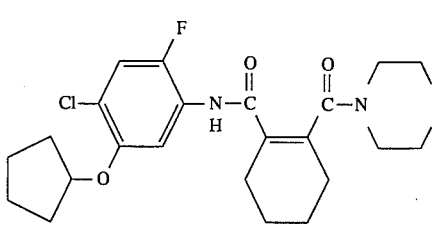

N-(2-Fluoro-4-chloro-5-cyclopentyloxyphenyl)- 3,4,5,6-tetrahydrophthalimide (1.00 g, 2.75 mmol), morpholine (0.320 g, 3.67 mmol) and benzene (20 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N',N'-diethyleneoxy- 3,4,5,6-tetrahydrophthalamide as white crystals (0.566 g, 45.8% yield).

Melting point: 135°–137° C.

$^1$H-NMR(CDCl$_3$,TMS,ppm): δ1.75(4H,m), 1.88(8H,m), 2.37(4H, m), 3.45(4H,m), 3.57(4H,m), 4.82(1H,m), 7.17(1H, d,J$_{HF}$=10.5Hz), 8.18(1H,d,J$_{HF}$=7.5Hz), 8.23(1H, brs).

IR(KBr disk, cm$^-$): 860, 990, 1105, 1185, 1240, 1410, 1490, 1530, 1620, 2920, 3270.

EXAMPLE 20

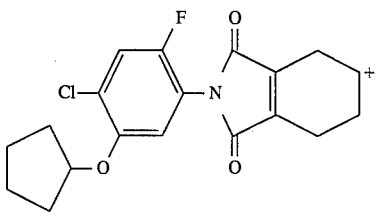

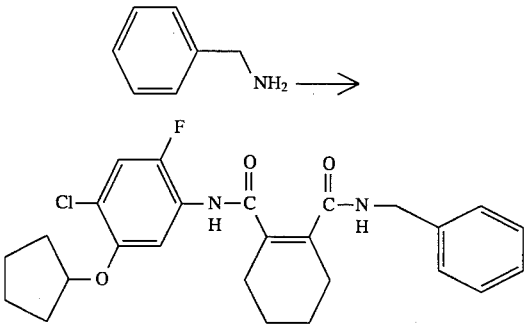

N-(2-Fluoro-4-chloro-5-cyclopentyloxyphenyl)- 3,4,5,6-tetrahydrophthalimide (1.00 g, 2.75 mmol), benzylamine (0.350 g, 3.27 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-benzyl- 3,4,5,6-tetrahydrophthalamide as white crystals (0.584 g, 45.1% yield).

Melting point: 145°–148° C.

$^1$H-NMR(CDCl$_3$,TMS,ppm): δ1.68(4H,m), 1.94(8H,m), 2.38(4H, m), 4.37(1H,d,J=6.0Hz), 4.72(1H,m), 6.20(1H, brt,J=6.0Hz), 7.07(1H,d,J$_{HF}$=10.0Hz), 7.13(5H, s), 7.93(1H, brs), 8.02(1H,d,J=7.5Hz).

IR(KBr disk, cm$^{-1}$): 670, 698, 730, 860, 1190, 1250, 1410, 1490, 1520, 1640, 2950, 3300.

EXAMPLE 21

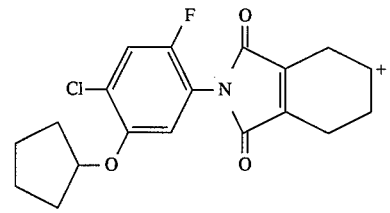

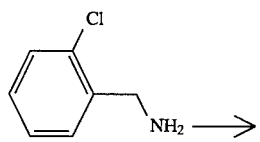

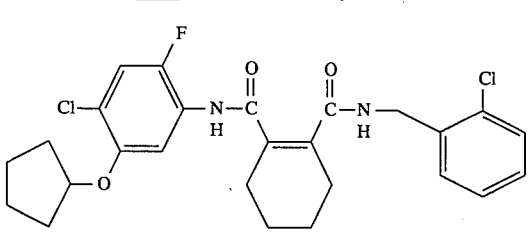

N-(2-Fluoro-4-chloro-5-cyclopentyloxyphenyl)- 3,4,5,6-tetrahydrophthalimide (0.500 g, 1.37 mmol), 2-chlorobenzylamine (0.240 g, 1.69 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(2-chlorobenzyl)-3,4,5,6-tetrahydrophthalamide as white crystals (0.590 g, 85.4% yield).

Meltingg point: 181°–183° C.

¹H-NMR(CDCl₃,TMS,ppm): δ1.68(4H,m), 1.87(8H,m), 2.37(4H, m), 4.42(2H,d,J=6.0Hz), 4.72(1H,m), 6.35(1H,brt, J=6.0Hz), 6.9–7.4(5H,m), 7.75 (1H, brs), 8.02 (1H, d, $J_{HF}$=7.5Hz).

IR(KBr disk, cm⁻¹): 750, 1420, 1500, 1540, 1623, 1690, 3000, 3320.

EXAMPLE 22

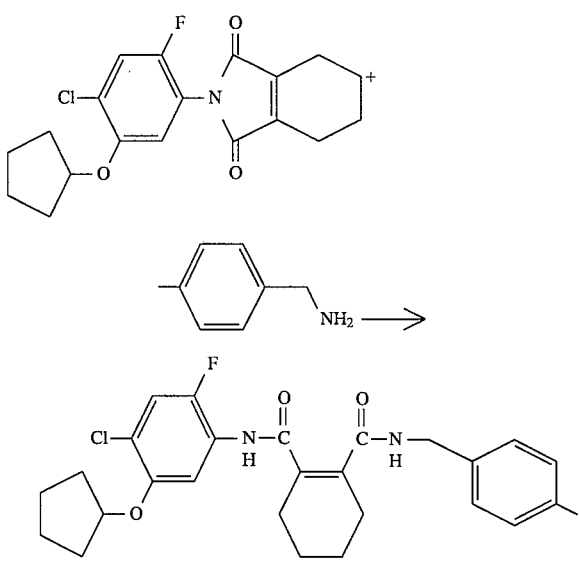

N-(2-Fluoro-4-chloro-5-cyclopentyloxyphenyl)- 3,4,5,6-tetrahydrophthalimide (0.700 g, 1.92 mmol), 4-methylbenzylamine (0.330 g, 2.72 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(4-methylbenzyl)-3,4,5,6-tetrahydrophthalamide as white crystals (0.741 g, 79.7% yield).

Melting point: 168°–169° C.

¹H-NMR(CDCl₃,TMS,ppm): δ1.68(4H,m), 1.88(8H,m), 2.23(3H, s), 2.38(4H,m), 4.33(2H,d,J=6.0Hz), 4.72(1H,m), 6.25(1H,t,J=6.0Hz), 6.92(2H,d,J=7.5Hz), 7.07(2H, d,J=7.5Hz), 7.13(1H,d,J=10.5Hz), 8.00(1H,brs), 8.05(1H,d,J=7.5Hz).

IR(KBr disk, cm⁻¹): 870, 1200, 1420, 1500, 1530, 1630, 1650, 2970, 3320.

EXAMPLE 23

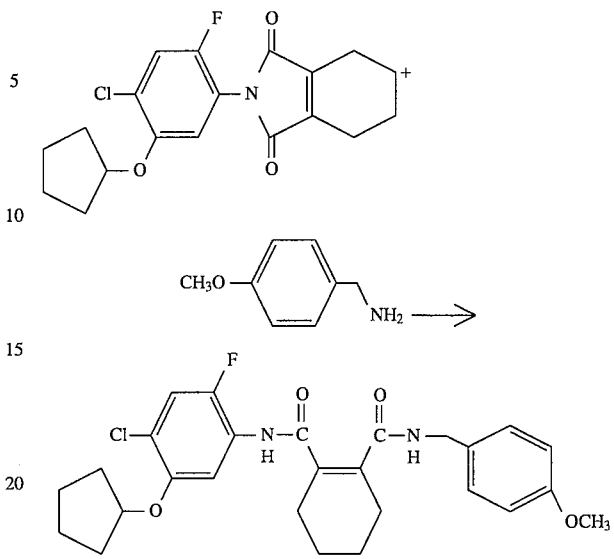

N-(2-Fluoro-4-chloro-5-cyclopentyloxyphenyl)- 3,4,5,6-tetrahydrophthalimide (1.00 g, 2.75 mmol), 2-methoxybenzylamine (0.380 g, 2.77 mmol), triethylamine (0.310 g, 3.06 mmol) and benzene (20 ml) as a solvent were placed into a round bottom flask (50 cc) and stirred overnight at room temperature. After completion of the reaction, the solvent was distilled off under reduced pressure, and the resuslting crude product was recrystallized from ether/hexane to obtain N-(2-fluorochloro- 5-cyclopentyloxyphenyl)-N'-(4-methoxybenzyl)- 3,4,5,6-tetrahydrophthalamide as white crystals (0.520 g, 37.8% yield).

Meltingg point: 161°–162° C.

¹H-NMR(CDCl₃,TMS,ppm): δ1.67(4H,m), 1.88(8H,m), 2.33(4H, m), 3.67(3H,s), 4.28(2H,d,J=6.0Hz), 4.67(1H,m), 6.07(1H,m), 6.53(2H,d,J=9.0Hz), 6.95(2H,d,J=9.0Hz), 7.02(1H,d,$J_{HF}$=10.5Hz), 7.88(1H,brs),7.92(1H,d, J=7.5Hz).

IR(KBr disk, cm⁻¹): 610, 820, 860, 1040, 1180, 1250, 1410, 1510, 1620, 2950, 3275.

EXAMPLE 24

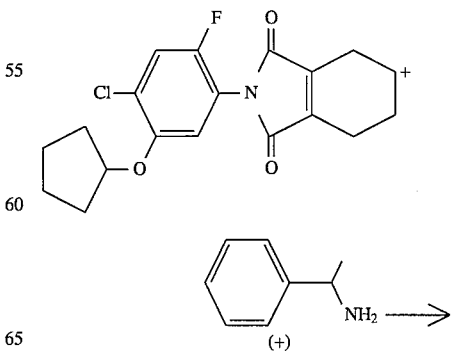

-continued

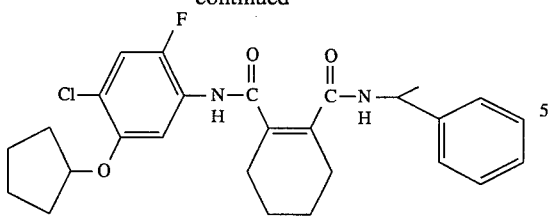

N-(2-Fluoro-4-chloro-5-cyclopentyloxyphenyl)- 3,4,5,6-tetrahydrophthalimide (1.50 g, 4.12 mmol), R-(+)- 1-phenylethylamine (0.650 g, 5.36 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 1-phenylethyl)-3,4,5,6-tetrahydrophthalamide as white crystals (1.20 g, 60.0% yield).

Meltingg point: 176°–178° C.

Optical Rotation: $[\alpha]_D$=+30.30(c=0.970,CHCl$_3$,20° C.)

$^1$H-NMR(CDCl$_3$, TMS, ppm): δ1.35 (3H, d, J=7.5Hz), 1.67 (4H, m), 1.87(8H,m), 2.35(4H,m), 4.72(1H,m), 5.03(1H,dq, J=7.5 and 7.5Hz), 6.07(1H,d,J=7.5Hz), 7.07(1H,d, $J_{HF}$=10.5Hz), 7.10(5H,S), 7.83(1H,brs), 8.07(1H, d,$J_{HF}$=7.5Hz).

IR(KBr disk, cm$^{-1}$): 700, 860, 1190, 1250, 1405, 1510, 1640, 2950, 3300.

EXAMPLE 25

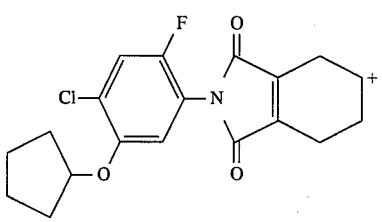

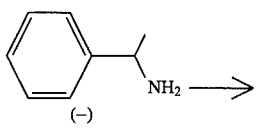

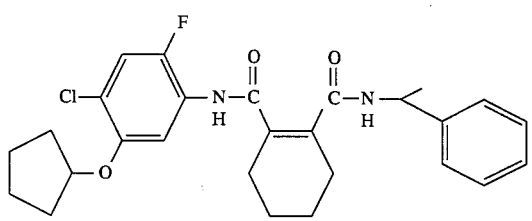

N-(2-Fluoro-4-chloro-5-cyclopentyloxyphenyl)- 3,4,5,6-tetrahydrophthalimide (1.10 g, 2.75 mmol), S-(−)- 1-phenylethylamine (0.400 g, 3.30 mmol), triethylamine (0.310 g, 3.06 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 1-phenylethyl)-8,4,5,6-tetrahydrophthalamide as white crystals (0.945 g, 70.9% yield).

Melting point: 173°–175° C.

Optical Rotation: $[\alpha]_D$=−27.86(c=0.994,CHCl$_3$,20° C.)

$^1$H-NMR(CDCl$_3$,TMS,ppm): δ1.33(3H,d,J=7.5Hz), 1.70(4H,m), 1.83(8H,m), 2.38(4H,m), 4.70(1H,m), 5.02(1H,dq, J=7.5Hz and 7.5Hz), 6.10(1H, d, J=7.5Hz), 7.02(1H, d,$J_{HF}$=10.5Hz), 7.10(5H,s), 7.83(1H,brs), 8.08(1H, d,$J_{HF}$=7.5Hz).

IR(KBr disk, cm$^{-1}$): 690, 878, 1182, 1400, 1480, 1510, 1620, 1640, 2950, 3250.

EXAMPLE 26

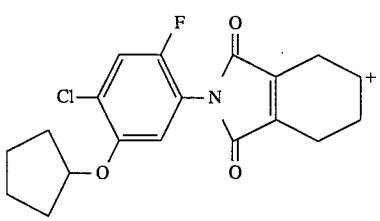

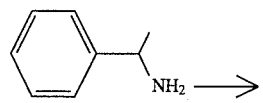

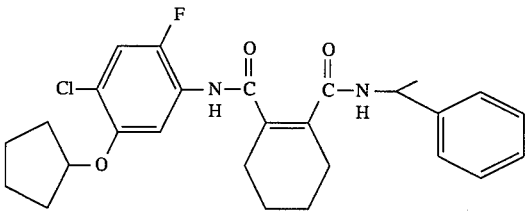

N-(2-Fluoro-4-chloro-5-cyclopentyloxyphenyl)- 3,4,5,6-tetrahydrophthalimide (1.00 g, 2.75 mmol), (±)- 1-phenylethylamine (0.433 g, 3.57 mmol), triethylamine (0.310 g, 3.06 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 1-phenylethyl)-3,4, 5,6-tetrahydrophthalamide as white crystals (1.069 g, 80.0% yield).

Melting point: 169°–171° C.

$^1$H-NMR(CDCl$_3$,TMS,ppm): δ1.35(3H,d,J=7.5Hz), 1.70(4H,m), 1.90(8H,m), 2.37(4H,m), 4.78(1H,m), 5.07(1H,dq, J=7.5 and 7.5Hz), 6.15(1H,d,J=7.5Hz), 7.12 (1H, d, $J_{HF}$=10.5Hz), 7.20(5H, s), 7.93 (1H, brs), 8.12(1H, d, $J_{HF}$=7.5Hz).

IR(KBr disk, cm$^{-1}$): 700, 870, 1200, 1258, 1410, 1490, 1520, 1622, 1640, 2950, 3300.

EXAMPLE 27

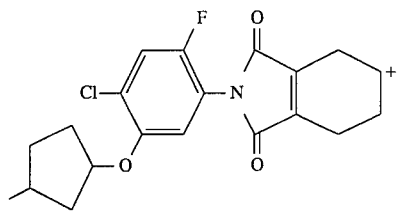

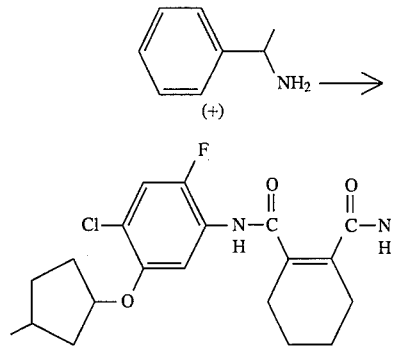

N-{2-Fluoro-4-chloro-5-(3-methylcyclopentyl)oxyphenyl}- 3,4,5,6-tetrahydrophthalimide (1.00 g, 2.65 mmol), R-(+)-1-phenylethylamine (0.530 g, 4.37 mmol), triethylamine (0.340 g, 0.470 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-{2-fluoro-4-chloro-5-(3-methylcyclopentyl)oxyphenyl}-N'-(1-phenylethyl)-3,4,5,6-tetrahydrophthalamide as white crystals (1.297 g, 98.1% yield).

Melting point: 176°–179° C.

$^1$H-NMR(CDCl$_3$,TMS,ppm): δ1.02 and 1.10(total 3H, each d, J=6.0 and 6.0Hz), 1.37 (3H, d, J=7.5Hz), 1.68(4H, m), 1.80–2.30(7H,m), 2.38(4H,m), 4.78(1H,m), 5.10(1H, dq,J=7.5 and 7.5Hz), 6.17(1H,d,J=7.5Hz), 7.13(1H, d,J$_{HF}$=10.5Hz), 7.31(5H,s), 8.00(1H,brs), 8.13 (1H, d, J$_{HF}$=7.5Hz).

IR(KBr disk, cm$^-$): 700, 1190, 1410, 1482, 1520, 1620, 1640, 2950, 3300.

EXAMPLE 28

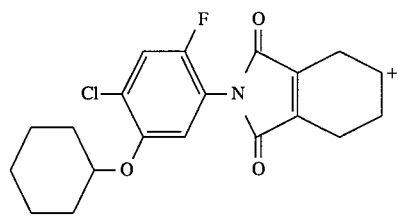

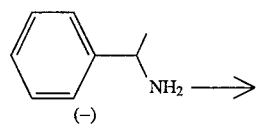

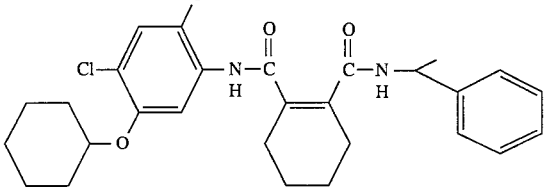

N-(2-Fluoro-4-chloro-5-cyclohexyloxyphenyl)-3,4,5,6-tetrahydrophthalimide (1.00 g, 2.65 mmol), R-(+)-1-phenylethylamine (0.65 g, 5.36 mmol), triethylamine (0.268 g, 2.65 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclohexyloxyphenyl)-N'-(1-phenylethyl)- 3,4,5,6-tetrahydrophthalamide as white crystals (1.09 g, 82.3% yield).

Melting point: 156°–159° C.

Optical Rotation: [α]$_D$=+34.69(c=0.980,CHCl$_3$,20° C.)

$^1$H-NMR(CDCl$_3$,TMS,ppm): δ1.37(3H,d,J=7.5Hz), 1.25–2.20(14H, m), 2.38(4H,m), 4.25(1H,m), 5.09(1H,dq, J=7.5 and 7.5Hz), 6.12(1H,d,J=7.5Hz), 7.04(1H,d, J$_{HF}$=10.5Hz), 7.20(5H,s), 7.92(1H,brs), 8.12(1H,d, J$_{HF}$=7.5Hz).

IR(KBr disk, cm$^{-1}$): 700, 1180, 1405, 1480, 1518, 1620, 1640, 2950, 3290.

EXAMPLE 29

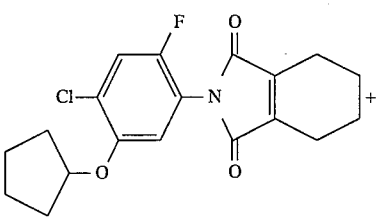

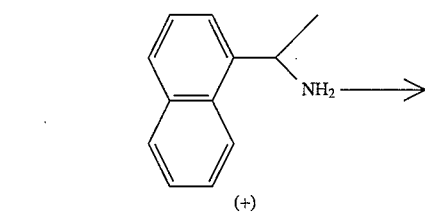

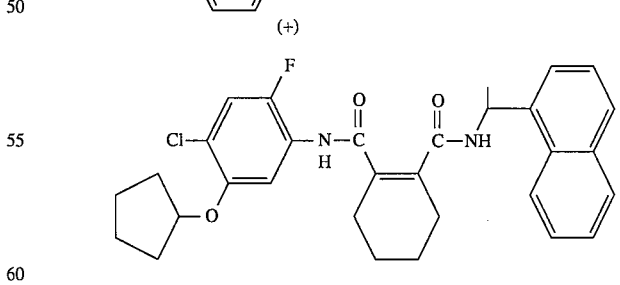

N-(2-Fluoro-4-chloro-5-cyclopentyloxyphenyl)- 3,4,5,6-tetrahydrophthalimide (1.00 9, 2.75 mmol), R-(+)-1 -(1-naphthyl)ethylamine (0.570 g, 3.33 mmol), triethylamine (0.310 g, 3.06 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-{1-(1-naphthyl)ethyl}-3,4,5,6-tetrahydrophthalamide as white crystals (0.950 9, 64.7% yield).

Melting point: 198°–201° C.

Optical Rotation: $[\alpha]_D$=−32.67(c=1.010,CHCl$_3$,20° C.)

$^1$H-NMR(CDCl$_3$/DMSO-d$_6$, TMS, ppm): δ1.48 (3H, d, J=7.5Hz), 1.67(4H,m), 1.83(8H,m), 2.33(4H,m), 4.63(1H, m), 5.77(1H,dq, J=7.5 and 7.5Hz), 7.01(1H,d, J$_{HF}$=10.5Hz), 7.20–8.20(8H,m), 9.10(1H,brs).

IR(KBr disk, cm$^{-1}$): 678, 770, 860, 1185, 1250, 1410, 1485, 1520, 1620, 1640, 2910, 3270.

EXAMPLE 30

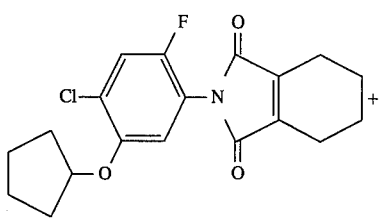

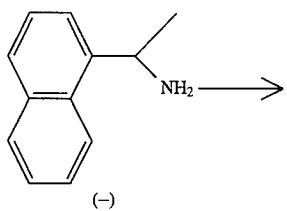

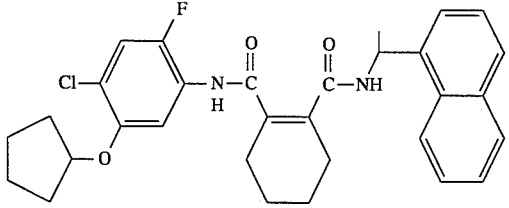

N-(2-Fluoro-4-chloro-5-cyclopentyloxyphenyl)- 3,4,5,6-tetrahydrophthalimide (1.00 g, 2.75 mmol), S-(−)-1 -(1-naphthyl)ethylamine (0.570 g, 3.33 mmol), triethylamine (0.310 g, 3.06 mmol) and benzene (25 ml) as a solvent were placed into a round bottom flask (50 cc) and stirred overnight at room temperature. After completion of the reaction, the solvent was distilled off under reduced pressure and the precipitated crystals were isolated by filtration. The crystals were washed with hexane and dried to obtain N-(2-fluoro-4-chloro-5-cyclopentyloxyphenyl)-N'-{1-(1-naphthyl)ethyl}-3,4,5,6-tetrahydrophthalamide as white crystals (0.410 g, 27.9% yield).

Melting point: 196°–199° C.

Optical Rotation: $[\alpha]_D$=+31.56(c=1.039,CHCl$_3$,20° C.)

$^1$H-NMR(CDCl$_3$,TMS,ppm): δ1.47(3H,d,J=7.5Hz), 1.67(4H,m), 1.80(8H,m), 2.30(4H,m), 4.65(1H,m), 5.77(1H,dq, J=7.5 and 7.5Hz), 7.00(1H, d, J$_{HF}$=10.5Hz), 7.15–8.20(8H,m), 9.08(1H,brs).

IR(KBr disk, cm$^{-1}$): 770, 860, 1190, 1410, 1480, 1520, 1620, 1640, 2920, 3260.

EXAMPLE 31

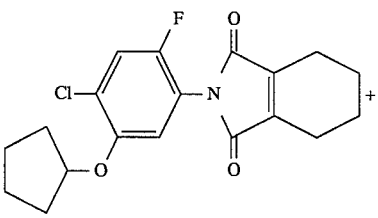

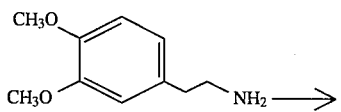

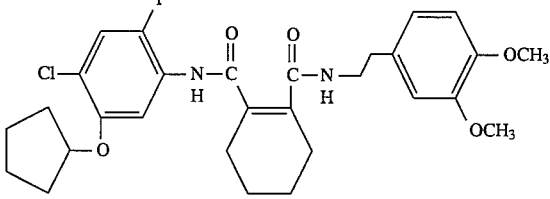

N-(2-Fluoro-4-chloro-5-cyclopentyloxyphenyl)- 3,4,5,6-tetrahydrophthalimide (1.00 g, 2.75 mmol), 2-(3,4-dimethoxyphenyl)ethylamine (0.600 g, 3.31 mmol), triethylamine (0.310 g, 3.06 mmol) and benzene (20. ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-{2-(3,4-dimethoxyphenyl)ethyl}-3,4,5,6-tetrahydrophthalamide as white crystals (1.16 g, 77.5% yield).

Melting point: 159°–161° C.

$^1$H-NMR(CDCl$_3$,TMS,ppm): δ1.70(4H,m), 1.88(8H,m), 2.38(4H,m), 2.62(2H,t,J=7.5Hz), 3.48(2H,dt,J=6.0 and 7.5Hz), 3.87(6H,s), 4.80(1H,m), 5.92(1H,brt, J=6.0Hz), 6.70(2H,m), 6.75(1H,dt,J=9.0Hz), 7.17(1H, d,J$_{HF}$=10.5Hz), 8.10(1H,brs), 8.18(1H,d,J$_{HF}$=7.5Hz).

IR(KBr disk, cm$^{-1}$): 1122, 1200, 1260, 1415, 1490, 1520, 1620, 2950, 3195.

EXAMPLE 32

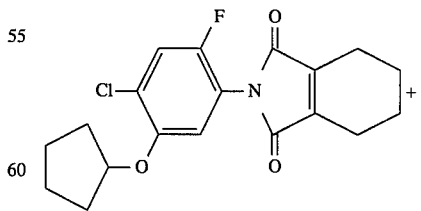

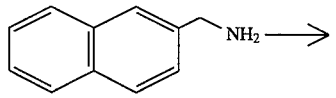

35
-continued

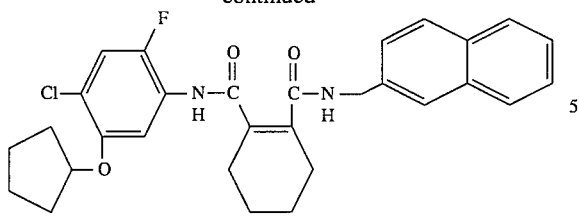

N-(2-Fluoro-4-chloro-5-cyclopentyloxyphenyl)- 3,4,5,6-tetrahydrophthalimide (0.800 g, 2.20 mmol), 2-aminomethylnaphthalene (0.380 g, 2.42 mmol), triethylamine (0.240 g, 2.37 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(2-naphthylmethyl)-3,4,5,6-tetrahydrophthalamide as white crystals (0.200 g, 17.5% yield).

Melting point: 174°–175° C.

$^1$H-NMR(CDCl$_3$,TMS,ppm): δ1.77(12H,m), 2.37(4H,m), 4.48(2H,d, J=7.0Hz), 6.27(1H,m), 6.86(1H,d, J$_{HF}$=10.5Hz), 7.2–8.1(9H,m).

IR(KBr disk, cm$^{-1}$): 858, 1182, 1405, 1480, 1520, 1620, 1640, 2925, 3250.

EXAMPLE 33

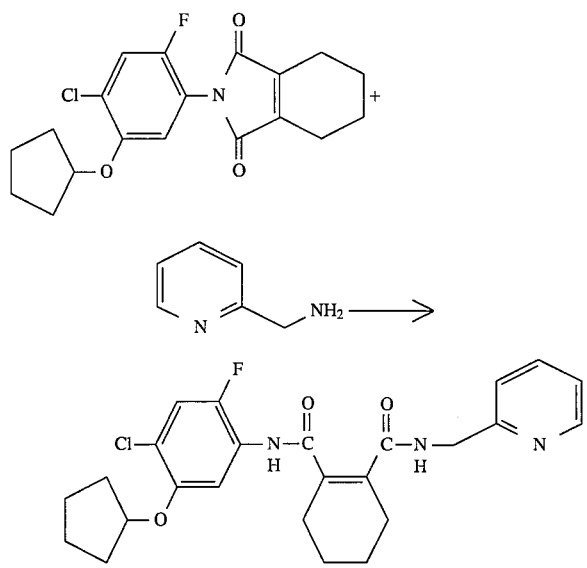

N-(2-Fluoro-4-chloro-5-cyclopentyloxyphenyl)- 3,4,5,6-tetrahydrophthalimide (2.00 g, 5.50 mmol), 2-(aminomethyl)pyridine (0.710 g, 6.57 mmol), triethylamine (0.610 g, 6.03 mmol) and benzene (40 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 2-pyridyl)methyl-3,4,5,6-tetrahydrophthalamide as white crystals (1.410 g, 54.2% yield).

36

Melting point: 144°–148° C.

$^1$H-NMR(CDCl$_3$,TMS,ppm): δ1.40–2.0(12H,m), 2.42(4H,m), 4.52(2H,d,J=6.0Hz), 4.69(1H,m), 7.03(1H,d, J$_{HF}$=10.5Hz), 7.30(2H,m), 7.50(1H,m), 7.97(1H, brs), 7.98(1H,d,J$_{HF}$=7.5Hz), 8.43(1H,d,J=4.5Hz).

IR(KBr disk, cm$^{-1}$): 750, 850, 1190, 1240, 1400, 1480, 1520, 1640, 2925, 3300.

EXAMPLE 34

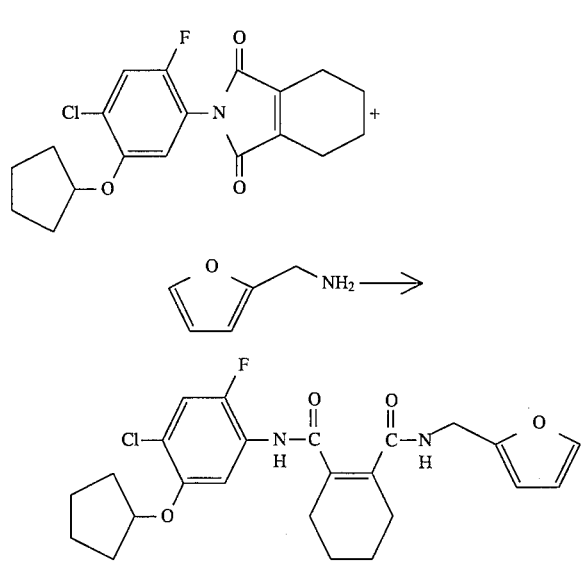

N-(2-Fluoro-4-chloro-5-cyclopentyloxyphenyl)- 3,4,5,6-tetrahydrophthalimide (1.00 g, 2.75 mmol), furfurylamine (0.320 g, 3.29 mmol), and acetonitrile (25 ml) as a solvent were placed into a round bottom flask (50 cc) and stirred for 2 hours at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-furfuryl-3,4,5,6-tetrahydrophthalamide as light brown crystals (0.860 g, 68.0% yield).

Melting point: 152°–153° C.

$^1$H-NMR(CDCl$_3$,TMS,ppm): δ1.68(4H,m), 1.85(8H,m), 2.36 (4H,m), 4.27(2H,d,J=6.0Hz), 4.63(1H,m), 5.98(2H, brs), 6.15(1H,m), 6.92(1H,brs), 6.95(1H,d, J$_{HF}$=10.5Hz), 7.78(1H,brs), 7.97(1H,d,J$_{HF}$=7.5Hz).

IR(KBr disk, cm$^{-1}$): 1190, 1260, 1410, 1520, 1640, 2950, 3290.

EXAMPLE 35

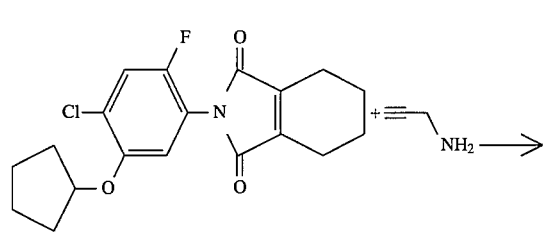

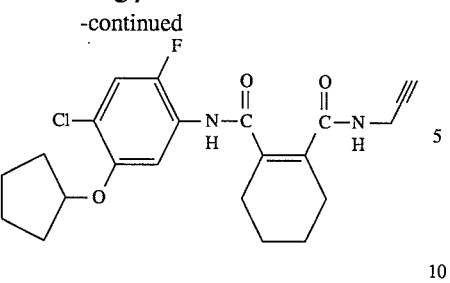

N-(2-Fluoro-4-chloro-5-cyclopentyloxyphenyl)- 3,4,5,6-tetrahydrophthalimide (1.00 g, 2.75 mmol), propargylamine (0.180 g, 3.27 mmol), and benzene (25 ml) as a solvent were placed into a round bottom flask (50 cc) and stirred overnight at room temperature. After completion of the reaction, the solvent was distilled off under reduced pressure, and the resulting crude product was recrystallized from chloroform/hexane to obtain N-(2 -fluoro-4-chloro-5-cyclopentyloxyphenyl)-N'-propargyl- 3,4,5,6-tetrahydrophthalamide as white crystals (0.366 g, 31.8% yield).

Melting point: 153°–156° C.

$^1$H-NMR(CDCl$_3$/DMSO-d$_6$,TMS,ppm): δ1.70(4H,m), 1.85(8H,m), 2.00(1H,t,J=3.0Hz), 2.38(4H,m), 3.97(2H,dd, J=3.0 and 5.0Hz), 4.78(1H,m), 7.11(1H,d,J$_{HF}$=10.5Hz), 7.38(1H,m), 8.10(1H,d,J$_{HF}$=7.5Hz, 8.53(1H,brs).

IR(KBr disk, cm$^{-1}$): 630, 660, 865, 1190, 1250, 1290, 1410, 1490, 1520, 1642, 2950, 3300.

EXAMPLE 36

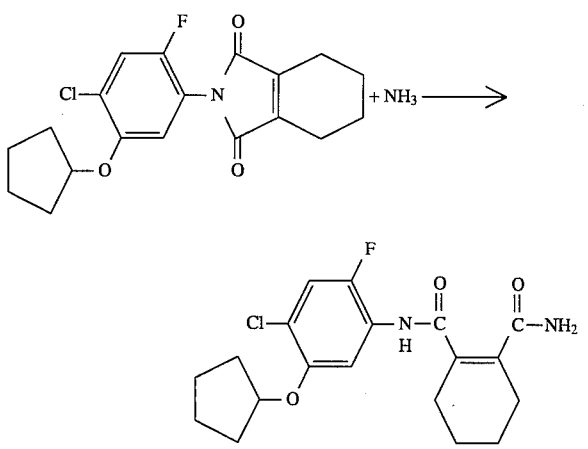

N-(2-Fluoro-4-chloro-5-cyclopentyloxyphenyl)- 3,4,5,6-tetrahydrophthalimide (1.00 g, 2.75 mmol) and tetrahydrofuran (20 ml) as a solvent were placed into a round bottom flask (50 cc), and an excess amount of 25% aqueous ammonia was poured into the mixture, followed by stirring for one hour at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)- 3,4,5,6-tetrahydrophthalamide as white crystals (0.400 g, 38.2% yield).

Melting point: 200°–201° C.

$^1$H-NMR(CDCl$_3$+DMSO-d$_6$, TMS, ppm): δ1.65–1.82 (12H, m), 2.34(4H,m), 2.54(2H,brs), 4.69(1H,m), 7.00(1H, d, J$_{HF}$=10.5Hz), 7.95(1H,d,J$_{HF}$=7.5Hz), 8.60(1H,brs).

IR(KBr disk, cm$^{-1}$): 870, 960, 1160, 1190, 1240, 1260, 1280, 1390, 1520, 1610, 1640, 2950, 3300, 3450.

EXAMPLE 37

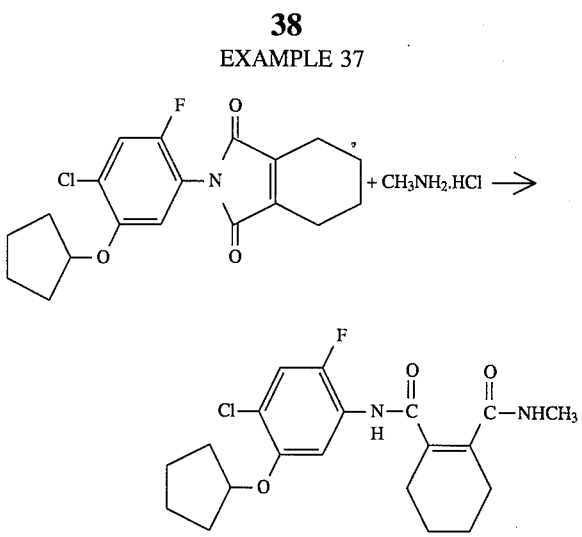

Methylamine hydrochloride (1.70 g, 24.8 mmol) and potassium carbonate (1.70 g, 12.3 mmol), and acetonitrile (5 ml) as a solvent were placed into a round bottom flask (100 cc), followed by stirring at room temperature. After confirming the generation of carbon dioxide gas, N-(2 -fluoro-4-chloro-5-cyclopentyloxyphenyl)-3,4,5,6-tetrahydrophthalimide (5.88 g, 16.2 mmol) was added thereto, followed by stirring at room temperature for 4 hours. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-methyl- 3,4,5,6-tetrahydrophthalamide as white crystals (4.79 g, 74.9% yield).

Melting point: 179°–180° C.

$^1$H-NMR(CDCl$_3$, TMS, ppm): δ1.68(4H,m), 1.87(8H,m), 2.35 (4H,m), 2.71(3H,d,J=5.4Hz), 4.77(1H,m), 5.89(1H, brs), 7.08(1H,d,J$_{HF}$=10.5Hz), 7.97(1H,brs), 7.98(1H, d, J$_{HF}$=7.5Hz).

IR(KBr disk, cm$^{-1}$): 868, 1174, 1196, 1244, 1418, 1490, 1532, 1550, 1616, 1650, 1684, 2950, 3310.

EXAMPLE 38

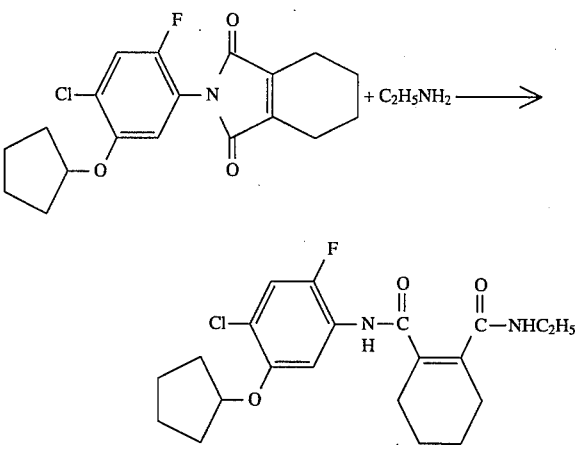

N-(2-Fluoro-4-chloro-5-cyclopentyloxyphenyl)- 3,4,5,6-tetrahydrophthalimide (0.500 g, 1.37 mmol), and benzene (30 ml) as a solvent were placed into a round bottom flask (50 cc) and, after blowing ethylamine (0.900 g, 20.0 mmol)

thereinto, the mixture was stirred at room temperature for 1 hour. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-ethyl- 3,4,5,6-tetrahydrophthalamide as white crystals (0.390 g, 69.4% yield).

Melting point: 187°–189° C.

$^1$H-NMR(CDCl$_3$,TMS,ppm): δ1.00(3H,t,J=7.5Hz), 1.67(4H,m), 1.85(8H,m), 2.33(4H,m), 3.20(2H,dq,J=3.0 and 6.0Hz), 4.72(1H,m), 5.82(1H,brt,J=3.0Hz), 7.01(1H, d,J$_{HF}$=9.0Hz), 7.89(1H,brs), 8.02(1H,d,J$_{HF}$=7.5Hz).

IR(KBr disk, cm$^{-1}$): 860, 1190, 1250, 1410, 1480, 1520, 1600, 1620, 1640, 1670, 2925, 3300.

EXAMPLE 39

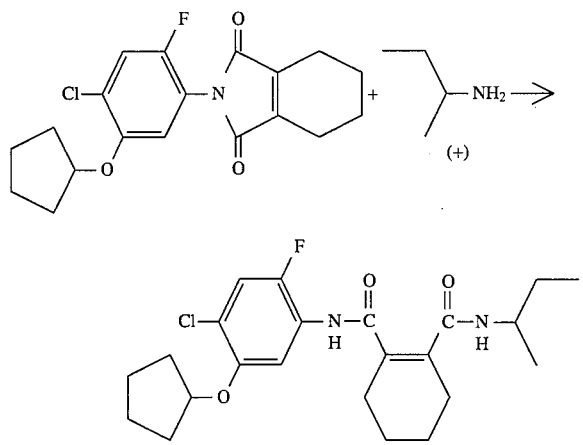

N-(2-Fluoro-4-chloro-5-cyclopentyloxyphenyl)- 3,4,5,6-tetrahydrophthalimide (0.900 g, 2.47 mmol), S-(+)-sec-butylamine (0.235 g, 3.21 mmol), N-methylmorpholine (0.270 g, 2.67 mmol) and benzene (25 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(sec-butyl)- 3,4,5,6-tetrahydrophthalamide as white crystals (0.300 9, 27.8% yield).

Melting point: 174°–175° C.

400MHz $^1$H-NMR (CDCl$_3$,TMS,ppm): δ0.77 and 0.91(total 3H, each t,J=7.4 and 7.3Hz), 1.00 and 1.17(total 3H, each d,J=6.6 and 6.6Hz), 1.35 and 1.52(total 2H, each qui,J=7.3 and 7.3Hz), 1.62(2H,m), 1.71(4H,m), 1.88(6H,m), 2.39(4H,m), 4.78 and 4.83(total 1H, each m), 5.60 and 6.02(total 1H, each gd,J$_{HF}$=10.2 and 10.2Hz), 7.99(total 1H,brs), 8.15 and 8.24(total 1H, each d, J$_{HF}$=7.2 and 7.1Hz), 9.09(1H,brs).

IR (KBr disk, cm$^{-1}$): 680, 860, 1190, 1250, 1410, 1490, 1520, 1600, 1620, 1640, 1670, 2950, 2975, 3275.

EXAMPLE 40

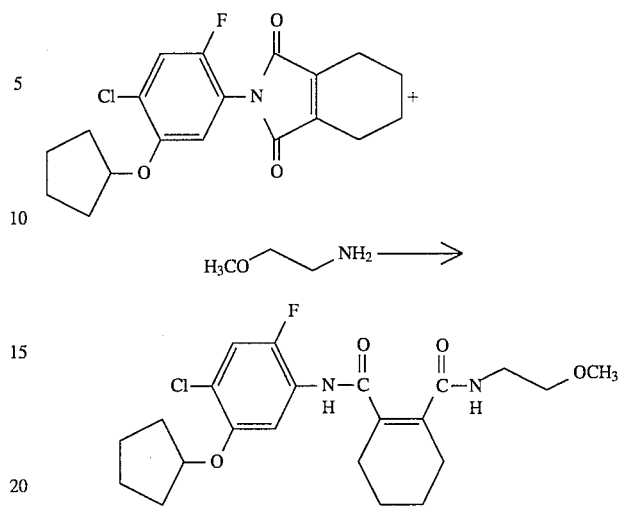

N-(2-Fluoro-4-chloro-5-cyclopentyloxyphenyl)- 3,4,5,6-tetrahydrophthalimide (0.500 g, 1.37 mmol), 2-methoxyethylamine (0.118 g, 1.57 mmol), and benzene (15 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 2-methoxyethyl)-3,4,5,6-tetrahydrophthalamide as white crystals (0.232 g, 38.6% yield).

Melting point: 151°–151.5° C.

400MHz $^1$H-NMR (CDCl$_3$,TMS,ppm): 61.64(4H,m), 1.71(2H,m), 1.85(2H,m), 1.89(4H,m), 2.38(2H,m), 2.41(2H,m), 3.20(3H,s), 3.31(2H,t,J=5.2Hz), 3.40(2H,dt,J= 5.2 and 5.2Hz), 4.80(1H,m), 6.15(1H,t,J=5.2Hz), 7.11(1H, d,J$_{HF}$=10.2Hz), 7.96(1H,brs), 8.13(1H,d,J$_{HF}$=7.2Hz).

IR (KBr disk, cm$^{-1}$): 860, 1125, 1196, 1250, 1412, 1488, 1518, 1604, 1630, 1644, 1670, 2950, 3280.

EXAMPLE 41

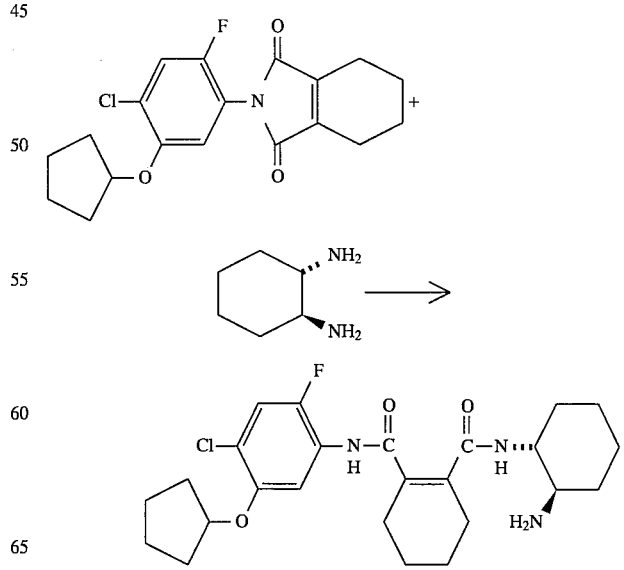

N-(2-Fluoro-4-chloro-5-cyclopentyloxyphenyl)- 3,4,5,6-tetrahydrophthalimide (0.900 g, 2.47 mmol), (DL)-trans-1, 2-diaminocyclohexane (0.282 g, 2.47 mmol), triethylamine (0.250 g, 2.47 mmol) and benzene (20 ml) as a solvent were placed into a round bottom flask (50 cc) and stirred overnight at room temperature. After completion of the reaction, the resulting crude product was recrystallized from hexane to obtain N-(2-fluoro-4-chloro-5-cyclopentyloxyphenyl)-N'-( 2-aminocyclohexyl)-3,4,5,6-tetrahydrophthalamide as white crystals (0.340 g, 28.8% yield).

Melting point: 143°–146° C.

400MHz $^1$H-NMR (CDCl$_3$,TMS,ppm): δ1.02(1H,m), 1.23(4H,m), 1.55(4H,m), 1.62(6H,m), 1.72(6H,m), 2.35(6H,m), 3.25 and 3.47(total 1H,each dr,J=4.3 and 11.1Hz, J=4.1 and 15.0Hz), 4.78(1H,m), 5.84(1H,d,J= 8.51Hz), 7.11(1H,d,J$_{HF}$=10.2Hz), 8.02(1H,brs), 8.07 and 8.12(total 1H, each d,J$_{HF}$=7.5 and 7.2Hz).

IR (KBr disk, cm$^{-1}$): 680, 870, 1190, 1250, 1290, 1330, 1360, 1400, 1410, 1450, 1500, 1550, 1620, 1650, 2900, 2950, 3250, 3300.

EXAMPLE 42

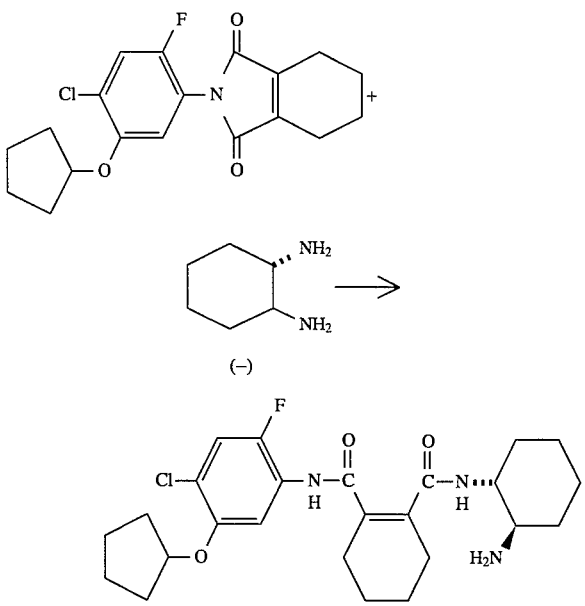

N-(2-Fluoro-4-chloro-5-cyclopentyloxyphenyl)- 3,4,5,6-tetrahydrophthalimide (1.00 g, 2.75 mmol), (–)-R,R- 1,2-diaminocyclohexane (0.314 g, 2.75 mmol), triethylamine (0.306 g, 3.06 mmol) and benzene (30 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 2-aminocyclohexyl)-3,4,5,6-tetrahydrophthalamide as white crystals (0.110 g, 8.4% yield).

Melting point: 143°–145° C.

$^1$H-NMR (CDCl$_3$,TMS,ppm): δ1.12–1.42(8H,m), 1.72(4H,m), 1.85(8H,m), 2.38(6H,m), 3.47(1H,d,J=9.0Hz), 4.79(1H,m), 5.87(1H,brd,J=9.0Hz), 7.13(1H,d, J$_{HF}$=10.5Hz), 8.12(1H,brs), 8.15(1H,d, J$_{HF}$=7.5Hz).

IR (KBr disk, cm$^{-1}$): 600, 860, 1190, 1250, 1360, 1410, 1480, 1510, 1550, 1620, 1640, 1670, 2850, 2950, 3300, 3350.

EXAMPLE 43

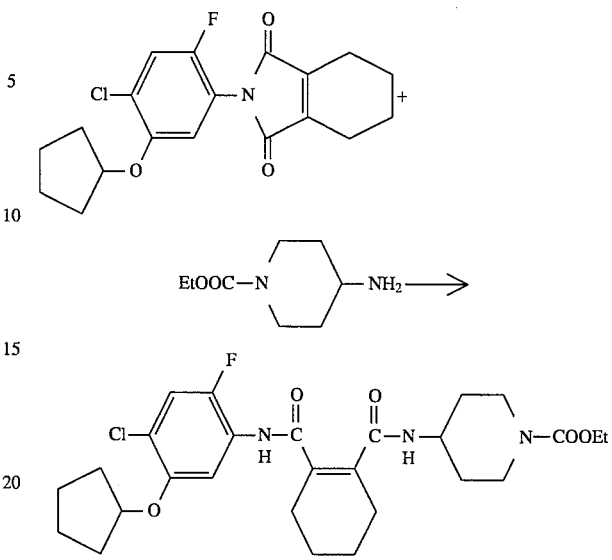

N-(2-Fluoro-4-chloro-5-cyclopentyloxyphenyl)- 3,4,5,6-tetrahydrophthalimide (1.00 g, 2.75 mmol), ethyl 4-amino-1-piperidinecarboxylate (0.620 g, 3.60 mmol), triethylamine (0.310 g, 3.06 mmol) and benzene (25 ml) as a solvent were placed into a round bottom flask (50 cc) and stirred overnight at room temperature. After completion of the reaction, the solvent was distilled off under reduced pressure, and the resulting crude product was recrystallized from ether to obtain N-(2-fluoro-4-chloro-5 -cyclopentyloxyphenyl)-N'-(1-ethoxycarbonyl-4-piperidyl)- 3,4,5,6-tetrahydrophthalamide as white crystals (0.732 g, 50.9% yield).

Melting point: 194°–196° C.

400MHz $^1$H-NMR (CDCl$_3$,TMS,ppm): δ1.23(3H,t,J=7.1Hz), 1.63(2H,m), 1.17–1.77(7H,m), 1.81–1.96(7H,m), 2.38(4H,brd, J=6.9Hz), 2.85 and 2.96(total 2H, each dt, J=2.7 and 12.1Hz, J=3.1 and 11.1Hz), 3.86–3.96(3H,m), 4.09 and 4.12(2H,each q,J=7.1 and 7.1Hz), 4.78(1H,m), 5.76(1H,d,J=5.8Hz), 7.12(1H,d,J$_{HF}$=10.2Hz), 7.78 and 7.84(1H, each brs), 8.11 and 8.21 (1H, each d, J$_{HF}$=7.2 and 7.1Hz).

IR (KBr disk, cm$^{-1}$): 1140, 1180, 1220, 1240, 1310, 1400, 1430, 1480, 1510, 1620, 1630, 1690, 2900, 3250.

EXAMPLE 44

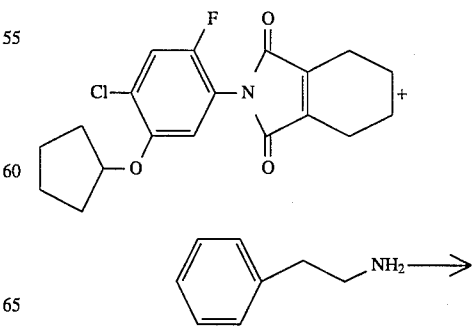

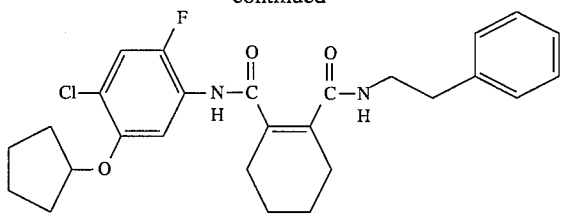

N-(2-Fluoro-4-chloro-5-cyclopentyloxyphenyl)- 3,4,5,6-tetrahydrophthalimide (1.00 g, 2.75 mmol), β-phenylethylamine (0.333 g, 2.75 mmol), and benzene (8 ml)/hexane (12 ml) as a solvent were placed into a round bottom flask (50 cc) and stirred for 30 minutes at room temperature. After completion of the reaction, the solvent was distilled off under reduced pressure, and the precipitated crystals were isolated by filtration. The crystals were washed with hexane and dried to obtain N-(2 -fluoro-4-chloro-5-cyclopentyloxyphenyl)-N'-(2-phenylethyl)- 3,4,5,6-tetrahydrophthalamide as white crystals (0.840 g, 62.9% yield).

Melting point: 165°–166° C.

$^1$H-NMR (CDCl$_3$,TMS,ppm): δ1.65(4H,m), 1.85(8H,m), 2.31(4H, m), 2.64(2H,t,J=6.0Hz), 3.43(2H,q,J=6.0Hz), 4.65(1H,m), 5.74(1H,brt,J=6.0Hz), 6.96–7.16(6H, m), 7.95(1H,brs), 8.02(1H,d,J$_{HF}$=7.5Hz).

IR (KBr disk, cm$^{-1}$): 690, 860, 1190, 1250, 1410, 1480, 1520, 1540, 1600, 1620, 1640, 2950, 3275.

EXAMPLE 45

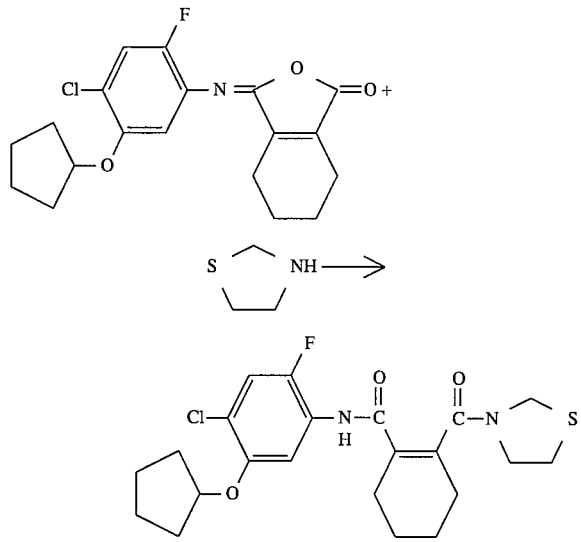

N-(2-Fluoro-4-chloro-5-cyclopentyloxyphenyl)- 3,4,5,6-tetrahydroisophthalimide (1.00 g, 2.75 mmol), thiazolidine (0.245 g, 2.75 mmol), triethylamine (4 drops) and benzene (15 ml)/hexane (10 ml) as a solvent were placed into a round bottom flask (50 cc) and stirred overnight at room temperature. After completion of the reaction, the solvent was distilled off under reduced pressure, and the precipitated crude product was recrystallized from ether/hexane to obtain N-(2-fluoro-4-chloro-5-cyclopentyloxyphenyl)- 2-thiazolinocarbonyl-1-cyclohexene-1-carboxylic acid amide as white crystals (0.365 g, 29.3% yield).

Melting point: 135°–136° C.

400MHz $^1$H-NMR (CDCl$_3$,TMS,ppm): δ1.69(2H,m), 1.75(4H,m), 1.89 (6H,m), 2.35 and 2.45 (total 2H, each s), 2.96(2H,m), 3.68(1H, t,J=6.2Hz), 3.81(1H,t, J=6.5Hz), 4.40(1H, s), 4.55(1H,s), 4.79(1H,m), 7.10 and 7.15(1H,each d,J$_{HF}$=10.3 and 9.7Hz), 8.00 (1H, d, J$_{HF}$=7.2Hz), 8.03 (1H, brs).

IR (KBr disk, cm$^{-1}$): 875, 1170, 1195, 1240, 1410, 1490, 1530, 1620, 1640, 1675, 2950, 3350.

EXAMPLE 46

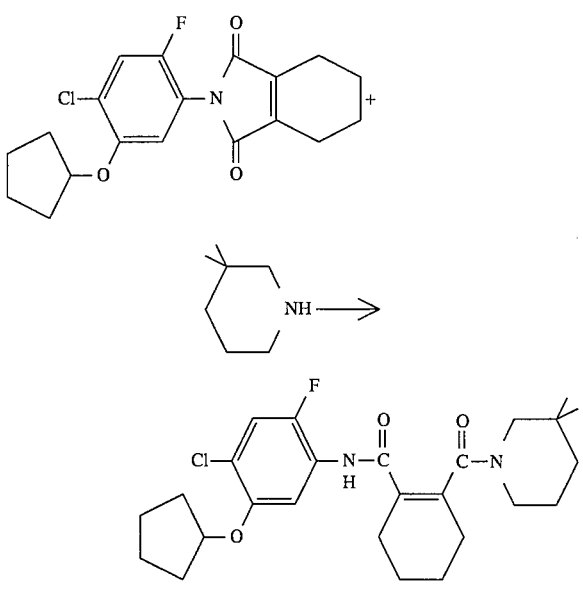

N-(2-Fluoro-4-chloro-5-cyclopentyloxyphenyl)- 3,4,5,6-tetrahydrophthalimide (1.50 g, 4.12 mmol), 3,3-dimethylpiperidine (0.513 g, 4.53 mmol), triethylamine (0.542 g, 5.36 mmol) and benzene (50 ml)/hexane (10 ml) as a solvent were placed into a round bottom flask (100 cc) and stirred for overnight at-room temperature. After completion of the reaction, the solvent was distilled off under reduced pressure, and the precipitated crude product was recrystallized from ether/hexane to obtain N-(2-fluoro-4-chloro- 5-cyclopentyloxyphenyl)-N',N'-(2,2-dimethylpentamethylene)- 3,4,5,6-tetrahydrophthalaimide as white crystals (1.30 g, 66.3% yield).

Melting point: 115°–117° C.

400MHz $^1$H-NMR (CDCl$_3$, TMS, pp): δ0. 825 (6H, d, J=6.0Hz), 1.75–1.85(16H,m), 2.28(4H,m), 2.94(1H, s), 3.27(2H, m), 3.50(1H,m), 4.75(1H,m), 7.09 and 7.11(total 1H, each d, J$_{HF}$=10.2 and 10.1Hz), 8.07 and 8.16(total 1H, each d, J$_{HF}$=7.2 and 7.2Hz), 8.59 and 8.63 (total 1H, each brs).

IR (KBr disk, cm$^{-1}$): 860, 1190, 1240, 1280, 1410, 1440, 1490, 1520, 1610, 1670, 2850, 2925.

EXAMPLE 47

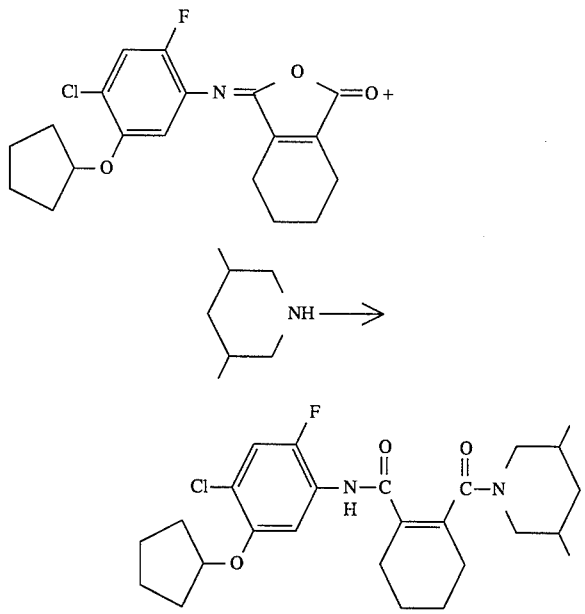

N-(2-Fluoro-4-chloro-5-cyclopentyloxyphenyl)- 3,4,5,6-tetrahydroisophthalimide (1.00 g, 2.75 mmol), 3,5-dimethylpiperidine (0.311 g, 2.75 mmol) and benzene (25 ml) as a solvent were placed into a round bottom flask (50 cc) and stirred for 15 minutes at room temperature. After completion of the reaction, the solvent was distilled off under reduced pressure, and the resulting crude product was recrystallized from hexane to obtain N-(2-fluoro-4-chloro-5-cyclopentyloxyphenyl)-N',N'-( 3,5-dimethylpentamethylene)- 3,4,5,6-tetrahydrophthalamide as white crystals (0.806 g, 61.5% yield).

Melting point: 134°–136° C.

400MHz $^1$H-NMR (CDCl$_3$, TMS, pp): δ0.71 (1H, qui, J=12.3Hz), 0.85(6H,d,J=6.5Hz), 1.47(1H,brs), 1.62–1.65(2H,m), 1.74(4H,m), 1.85 and 1.89(total 7H,each m), 2.01(1H, t,J=12.4 and 12.1Hz), 2.48(1H, t,J=12.5 and 12.2), 2.10–2.70(5H,m), 3.57(1H,dt,J=13.0 and 2.1Hz), 4.53 (1H,dt,J=12.9 and 2.0Hz), 4.79(1H,m), 7.10(1H,d, J$_{HF}$= 10.1Hz), 8.07(1H,d,J$_{HF}$=7.2Hz), 8.43(1H,brs).

IR (KBr disk, cm$^{-1}$): 670, 700, 845, 1160, 1190, 1235, 1250, 1400, 1430, 1480, 1510, 1600, 1660, 2925, 3025, 3300.

EXAMPLE 48

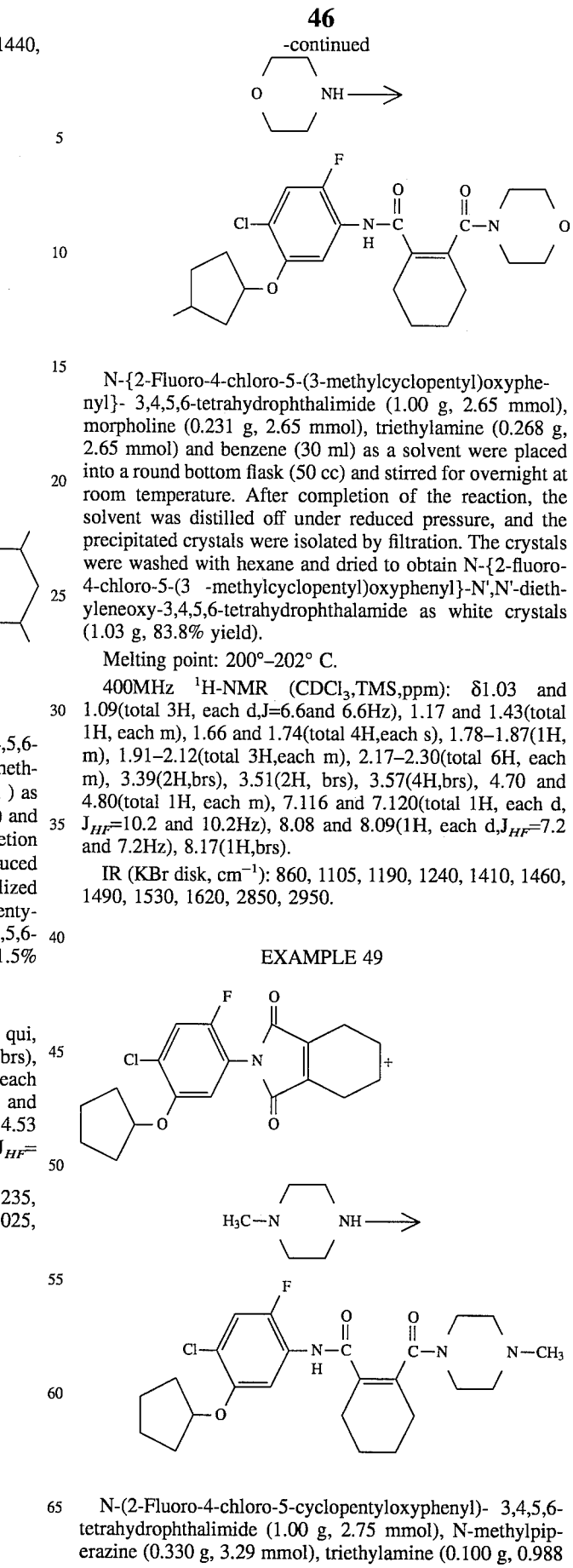

N-{2-Fluoro-4-chloro-5-(3-methylcyclopentyl)oxyphenyl}- 3,4,5,6-tetrahydrophthalimide (1.00 g, 2.65 mmol), morpholine (0.231 g, 2.65 mmol), triethylamine (0.268 g, 2.65 mmol) and benzene (30 ml) as a solvent were placed into a round bottom flask (50 cc) and stirred for overnight at room temperature. After completion of the reaction, the solvent was distilled off under reduced pressure, and the precipitated crystals were isolated by filtration. The crystals were washed with hexane and dried to obtain N-{2-fluoro-4-chloro-5-(3 -methylcyclopentyl)oxyphenyl}-N',N'-diethyleneoxy-3,4,5,6-tetrahydrophthalamide as white crystals (1.03 g, 83.8% yield).

Melting point: 200°–202° C.

400MHz $^1$H-NMR (CDCl$_3$,TMS,ppm): δ1.03 and 1.09(total 3H, each d,J=6.6and 6.6Hz), 1.17 and 1.43(total 1H, each m), 1.66 and 1.74(total 4H,each s), 1.78–1.87(1H, m), 1.91–2.12(total 3H,each m), 2.17–2.30(total 6H, each m), 3.39(2H,brs), 3.51(2H, brs), 3.57(4H,brs), 4.70 and 4.80(total 1H, each m), 7.116 and 7.120(total 1H, each d, J$_{HF}$=10.2 and 10.2Hz), 8.08 and 8.09(1H, each d,J$_{HF}$=7.2 and 7.2Hz), 8.17(1H,brs).

IR (KBr disk, cm$^{-1}$): 860, 1105, 1190, 1240, 1410, 1460, 1490, 1530, 1620, 2850, 2950.

EXAMPLE 49

N-(2-Fluoro-4-chloro-5-cyclopentyloxyphenyl)- 3,4,5,6-tetrahydrophthalimide (1.00 g, 2.75 mmol), N-methylpiperazine (0.330 g, 3.29 mmol), triethylamine (0.100 g, 0.988 mmol) and benzene (10 ml) as a solvent were placed into a round bottom flask (50 cc) and stirred overnight at room temperature. After completion of the reaction, the solvent was distilled off under reduced pressure, and the resulting crystals were isolated by filtration. The crystals were washed with hexane and thoroughly dried to obtain N-(2-fluoro-4-chloro-5 -cyclopentyloxyphenyl)-N',N'-(N''-methyldiethyleneimino)-3,4,5,6 -tetrahydrophthalamide as white crystals (0.907 g, 71.1% yield).

Melting point: 115°–116° C.

400MHz $^1$H-NMR (CDCl$_3$,TMS,ppm): δ1.62(2H,), 1.74(4H,m), 1.85(2H,m), 1.89(4H,m), 2.18(3H,S), 2.30(8H, m), 3.40(2H,m), 3.59(2H,m), 4.79(1H,m), 7.11(1H,d, $J_{HF}$=10.1Hz), 8.14 (1H, d, $J_{HF}$=7.2Hz), 8.30 (1H, brs).

IR (KBr disk, cm$^{-1}$): 830, 1000, 1022, 1141, 1170, 1198, 1240, 1256, 1274, 1292, 1384, 1434, 1442, 1460, 1484, 1500, 1518, 1602, 1650, 1682, 2810, 2890, 2950, 3260.

EXAMPLE 50

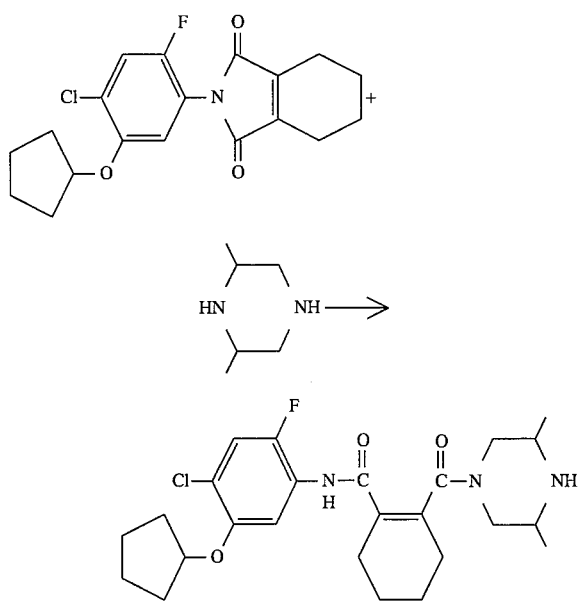

N-(2-Fluoro-4-chloro-5-cyclopentyloxyphenyl)- 3,4,5,6-tetrahydrophthalimide (1.00 g, 2.75 mmol), 2,6 -dimethylpiperazine (cis/trans, 0.377 g, 3.30 mmol), triethylamine (0.330 g, 3.26 mmol), and benzene (20 ml)/hexane (20 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5 -cyclopentyloxyphenyl)-N', N'-{bis(2-methylethylene)imino}- 3,4,5,6-tetrahydrophthalamide as white crystals (0.640 g, 48.7% yield).

Melting point: 115°–116° C.

400MHz $^1$H-NMR (CDCl$_3$, TMS, ppm): δ1.03(6H, brd, J=1.7Hz), 1.56–1.69(3H,m), 1.74(4H,brs), 1.89(6H,m), 2.18(2H,t,J=11.7Hz), 2.39–2.59(4H,brs), 2.62(2H, t,J= 11.1Hz), 3.49(1H,d,J=11.0Hz), 4.44 and 4.46(total 1H,d, $J_{HF}$=11.7Hz), 4.79(1H,m), 7.10(1H, d,$J_{HF}$=10.1Hz), 8.09(1H,d, $J_{HF}$=6.8Hz), 8.35(1H,brs).

IR (KBr disk, cm$^{-1}$): 700, 810, 860, 890, 1040, 1080, 1170, 1190, 1240, 1320, 1360, 1410, 1440, 1520, 1610, 1670, 2850, 2950, 3350.

EXAMPLE 51

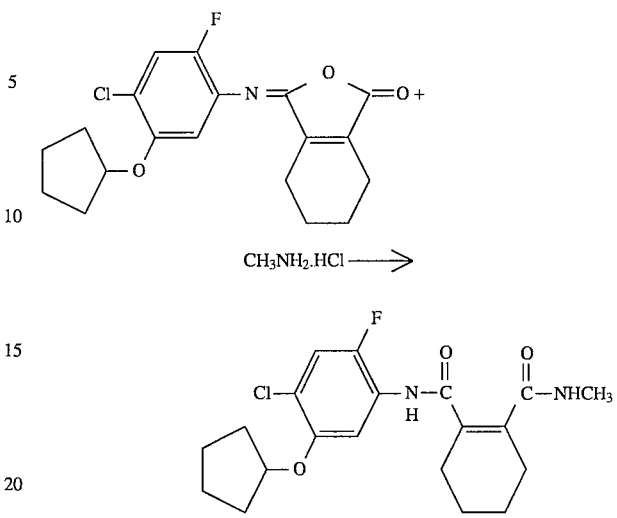

Methylamine hydrochloride (0.200 g, 2.96 mmol) and potassium carbonate (0.400 g, 2.89 mmol), and acetonitrile (5 ml) as a solvent were placed into a round bottom flask (25 cc), followed by stirring at room temperature. After confirming the generation of carbon dioxide gas, N-(2 -fluoro-4-chloro-5-cyclopentyloxyphenyl)-3,4,5,6-tetrahydroisophthalimide (0.650 g, 1.79 mmol) was added thereto, followed by stirring overnight at room temperature. After completion of the reaction, the reaction mixture was poured into 1N hydrochloric acid (20 ml), and the mixture was extracted with ethyl acetate (40 ml×3 portions). After drying the organic layer over anhydrous magnesium sulfate, the drying agent was removed, and the solvent was distilled off under reduced pressure. The precipitated crystals were isolated by filtration, thoroughly washed with hexane and dried to obtain N-(2-fluoro-4-chloro-5-cyclopentyloxyphenyl)-N'-methyl- 3,4,5,6-tetrahydrophthalamide as white crystals (0.380 g, 53.8% yield). The melting point and the spectral data thereof are shown in Example 37.

EXAMPLE 52

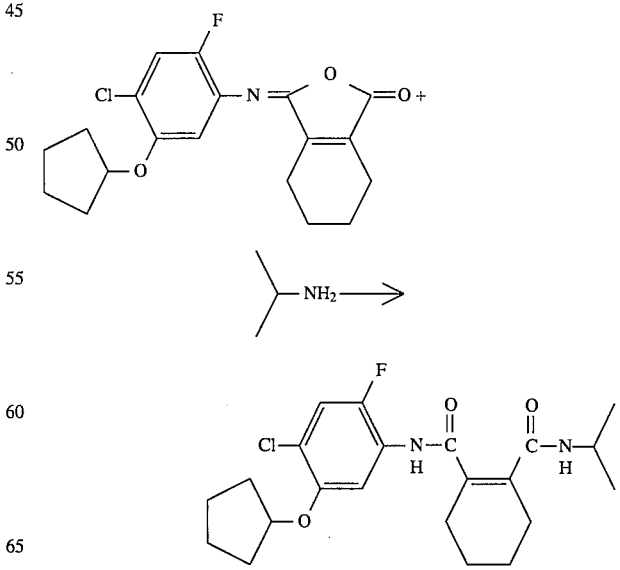

N-(2-Fluoro-4-chloro-5-cyclopentyloxyphenyl)- 3,4,5,6-tetrahydroisophthalimide (1.00 g, 2.75 mmol), isopropylamine (0.190 g, 3.21 mmol), triethylamine (0.280 g, 2.77 mmol), and benzene (20 ml) as a solvent were placed into a round bottom flask (50 cc) and stirred overnight at room temperature. After completion of the reaction, the solvent was distilled off under reduced pressure and the resulting crystals were isolated by filtration. The crystals were washed with hexane and thoroughly dried to obtain N-(2-fluoro-4-chloro-5 -cyclopentyloxyphenyl)-N'-isopropyl-3,4,5,6-tetrahydrophthalamide as white crystals (0.892 g, 76.7% yield). The melting point and the spectral data thereof are shown in Example 2.

EXAMPLE 53

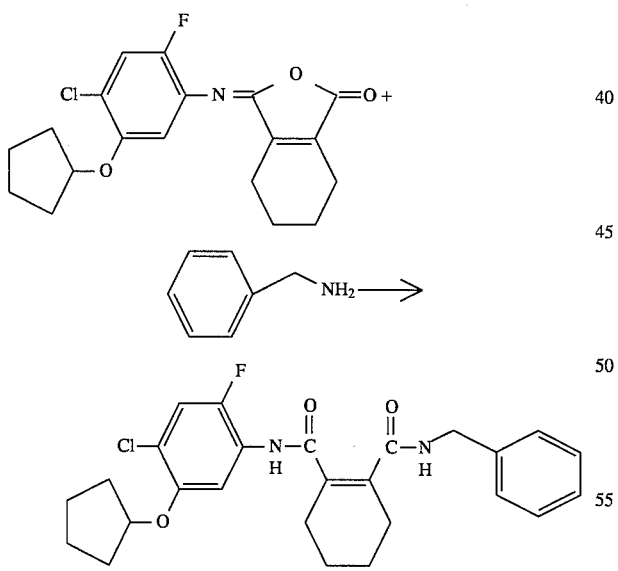

N-(2-Fluoro-4-chloro-5-cyclopentyloxyphenyl)- 3,4,5,6-tetrahydroisophthalimide (1.00 g, 2.75 mmol), benzylamine (0.300 g, 2.80 mmol), and benzene (20 ml) as a solvent were placed into a round bottom flask (50 cc) and stirred overnight at room temperature. After completion of the reaction, the solvent was distilled off under reduced pressure, and the resulting crystals were isolated by filtration. The crystals were washed with hexane and thoroughly dried to obtain N-(2-fluoro-4-chloro-5-cyclopentyloxyphenyl)-N'-benzyl-3,4,5,6-tetrahydrophthalamide as white crystals (0.947 g, 73.1% yield). The melting point and the spectral data thereof are shown in Example 20.

EXAMPLE 54

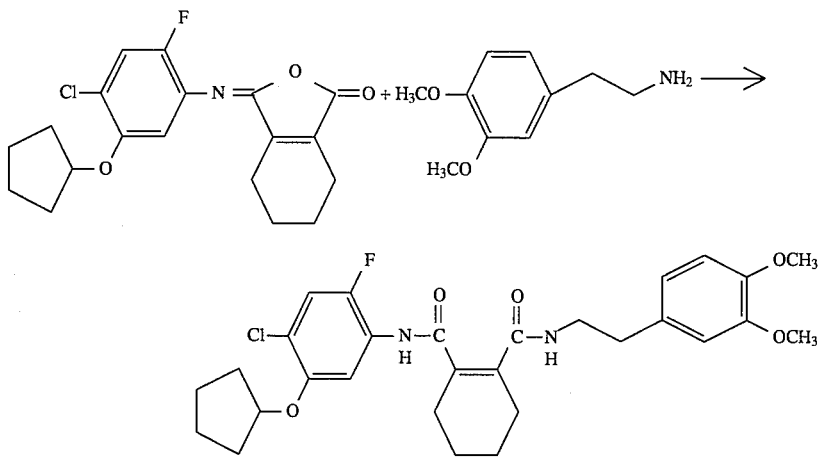

N-(2-Fluoro-4-chloro-5-cyclopentyloxyphenyl)- 3,4,5,6-tetrahydroisophthalimide (1.00 g, 2.75 mmol), 2-( 3,4-dimethoxyphenyl)ethylamine (0. 740 g, 4.08 mmol), and benzene (20 ml ) as a solvent were placed into a round bottom flask (50 cc) and stirred for 30 minutes at room temperature. After completion of the reaction, the solvent was distilled off under reduced pressure, and the resulting crystals were isolated by filtration. The crystals were washed with hexane and thoroughly dried to obtain N-(2-fluoro-4-chloro-5-cyclopentyloxyphenyl)-N'-{2-(3,4-di-methoxyphenyl)ethyl}- 3,4,5,6-tetrahydrophthalamide as white crystals (1.35 g, 90.1% yield). The melting point and the spectral data thereof are shown in Example 31.

EXAMPLE 55

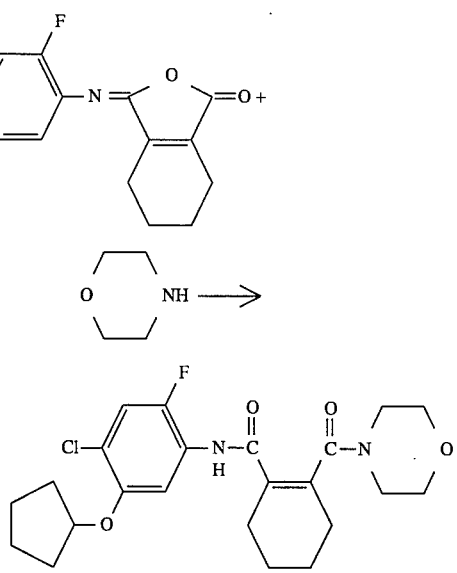

N-(2-Fluoro-4-chloro-5-cyclopentyloxyphenyl)- 3,4,5,6-tetrahydroisophthalimide (1.00 g, 2.75 mmol), morpholine (0.240 g, 2.75 mmol) and benzene (10 ml) as a solvent were placed into a round bottom flask (25 cc) and stirred overnight at room temperature. After completion of the reaction, the reaction mixture was poured into 1N hydrochloric acid (20 ml), and the mixture was extracted with ethyl acetate (30 ml×3 portions). After drying the organic layer over anhydrous magnesium sulfate, the drying agent was removed, the solvent was distilled off under reduced pressure, and the resulting crude product was isolated by filtration. The crystals were washed with hexane and thoroughly dried to obtain N-(2-fluoro-4-chloro- 5-cyclopentyloxyphenyl)-N',N'-diethyleneoxy-3,4,5,6-tetrahydrophthalamide as white crystals (1.17 g, 93.9% yield). The melting point and the spectral data thereof are shown in Example 19.

EXAMPLE 56

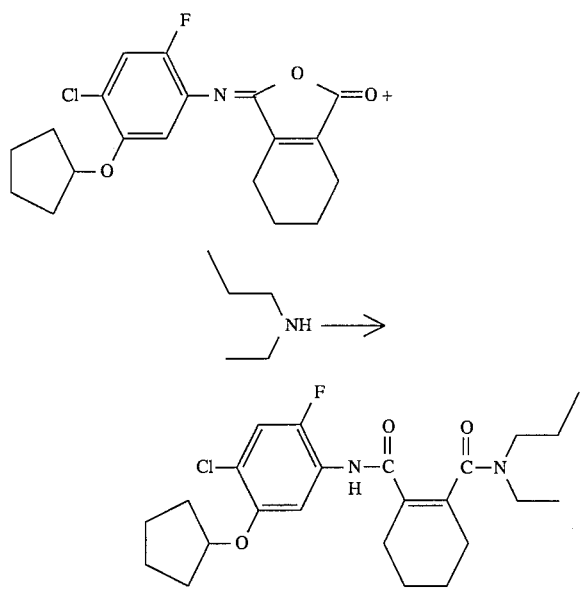

N-(2-Fluoro-4-chloro-5-cyclopentyloxyphenyl)- 3,4,5,6-tetrahydroisophthalimide (1.00 g, 2.75 mmol), N-ethyl-N-propylamine (0.300 g, 3.44 mmol) and benzene (10 ml) as a solvent were placed into a round bottom flask (25 cc) and stirred overnight at room temperature. After completion of the reaction, the reaction mixture was poured into 2N hydrochloric acid (20 ml), and the mixture was extracted with ethyl acetate (30 ml×3 portions). After drying the organic layer over anhydrous magnesium sulfate, the drying agent was removed, the solvent was distilled off under reduced pressure, and the resulting crude product was isolated by filtration. Then, the resulting oily substance was purified by column chromatography (active alumina, developing solvent: ethyl acetate/hexane=1/8) to obtain N-(2-fluoro-4-chloro-5-cyclopentyloxyphenyl)-N'-ethyl-N'-propyl- 3,4,5,6-tetrahydrophthalamide as an oily substance (0.698 g, 56.3% yield).

400MHz $^1$H-NMR (CDCl$_3$, TMS, pp): δ0.79 and 0.84(total 3H, each t,J=7.4 and 7.4Hz), 0.97 and 1.09(total 3H,each t, J=7.1 and 7.1Hz), 1.44 and 1.51(total 2H,each tq, J=7.4 and 7.4Hz), 1.62(2H,m), 1.74(4H,m), 1.88(6H, m), 2.34 (4H, brs), 3.16(1H, t,J=7.4Hz), 3.28(1H,q, J=7.1Hz), 3.29(1H, t,J=7.4Hz), 3.38(1H,brs), 4.78(1H, m), 7.101 and 7.098(total 1H,each d,J$_{HF}$=10.1 and 10.1Hz), 8.111 and 8.114(total 1H,each d, J$_{HF}$=7.2 and 7.2Hz), 8.53 and 8.55(total 1H,each brs).

IR (neat, cm$^{-1}$): 750, 862, 978, 1176, 1190, 1244, 1280, 1410, 1432, 1490, 1524, 1610, 1644, 1680, 2880, 2950, 2980, 3340.

EXAMPLE 57

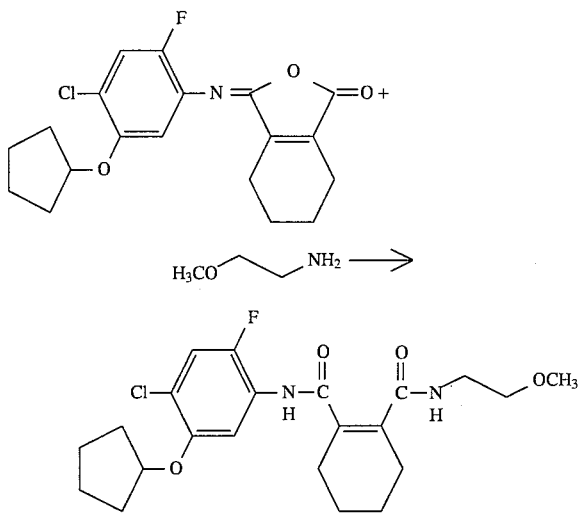

N-(2-Fluoro-4-chloro-5-cyclopentyloxyphenyl)- 3,4,5,6-tetrahydroisophthalimide (0.500 g, 1.37 mmol), 2 -methoxyethylamine (0.110 g, 1.46 mmol) and benzene (8 ml) as a solvent were placed into a round bottom flask (25 cc) and stirred for 5 minutes at room temperature. After completion of the reaction, the solvent was distilled off under reduced pressure, and the precipitated product was isolated by filtration. The crystals were washed with hexane and dried to obtain N-(2-fluoro-4-chloro-5-cyclopentyloxyphenyl)-N'-(2-methoxyethyl)-3,4,5,6-tetrahydrophthalamide as white crystals (0.501 g, 83.3% yield). The melting point and the spectral data thereof are shown in Example 40.

EXAMPLE 58

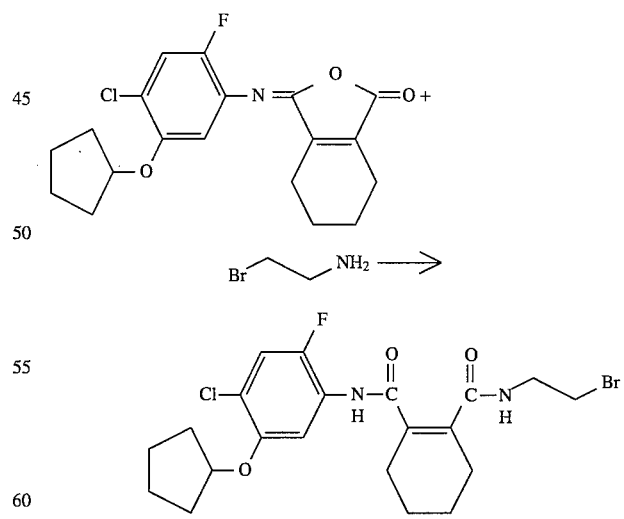

2-Aminoethyl bromide hydrobromide (0.280 g, 1.37 mmol) and potassium carbonate (0.110 g, 0.796 mmol) were placed into a round bottom flask (25 cc), followed by stirring at room temperature in an acetonitrile solvent until the generation of gas ceased. Then, N-(2-fluoro-4-chloro- 5-cyclopentyloxyphenyl)-3,4,5,6-tetrahydroisophthalimide (0.500 g, 1.37 mmol) was added thereto, followed by stirring for 30 minutes at room temperature. After completion of the reaction, the reaction mixture was poured into 1N hydrochloric acid (20 ml), and the mixture was extracted with ethyl acetate (30 ml×3 portions). After drying the organic layer over anhydrous magnesium sulfate, the drying agent was removed, and the solvent was distilled off under reduced pressure. The precipitated crystals were isolated by filtration, washed with hexane and dried to obtain N-(2-fluoro-4-chloro-5-cyclopentyloxyphenyl)-N'-( 2-bromoethyl)-3,4,5,6-tetrahydrophthalamide as white crystals (0.644 g, 96.4% yield).

Melting point: 140°–142° C.

400MHz $^1$H-NMR (CDCl$_3$,TMS,ppm): δ1.63(6H,m), 1.73(4H,m), 1.89(2H,m), 2.39(2H,m), 2.42(2H,m), 3.35(2H,t, J=5.8Hz), 3.65(2H,dt,J=5.8 and 5.8Hz), 4.80(1H, m), 6.25(1H,t,5.8Hz), 7.11(1H,d, $J_{HF}$=10.2Hz), 7.85 (1H, brs), 8.13 (1H, d, $J_{HF}$=7.2Hz).

IR (KBr disk, cm$^{-1}$): 860, 1196, 1245, 1280, 1300, 1360, 1390, 1410, 1430, 1442, 1490, 1504, 1538, 1628, 1642, 1670, 2940, 3250, 3320.

EXAMPLE 59

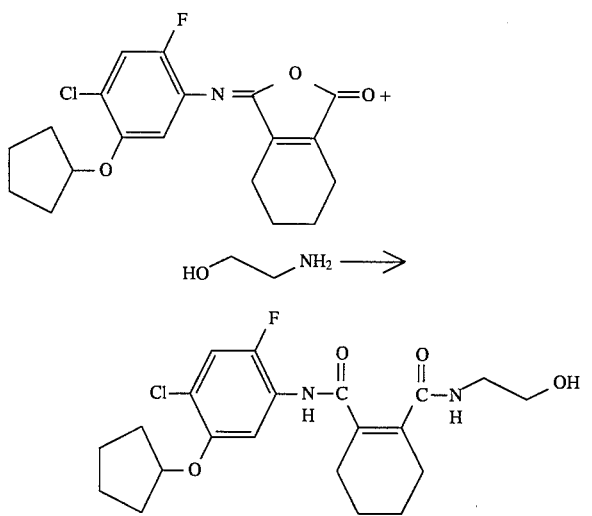

N-(2-Fluoro-4-chloro-5-cyclopentyloxyphenyl)- 3,4,5,6-tetrahydroisophthalimide (0.500 g, 1.37 mmol), ethanolamine (0.085 g, 1.39 mmol) and benzene (10 ml) as a solvent were placed into a round bottom flask (25 cc) and stirred for 30 minutes at room temperature. After completion of the reaction, the solvent was distilled off under reduced pressure, and the precipitated cystals were isolated by filtration. The crystals were washed with hexane and thoroughly dried to obtain N-(2-fluoro-4-chloro-5-cyclopentyloxyphenyl)-N'-( 2-hydroxyethyl)-3,4,5,6-tetrahydrophthalamide as white crystals (0.511 g, 87.8% yield).

Melting point: 150°–152° C.

$^1$H-NMR (CDCl$_3$, TMS, pp): δ1.38–2.07 (12H,m), 2.39 (4H,m), 2.73(1H,m), 3.39(2H,td,J=5.4 and 5.4Hz), 3.63(2H, t,J=5.4Hz), 4.82(1H,m), 6.45(1H,brt,J=5.4Hz), 7.18 (1H, d, $J_{HF}$=10.5Hz), 8.08 (1H, d, $J_{HF}$=7.5Hz), 8.09 (1H, brs).

IR (KBr disk, cm$^{-1}$): 864, 1034, 1198, 1256, 1298, 1328, 1362, 1392, 1415, 1490, 1502, 1608, 1644, 2890, 2950, 3280.

EXAMPLE 60

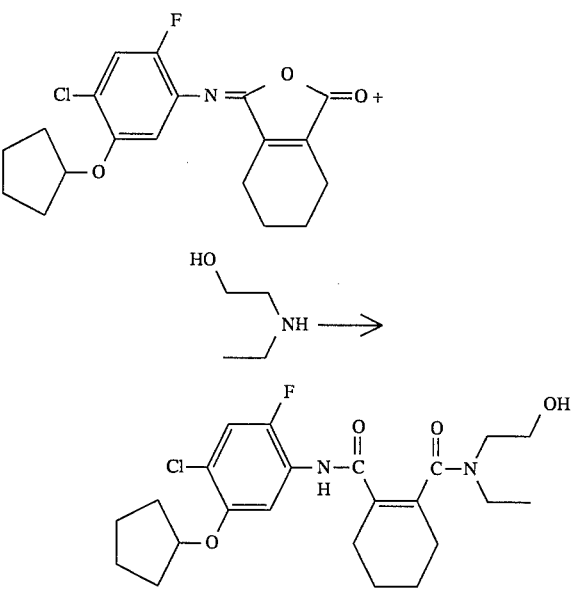

N-(2-Fluoro-4-chloro-5-cyclopentyloxyphenyl)- 3,4,5,6-tetrahydroisophthalimide (0.500 g, 1.37 mmol), 2 -ethylaminoethanol (0.150 g, 1.68 mmol) and benzene (8 ml) as a solvent were placed into a round bottom flask (25 cc) and stirred for 2 hours at room temperature. After completion of the reaction, the solvent was distilled off under reduced pressure, and diethyl ether was added to the resulting oily substance to crystallize. The cystals were isolated by filtration, washed with hexane and thoroughly dried to obtain N-(2-fluoro-4-chloro-5-cyclopentyloxyphenyl)-N'-ethyl-N'-( 2-hydroxyethyl)-3,4,5,6-tetrahydrophthalamide as white crystals (0.241 g, 38.8% yield).

Melting point: 132°–133° C.

400MHz $^1$H-NMR (CDCl$_3$,TMS,ppm): δ1.05 and 1.13(total 3H, each t,J=7.2 and 7.2Hz), 1.61(4H,m), 1.72–2.04(8H,m), 2.36(4H,brs), 2.44(1H,brs), 3.37 and 3.46(total 2H, each q,J=7.2 and 7.2Hz), 3.41(1H,t,J=5.4Hz), 3.52(1H,brs), 3.70 and 3.77 (total 2H, each d, $J_{HF}$=5.4 and 5.4Hz), 4.77(1H,m), 7.10 and 7.12(total 1H, each d, $J_{HF}$= 10.2 and 10.2Hz), 8.07(1H,d, $J_{HF}$=7.4Hz), 8.10 and 8.19 (total 1H, each brs).

IR (KBr disk, cm$^{-1}$): 860, 1050, 1178, 1190, 1258, 1360, 1412, 1430, 1452, 1492, 1540, 1596, 1640, 1670, 2890, 2950, 3230, 3240.

EXAMPLE 61

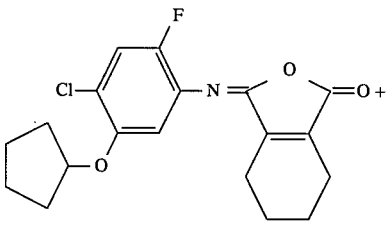

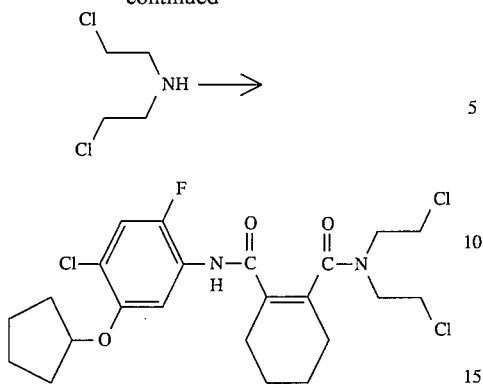

N-(2-Fluoro-4-chloro-5-cyclopentyloxyphenyl)- 3,4,5,6-tetrahydroisophthalimide (1.00 g, 2.75 mmol), bis(2-chloroethyl)amine (1.26 g, 8.89 mmol) and benzene (15 ml) as a solvent were placed into a round bottom flask (50 cc) and stirred overnight at room temperature. After completion of the reaction, the reaction mixture was poured into 1N hydrochloric acid (20 ml), and the mixture was extracted with ethyl acetate (30 ml×3 portions). After drying the organic layer over anhydrous magnesium sulfate, the drying agent was removed, the solvent was distilled off under reduced pressure, and the resulting crude product was isolated by filtration. Then, the resulting oily substance was purified by column chromatography (active alumina, developing solvent: ethyl acetate/hexane=1/8) to obtain N-(2-fluoro-4-chloro-5-cyclopentyloxyphenyl-N',N'-bis(2-chloroethyl)-3,4,5,6-tetrahydrophthalamide as white crystals (0.514 g, 36.9% yield).

Melting point: 120°–122° C.

400MHz $^1$H-NMR (CDCl$_3$,TMS,ppm): δ1.62(2H,m), 1.71–1.97(10H, m), 2.39(2H,m), 2.43(2H,m), 3.59(2H,t, J=6.4Hz), 3.65–3.77(6H,m), 4.78(1H,m), 7.11(1H,d,J$_{HF}$=10.3Hz), 8.07(1H,brs), 8.12(1H,d,J$_{HF}$=7.2Hz).

IR (KBr disk, cm$^{-1}$): 738, 872, 884, 1038, 1178, 1190, 1200, 1212, 1242, 1301, 1420, 1442, 1462, 1495, 1524, 1628, 1692, 2980, 3500.

EXAMPLE 62

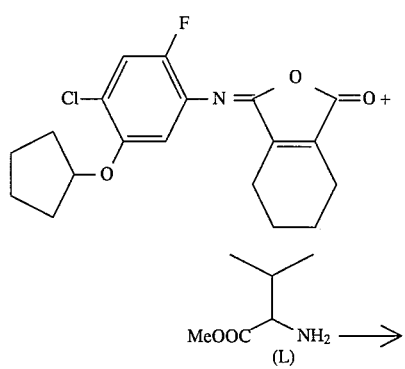

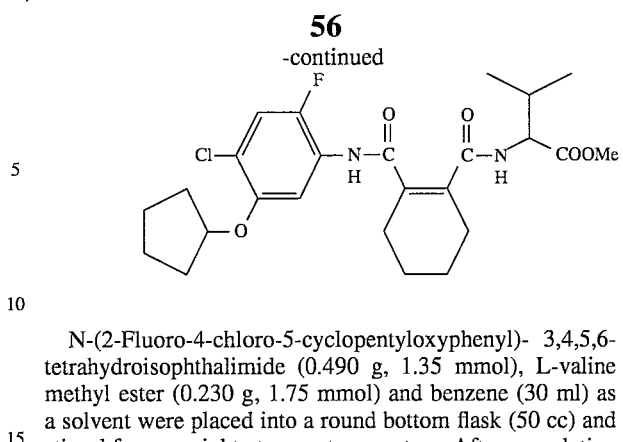

N-(2-Fluoro-4-chloro-5-cyclopentyloxyphenyl)- 3,4,5,6-tetrahydroisophthalimide (0.490 g, 1.35 mmol), L-valine methyl ester (0.230 g, 1.75 mmol) and benzene (30 ml) as a solvent were placed into a round bottom flask (50 cc) and stirred for overnight at room temperature. After completion of the reaction, the solvent was distilled off under reduced pressure, and the resulting crude product was recrystallized from hexane to obtain N-2-fluoro-4-chloro-5-cyclopentyloxyphenyl)-N'-(1-methoxycarbonyl-2-methylpropyl)-3,4,5,6-tetrahydrophthalamide as white crystals (0.535.g, 80.0% yield).

Melting point: 146°–148° C.

400MHz $^1$H-NMR (CDCl$_3$,TMS,ppm): δ0,776 and 0.842(total 3H,each d,J=3.0Hz), 1.70(4H,m), 1.83(5H,m), 2.38(4H,m), 3.60(3H, s), 4.46(1H,dd,J=12.0 and 3.0Hz), 4.31(1H,m), 6.24(1H,brd,J=9.0Hz), 7.01(1H,d,J$_{HF}$=10.5Hz), 7.82(1H,brs), 8.10(1H, d,J$_{HF}$=7.5Hz).

IR (KBr disk, cm$^{-1}$): 860, 1185, 1245, 1320, 1360, 1410, 1430, 1490, 1530, 1620, 1650, 1750, 2950, 3275.

EXAMPLE 63

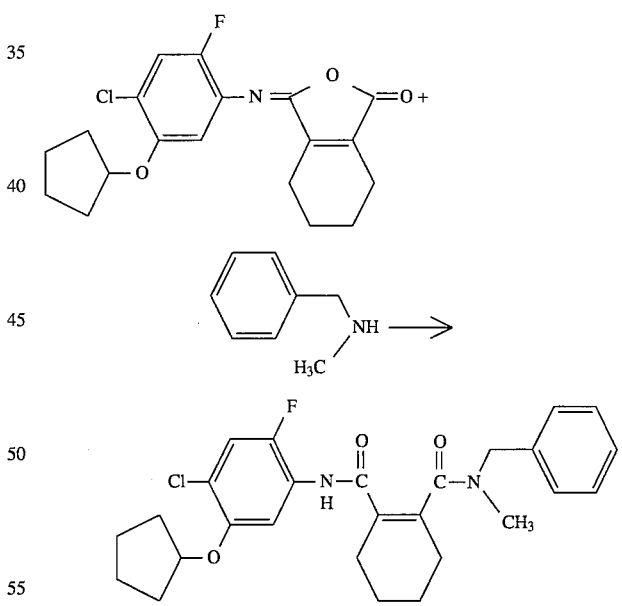

Sodium hydride (in oil 60%, 0.210 g, 5.25 mmol) was placed into a two-necked round bottom flask (50 cc), and oils were removed by washing with hexane in an argon atmosphere. After cooling to 0° C., a solution of N-methylbenzylamine (0.410 g, 3.38 mmol) in THF (4 ml) was dropwise added thereto slowly, followed by elevating the temperature to room temperature and stirring for 20 minutes. Then, the mixture was cooled to −70° C., and a solution of N-(2-fluoro- 4-chloro-5-cyclopentyloxyphenyl)-3,4,5,6-tetrahydroisophthalimide (1.02 g, 2.80 mmol) in THF (10 ml)

was dropwise added thereto slowly. The temperaure of the mixture was elevated to room temperature, followed by stirring for one hour. After completion of the reaction, the reaction mixture was poured into 1N-hydrochloric acid (30 ml), and the mixture was extracted with ethyl acetate (30 ml×3 portions). After drying the organic layer over anhydrous magnesium sulfate, the drying agent was removed, and the solvent was distilled off under reduced pressure. Then, the resulting oily substance was purified by column chromatography (active alumina, developing solvent: ethyl acetate/hexane=1/4) to obtain N-(2-fluoro-4-chloro-5 -cyclopentyloxyphenyl)-N'-benzyl-N'-methyl-3,4,5,6-tetrahydrophthalamide as an oily substance (0.420 g, 30.9% yield).

400MHz $^1$H-NMR (CDCl$_3$,TMS,ppm): δ1.58–1.76(6H, m), 1.80–1.99(6H,m), 2.36(2H,m), 2.44(2H,m), 2.85 and 2.87(total 3H,each s), 4.48 and 4.58(total 2H, each brs), 4.77 and 4.81(total 1H, each brm), 7.05–7.17 (5H,m), 7.28 and 7.30(total 1H, each m), 8.08 and 8.12(total 1H, each d,J$_{HF}$=7.2Hz and 7.2Hz), 8.42 and 8.44(total 1H, each brs).

IR (neat, cm$^{-1}$): 700, 738, 862, 976, 1039, 1178, 1192, 1244, 1280, 1410, 1434, 1450, 1490, 1520, 1612, 1642, 1680, 1740, 2890, 2960, 3350.

EXAMPLE 64

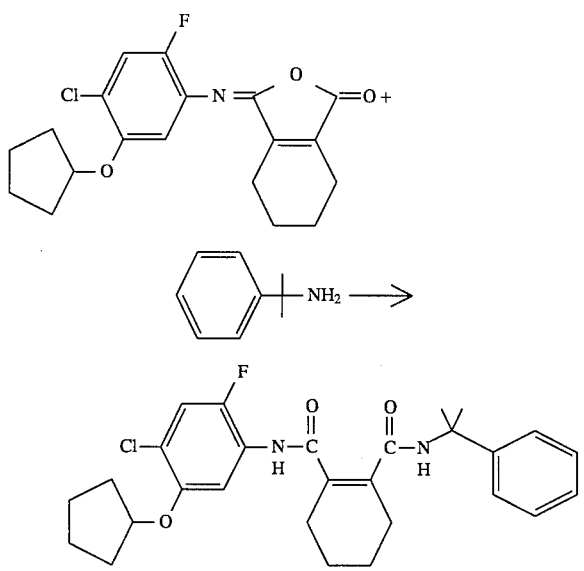

N-(2-Fluoro-4-chloro-5-cyclopentyloxyphenyl)- 3,4,5,6-tetrahydroisophthalimide (1.00 g, 2.75 mmol), cumylamine (0.370 g, 2.74 mmol), triethylamine (0.310 g, 3.06 mmol) and benzene (10 ml) as a solvent were placed into a round bottom flask (50 cc) and stirred overnight at room temperature, followed by heating at 50° C. for 5 hours. After completion of the reaction, the reaction mixture was poured into 1N hydrochloric acid (50 ml), and the mixture was extracted with ethyl acetate (50 ml×3 portions). After drying the organic layer over anhydrous magnesium sulfate, the drying agent was removed, and the solvent was distilled off under reduced pressure. The resulting crude product was recrystallized from ether/hexane to obtain N-(2-fluoro-4-chloro-5-cyclopentyloxyphenyl)-N'-cumyl- 3,4,5,6-tetrahydrophthalamide as white crystals (0.220 g, 16.1% yield).

Melting point: 206°–207° C.

400MHz $^1$H-NMR (CDCl$_3$,TMS,ppm): δ1.58(6H,s), 1.70(4H,m), 1.92(8H,m), 2.38(4H,m), 4.80(1H,m), 6.09(1H,brs), 7.10(1H,d,J$_{HF}$=10.2Hz), 7.13–7.19(3H,m), 7.27–7.29(2H,m), 8.03(1H,brs), 8.25(1H,d,J$_{HF}$=7.2).

IR (KBr disk, cm$^{-1}$): 695, 758, 860, 1168, 1185, 1240, 1305, 1360, 1405, 1440, 1485, 1520, 1545, 1608, 1635, 2940, 2980, 3270, 3320.

EXAMPLE 65

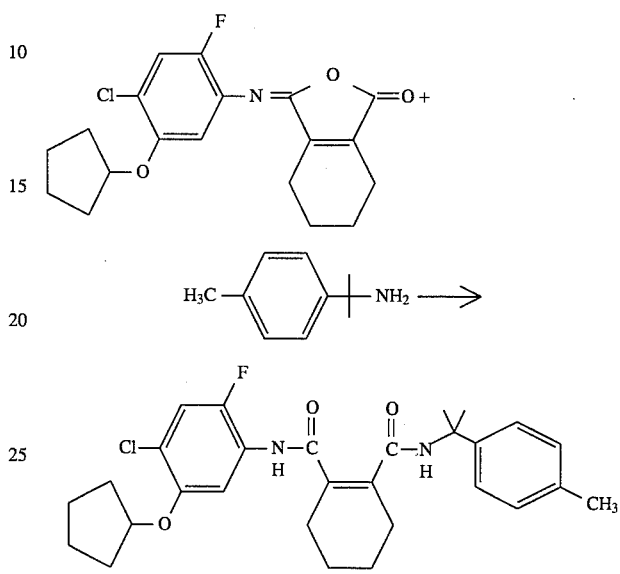

N-(2-Fluoro-4-chloro-5-cyclopentyloxyphenyl)- 3,4,5,6-tetrahydroisophthalimide (1.00 g, 2.75 mmol), 4 -methylcumylamine (0.620 g, 4.15 mmol), N-methylmorpholine (0.310 g, 3.06 mmol) and benzene (15 ml) as a solvent were placed into a round bottom flask (50 cc) and stirred overnight at room temperature. After completion of the reaction, the reaction mixture was poured into 1N hydrochloric acid (50 ml), and the mixture was extracted with chloroform (40 ml×3 portions). After drying the organic layer over anhydrous magnesium sulfate, the drying agent was removed, and the solvent was distilled off under reduced pressure. The precipitated crude product was recrystallized from ethyl acetate/acetone to obtain N-(2 -fluoro-4-chloro-5-cyclopentyloxyphenyl)-N'-(4-methylcumyl- 3,4,5,6-tetrahydrophthalamide as white crystals (0.487 g, 34.5% yield).

Melting point: 192°–194° C.

400MHz $^1$H-NMR (CDCl$_3$,TMS,ppm): δ1.57(6H,s), 1.63(2H,m), 1.70(4H,m), 1.89(2H,m), 1.92(4H,m), 2.24(3H,m), 2.37(2H,m), 2.39(2H,m), 4.81(1H,m), 6.04 (1H, brs), 6.94(2H,d,J=8.0Hz), 7.09(1H,d,J$_{HF}$=10.2Hz), 7.16 (2H,d,J=8.0Hz), 8.04(1H,brs), 8.25(1H,d,$^{J}$=7.2Hz).

IR (KBr disk, cm$^{-1}$): 815, 865, 1172, 1188, 1241, 1308, 1360, 1410, 1488, 1524, 1544, 1610, 1641, 2940, 2980, 3280.

EXAMPLE 66

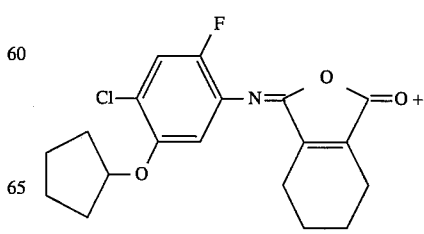

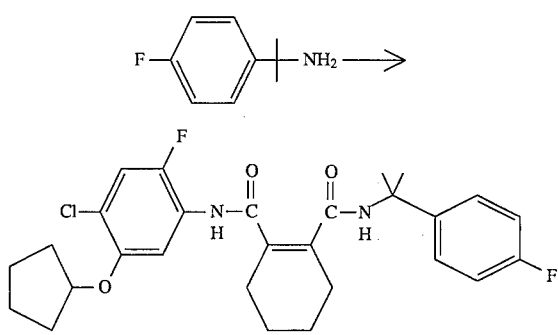

N-(2-Fluoro-4-chloro-5-cyclopentyloxyphenyl)- 3,4,5,6-tetrahydroisophthalimide (1.00 g, 2.75 mmol), 4-fluorocumylamine (0.600 g, 3.92 mmol), N-methylmorpholine (0.380 g, 3.26 mmol), and benzene (10 ml) as a solvent were placed into a round bottom flask (50 cc) and stirred overnight at room temperature. After completion of the reaction, the solvent was distilled off under reduced pressure, and the resulting crude product was recrystallized from ethyl acetate/acetone to obtain N-(2-fluoro-4-chloro-5-cyclopentyloxyphenyl)-N-(4-fluorocumyl)- 3,4,5,6-tetrahydrophthalamide as white crystals (0.417 g, 29.3% yield).

Melting point: 213°–215° C.

$^1$H-NMR (CDCl$_3$,TMS,ppm): δ1.60(6H, s), 1.70(6H,m), 1.95(6H,m), 2.38(4H,m), 4.83(1H,m), 6.12(1H, brs), 6.86(2H,t,J$_{HF}$=9.0Hz), 7.2–7.4(2H,m), 7.16(1H,d,J$_{HF}$=10.5Hz), 8.02(1H,brs), 8.35(1H, d, J$_{HF}$=7.5Hz).

IR (KBr disk, cm$^{-1}$): 838, 864, 1164, 1172, 1196, 1230, 1244, 1310, 1362, 1408, 1444, 1484, 1510, 1540, 1608, 1624, 1640, 1678, 2940, 3260, 3310.

EXAMPLE 67

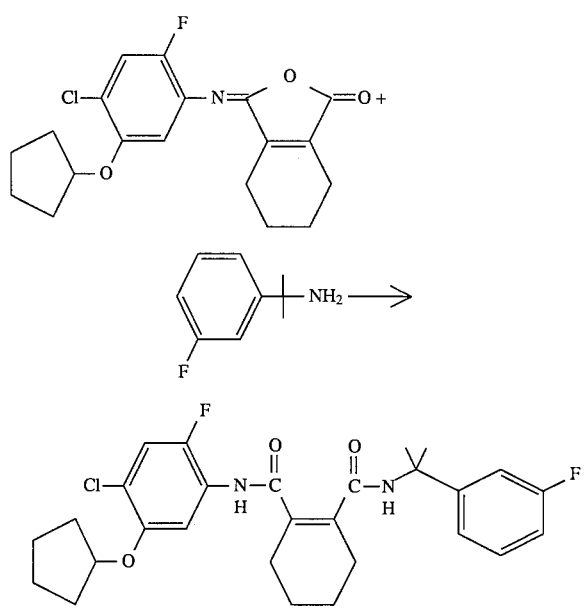

N-(2-Fluoro-4-chloro-5-cyclopentyloxyphenyl)- 3,4,5,6-tetrahydroisophthalimide (1.00 g, 2.75 mmol), 3-fluorocumylamine (0.430 g, 2.81 mmol), triethylamine (0.290 g, 2.87 mmol), and benzene (10 ml) as a solvent were placed into a round bottom flask (50 cc) and stirred overnight at room temperature, followed by heating at 50° C. for 3 hours. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(3-fluorocumyl)- 3,4,5,6-tetrahydrophthalamide as white crystals (0.167 g, 11.7% yield).

Melting point: 231°–234° C.

400MHz $^1$H-NMR (CDCl$_3$, TMS, ppm): δ1.56(6H,m), 1.65(2H,m), 1.71(4H,m), 1.87(2H,m), 1.90(4H,m), 2.37(2H,m), 2.39(2H,m), 4.81(1H,m), 6.12 (1H, brs), 6.83 (1H, dddd,J$_{HF}$=8.05Hz,J=7.9,2.4 and 1.0Hz), 6.95(1H,ddd, J$_{HF}$=10.6,J=2.4 and 2.1Hz), 7.04(1H,ddd,J$_{HF}$=6.9 and 1.0 and 2.1Hz), 7.08(1H,dd, J=7.9 and 6.9Hz), 7.11(1H,d,J$_{HF}$=10.2Hz), 7.96(1H,brs), 8.24(1H,d, J$_{HF}$=7.2Hz).

IR (KBr disk, cm$^{-1}$): 699, 782, 868, 1190, 1266, 1242, 1310, 1412, 1494, 1530, 1546, 1612, 1645, 2950, 3290.

EXAMPLE 68

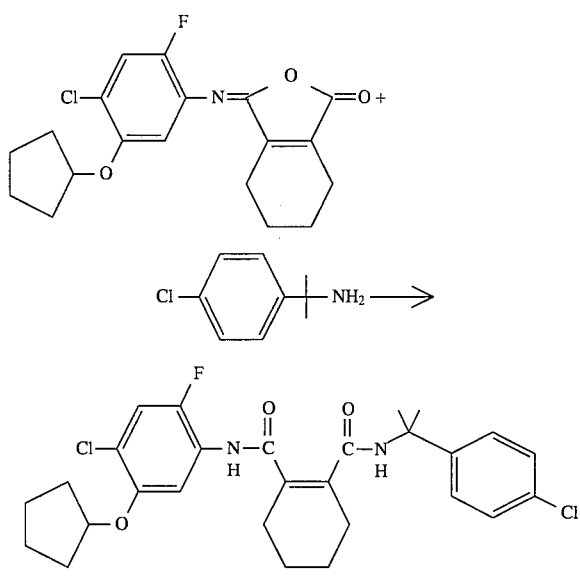

N-(2-Fluoro-4-chloro-5-cyclopentyloxyphenyl)- 3,4,5,6-tetrahydroisophthalimide (0.900 g, 2.74 mmol), 4-chlorocumylamine (0.600 g, 3.54 mmol), N-methylmorpholine (0.300 g, 2.97 mmol), and benzene (15 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 4-chlorocumyl)-3,4,5,6-tetrahydrophthalamide as white crystals (0.404 g, 30.7% yield).

Melting point: 218°–219° C.

400MHz $^1$H-NMR (CDCl$_3$, TMS, pp): δ1.55(6H, s), 1.65(2H,m), 1.71(4H,m), 1.88(2H,m), 1.91(4H,m), 2.35(2H,m), 2.39(2H,), 4.81(1H,m), 6.11(1H,brs), 7.06(2H, d,J=8.6Hz), 7.12(1H,d,J$_{HF}$=10.2Hz), 7.19(2H,d, J=8.6Hz), 7.97 (1H, brs), 8.24 (1H, d, J$_{HF}$=7.2Hz).

IR (KBr disk, cm$^{-1}$): 830, 864, 1176, 1196, 1242, 1315, 1404, 1484, 1518, 1540, 1608, 1620, 1642, 1678, 2940, 2980, 3260, 3320.

EXAMPLE 69

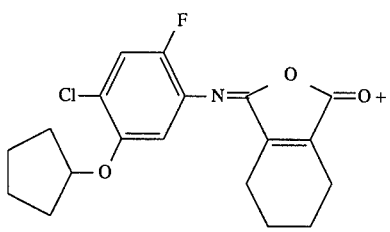

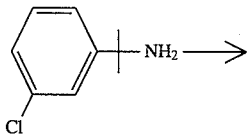

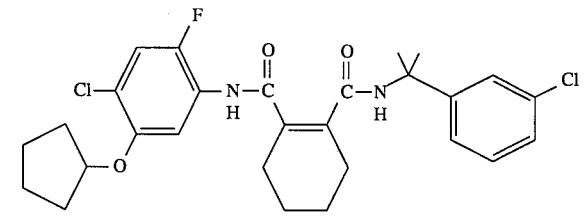

N-(2-Fluoro-4-chloro-5-cyclopentyloxyphenyl)- 3,4,5,6-tetrahydroisophthalimide (1.00 g, 2.75 mmol), 3-chlorocumylamine (0.630 g, 3.71 mmol), N-methylmorpholine (0.670 g, 6.62 mmol), and benzene (10 ml) as a solvent were placed into a round bottom flask (50 cc) and stirred overnight at room temperature, followed by heating at 50° C. for 7 hours. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(3-chlorocumyl)- 3,4,5,6-tetrahydrophthalamide as white crystals (0.859 g, 58.6% yield).

Melting point: 222°–226° C.

$^1$H-NMR (CDCl$_3$,TMS,ppm): δ1.55(6H,s), 1.70(6H,m), 1.88(6H, m), 2.38(4H,m), 4.82(1H,m), 6.18(1H,brs), 7.16(1H, d,J$_{HF}$=10.5Hz), 7.18(3H,m), 7.34(1H,s), 8.03(1H, brs), 8.32(1H,d,J$_{HF}$=7.5Hz).

IR (KBr disk, cm$^{-1}$): 698, 781, 1172, 1190, 1242, 1305, 1360, 1408, 1490, 1525, 1538, 1610, 1642, 2950, 2980, 3280.

EXAMPLE 70

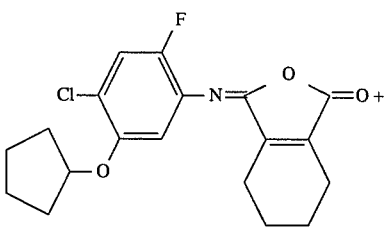

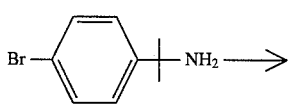

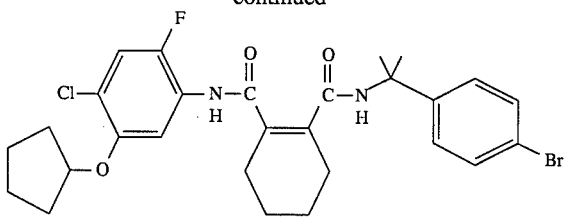

N-(2-Fluoro-4-chloro-5-cyclopentyloxyphenyl)- 3,4,5,6-tetrahydroisophthalimide (1.00 g, 2.75 mmol), bromocumylamine (0.770 g, 3.60 mmol), N-methylmorpholine (0.310 g, 3.06 mmol), and benzene (15 ml) as a solvent were placed into a round bottom flask (50 cc) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(4-bromocumyl)-3,4,5,6-tetrahydrophthalamide as white crystals (0.515 g, 32.4% yield).

Melting point: 214°–216° C.

$^1$H-NMR (CDCl$_3$,TMS,ppm): δ1.54(6H, s), 1.69(6H,m), 1.90(6H, m), 2.36(4H,m), 4.83(1H,m), 6.14(1H,brs), 7.16(1H, d,J$_{HF}$=10.5Hz), 7.28(2H,d,J=6.0Hz), 7.37(2H,d, J=6.0Hz), 8.03(1H,brs), 8.33 (1H, d, J$_{HF}$=7.5Hz).

IR (KBr disk, cm$^{-1}$): 821, 865, 1176, 1195, 1242, 1315, 1408, 1490, 1518, 1540, 1610, 1621, 1642, 1678, 2940, 2980, 3260, 3320.

EXAMPLE 71

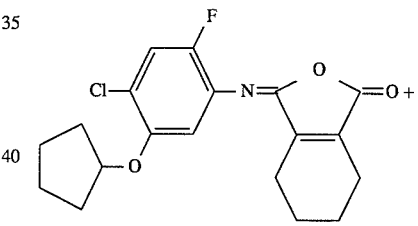

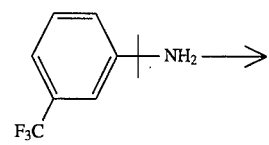

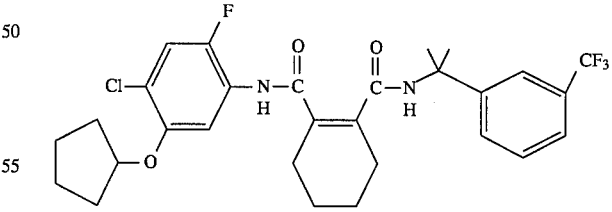

N-(2-Fluoro-4-chloro-5-cyclopentyloxyphenyl)- 3,4,5,6-tetrahydroisophthalimide (1.00 g, 2.75 mmol), 3-trifluoromethylcumylamine (0.730 g, 3.59 mmol), N-methylmorpholine (0.320 g, 3.16 mmol), and benzene (15 ml) as a solvent were placed into a round bottom flask (50 cc) and stirred overnight at room temperature. After completion of the reaction, the solvent was distilled off under reduced pressure, and the resulting crude product was recrystallized from chloroform/acetone to obtain N-(2-fluoro- 4-chloro-5- cyclopentyloxyphenyl)-N,-(3-trifluoromethylcumyl)- 3,4,5,6-tetrahydrophthalamide as white crystals (0.360 g, 23.1% yield).

Melting point: 231°–235° C.

400MHz $^1$H-NMR (CDCl$_3$, TMS, pp): δ1.58(6H,s), 1.63(2H,m), 1.72(4H,m), 1.87(2H,m), 1.90(4H,m), 2.36(2H,m), 2.40(2H,m), 4.81(1H,m), 6.17(1H,brs), 7.11(1H, d, J$_{HF}$=10.2Hz), 7.22(1H, dd, J=7.7 and 7.7Hz), 7.41 (1H, d, J=7.7Hz), 7.72(1H,d,J=7.7Hz), 7.55(1H, s), 8.17(1H,brs), 8.23(1H,d, J$_{HF}$=7.2Hz).

IR (KBr disk, cm$^{-1}$): 702, 810, 870, 1078, 1130, 1175, 1198, 1248, 1318, 1339, 1410, 1490, 1524, 1548, 1610, 1622, 1644, 1680, 2960, 3270, 3320.

EXAMPLE 72

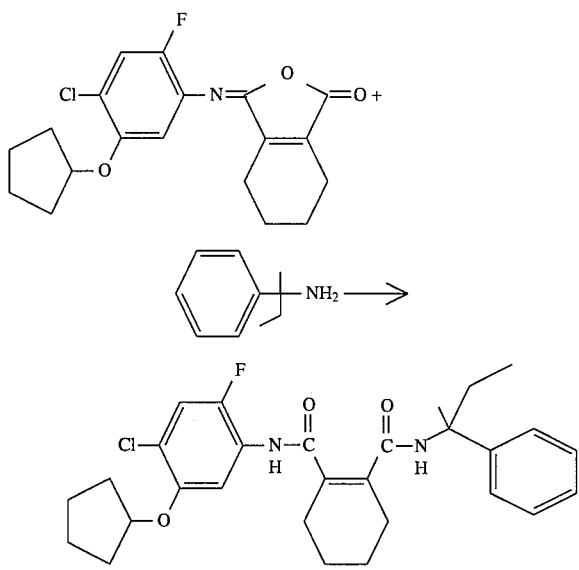

N-(2-Fluoro-4-chloro-5-cyclopentyloxyphenyl)- 3,4,5,6-tetrahydroisophthalimide (1.00 g, 2.75 mmol), 1 -phenyl-1-methylpropylamine (0.540 g, 3.62 mmol), N-methylmorpholine (0.310 g, 3.06 mmol), and benzene (15 ml ) as a solvent were placed into a round bottom flask (50 cc ) and stirred overnight at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-(1-phenyl)-1-methylpropyl-3,4,5,6-tetrahydrophthalamide as white crystals (0.403 g, 28.6% yield).

Melting point: 195°–198° C.

400MHz $^1$H-NMR (CDCl$_3$, TMS, ppm): δ0.67(3H, t, J=7.4Hz), 1.59(3H,s), 1.6–2.0(14H,m), 2.39(4H,m), 4.79(1H, m),6.07(1H,brs), 7.10(1H,d,J$_{HF}$=10.2Hz), 7.1–7.2(5H,m), 8.07(1H,brs), 8.25(1H,d,J$_{HF}$=7.2Hz).

IR (KBr disk, cm$^{-1}$): 700, 761, 862, 1170, 1184, 1241, 1310, 1360, 1402, 1444, 1480, 1518, 1538, 1610, 1621, 1644, 1678, 2880, 2940, 2980, 3260, 3310.

EXAMPLE 73

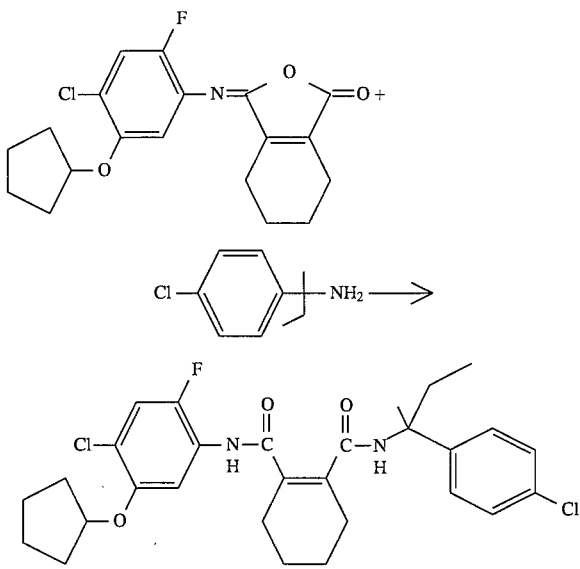

N-(2-Fluoro-4-chloro-5-cyclopentyloxyphenyl)- 3,4,5,6-tetrahydroisophthalimide (1.00 g, 2.75 mmol), 1-(4-chlorophenyl)-1-methylpropylamaine (0.760 g, 4.14 mmol), N-methylmorpholine (0.310 g, 3.06 mmol) and benzene (15 ml) as a solvent were placed into a round bottom flask (50 cc) and stirred overnight at room temperature. After completion of the reaction, the reaction mixture was poured into 2N hydrochloric acid (30 ml), and the mixture was extracted with ethyl acetate (30 ml×3 portions). After drying the organic layer over anhydrous magnesium sulfate, the drying agent was removed, and the solvent was distilled off under reduced pressure. The resulting crude product was recrystallized from ethyl acetate/acetone to obtain N-(2-fluoro-4-chloro-5-cyclopentyloxyphenyl)-N'-{1-(4-chlorophenyl)-1-methylpropyl}-3,4,5,6-tetrahydrophthalamide as white crystals (0.298 g, 19.8% yield).

Melting point: 200°–201 ° C.

400MHz $^1$H-NMR (CDCl$_3$,TMS,ppm): δ0.68(3H,t, J=7.4Hz), 1.56(3H,s), 1.6–1.9(14H,m), 2.40(4H,m), 4.80(1H, m),6.08(1H,brs), 7.04(1H,d,J=8.6Hz), 7.11(1H,d, J$_{HF}$=10.3Hz), 7.14(1H,d,J=8.6Hz), 8.00(1H,brs), 8.25 (1H, d, J$_{HF}$=7.2Hz).

IR (KBr disk, cm$^{-1}$): 830, 868, 1174, 1192, 1244, 1318, 1408, 1490, 1518, 1608, 1620, 1642, 1678, 2950, 2980, 3270.

EXAMPLE 74

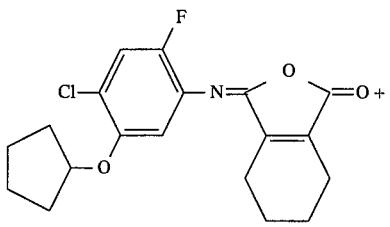

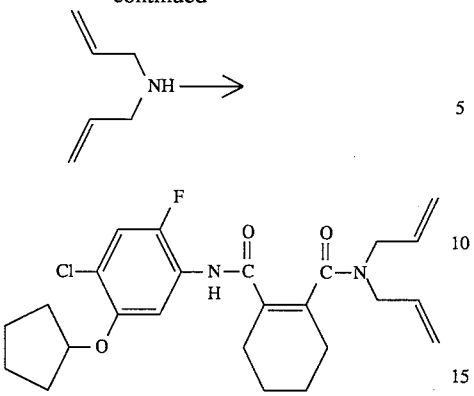

N-(2-Fluoro-4-chloro-5-cyclopentyloxyphenyl)- 3,4,5,6-tetrahydroisophthalimide (0.500 g, 1.37 mmol), diallylamine (0.216 g, 2.22 mmol), and benzene (10 ml) as a solvent were placed into a round bottom flask (25 cc) and stirred overnight at room temperature. After completion of the reaction, the reaction mixture was poured into 1N hydrochloric acid (10 ml), and the mixture was extracted with ethyl acetate (20 ml×3 portions). After drying the organic layer over anhydrous magnesium sulfate, the drying agent was removed, and the solvent was distilled off under reduced pressure. Then, the resulting oily substance was purified by column chromatography (active alumina, developing solvent: ethyl acetate/hexane=1/1). The solvent was distilled off under reduced presssure, and the precipitated crystals were isolated by filtration to obtain N-(2-fluoro-4-chloro-5-cyclopentyloxyphenyl)-N',N'-diallyl- 3,4,5,6-tetrahydrophthalamide as white crystals (0.165 g, 26.1% yield).

Melting point: 74°–76° C.

400MHz $^1$H-NMR (CDCl$_3$,TMS,ppm): δ1.58–1.98(12H, m), 2.34(2H,m), 2.43(2H,m), 3.86(2H,brd,J=5.2Hz), 3.98(2H,brs), 4.79(1H,m), 4.98(1H,dd,J=10.2 and 1.3Hz), 5.06(1H,dd,J=17.2 and 1.3Hz), 5.12(1H,dd, J=17.1 and 1.3Hz), 5.18(1H,dd,J=10.3 and 1.3Hz), 5.57(1H, ddt,J=10.2 and 17.2 and 6.0Hz), 5.65(1H, ddt,J=10.3 and 17.1 and 5.7Hz), 7.10(1H,d, J$_{HF}$=10.2Hz), 8.11(1H,d,J$_{HF}$=7.2Hz), 8.37 (1H, brs).

IR (KBr disk, cm$^{-1}$): 862, 930, 978, 1175, 1185, 1243, 1408, 1488, 1528, 1610, 1625, 1642, 1672, 2870, 2950, 2980, 3350.

EXAMPLE 75

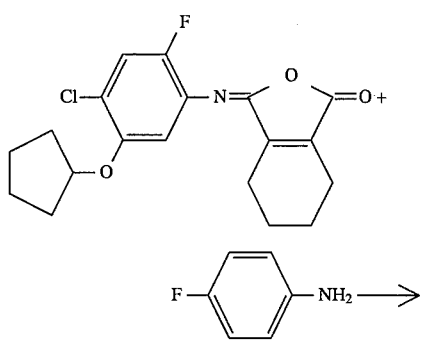

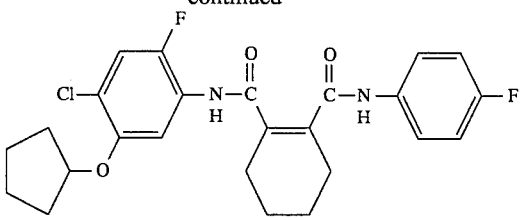

N-(2-Fluoro-4-chloro-5-cyclopentyloxyphenyl)- 3,4,5,6-tetrahydroisophthalimide (1.00 g, 2.75 mmol), 4-fluoroaniline (0.310 g, 2.79 mmol), and benzene (10 ml) as a solvent were placed into a round bottom flask (50 cc) and stirred for 3 hours at room temperature. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 4-fluorophenyl)-3,4,5,6-tetrahydrophthalamide as white crystals (0.950 g, 72.7% yield).

Melting point: 209°–210° C.

400MHz $^1$H-NMR (CDCl$_3$+DMSO-d$_6$,TMS,ppm): δ1.59(2H,m), 1.76(4H,m), 1.79(6H,m), 2.45(4H,m), 4.62(1H,m), 6.94(2H,dd, J=8.8 and J$_{HF}$=8.8Hz), 7.07(1H,d, J$_{HF}$=10.1Hz), 7.54(2H,dd,J=8.8 and J$_{HF}$=4.9Hz), 7.79(1H, d,J$_{HF}$=7.1Hz), 8.88(1H,brs), 9.56(1H,brs).

IR (KBr disk, cm$^{-1}$): 694, 830, 861, 1195, 1212, 1228, 1240, 1260, 1284, 1316, 1360, 1390, 1408, 1500, 1510, 1530, 1612, 1642, 2950, 3260.

EXAMPLE 76

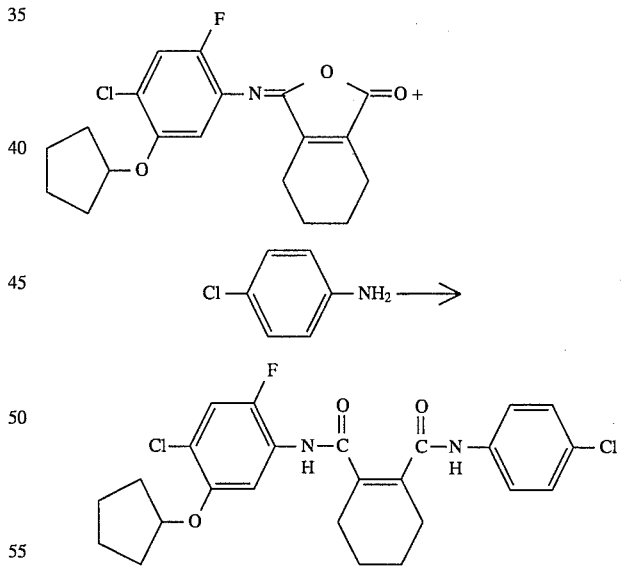

N-(2-Fluoro-4-chloro-5-cyclopentyloxyphenyl)- 3,4,5,6-tetrahydroisophthalimide (1.00 g, 2.75 mmol), 4-chloroaniline (0.350 g, 2.74 mmol), and benzene (10 ml) as a solvent were placed into a round bottom flask (50cc) and stirred overnight at room temperature, followed by heating at 50° to 70° C. for 7 hours. After completion of the reaction, the solvent was distilled off under reduced pressure, and the precipitated crystals were isolated by filtration. The crystals were washed with hexane and dried to obtain N-(2-fluoro-4-chloro-5-cyclopentyloxyphenyl)-N'-( 4-chlorophenyl)-3, 4,5,6-tetrahydrophthalamide as white crystals (0.576 g, 42.8% yield).

Melting point: 221°–222° C.

$^1$H-NMR (CDCl$_3$+DMSO-d$_6$,TMS,ppm): δ1.50–2.00(12H,m), 2.45(4H,m), 4.58(1H,m), 7.03(1H,d, J$_{HF}$=10.5Hz), 7.18(2H,d,J=9.0Hz), 7.52(2H,d,J=9.0Hz), 7.77(1H, d,J$_{HF}$=7.5Hz), 8.61(1H,brs), 9.23(1H,brs).

IR (KBr disk, cm$^{-1}$): 825, 862, 1190, 1255, 1290, 1315, 1360, 1400, 1495, 1518, 1526, 1536, 1598, 1610, 1645, 2950, 3250.

EXAMPLE 77

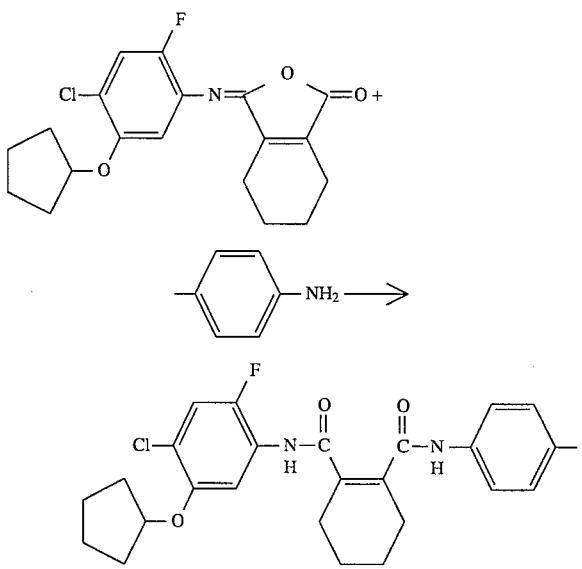

N-(2-Fluoro-4-chloro-5-cyclopentyloxyphenyl)- 3,4,5,6-tetrahydroisophthalimide (1.00 g, 2.75 mmol), 4-methylaniline (0.350 g, 3.27 mmol), triethylamine (0.290 g, 2.87 mmol) and benzene (15 ml) as a solvent were placed into a round bottom flask (50 cc) and stirred overnight at room temperature. After completion of the reaction, the reaction mixture was poured into 1N hydrochloric acid (50 ml), and the mixture was extracted with chloroform (40 ml×3 portions). After drying the organic layer over anhydrous magnesium sulfate, the drying agent was removed, and the solvent was distilled off under reduced pressure. The precipitated crystals were isolated by filtration, washed with hexane and dried to obtain N-(2-fluoro-4-chloro- 5-cyclopentyloxyphenyl)-N'-(4-methylphenyl)-3,4,5,6-tetrahydrophthalamide as white crystals (0.396 g, 30.6% yield).

Melting point: 214°–215° C.

400MHz $^1$H-NMR (CDCl$_3$,TMS,ppm): δ1.66(2H,m), 1.74(4H,m), 1.79(6H,m), 2.28(3H, s), 2.46(4H,m), 4.65(1H, m), 7.05(2H,d,J=8.1Hz), 7.06(1H,d,J$_{HF}$=10.2Hz), 7.32(2H, d,J=8.1Hz), 7.67(1H,brs), 7.82(1H,d, J$_{HF}$=7.0Hz), 7.89(1H, brs).

IR (KBr disk, cm$^{-1}$): 820, 861, 1190, 1250, 1258, 1322, 1408, 1490, 1518, 1530, 1602, 1644, 2940, 3280.

EXAMPLE 78

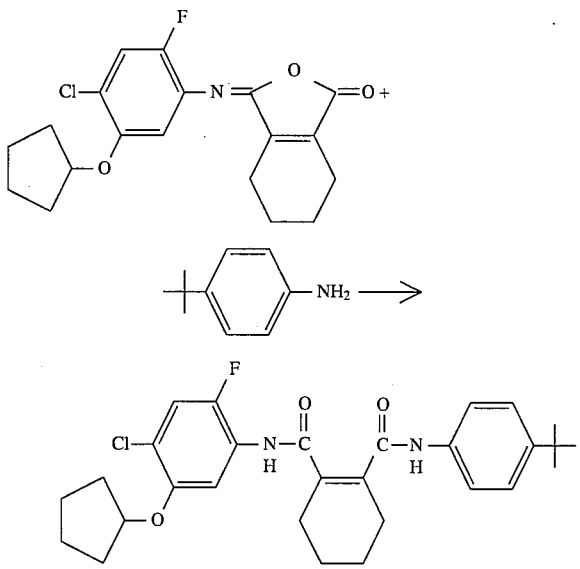

N-(2-Fluoro-4-chloro-5-cyclopentyloxyphenyl)- 3,4,5,6-tetrahydroisophthalimide (1.00 g, 2.75 mmol), 4-tert-butylaniline (0.410 g, 2.75 mmol), and benzene (10 ml) as a solvent were placed into a round bottom flask (50 cc) and stirred for 3 hours at room temperature. After completion of the reaction, the reaction mixture was poured into 1N hydrochloric acid (50 ml), and the mixture was extracted with chloroform (40 ml×3 portions). After drying the organic layer over anhydrous magnesium sulfate, the drying agent was removed, and the solvent was distilled off under reduced pressure. The precipitated crystals were isolated by filtration and washed with hexane to obtain N-( 2-fluoro-4-chloro-5-cyclopentyloxyphenyl)-N'-(4-tert-butylphenyl)-3,4,5,6-tetrahydrophthalamide as white crystals (0.533 g, 37.8% yield).

Melting point: 192°–197° C.

400MHz $^1$H-NMR (CDCl$_3$,TMS,ppm): δ1.26(9H,s), 1.5–1.8(12H,m), 2.45(4H,m), 4.65(1H,m), 7.06(1H, d, J$_{HF}$=10.1Hz), 7.27(2H,d,J=8.5Hz), 7.36(2H,d,J=8.5Hz), 7.71(1H, brs),7.89(1H,d, J$_{HF}$=7.0Hz), 7.93(1H,brs).

IR (KBr disk, cm$^{-1}$): 835, 862, 1190, 1250, 1264, 1322, 1362, 1410, 1490, 1518, 1604, 1645, 2960, 3290.

EXAMPLE 79

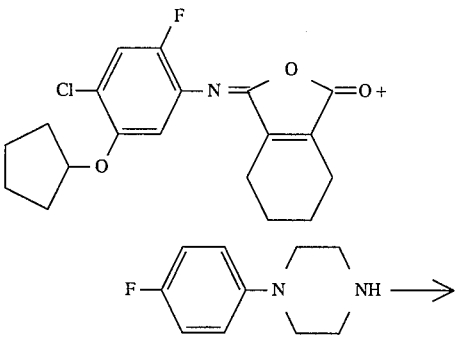

-continued

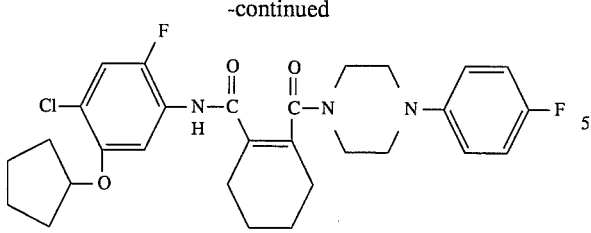

N-(2-Fluoro-4-chloro-5-cyclopentyloxyphenyl)- 3,4,5,6-tetrahydroisophthalimide (0.500 g, 1.37 mmol), 1-(4-fluorophenyl)piperazine (0.250 g, 1.39 mmol) and benzene (10 ml) as a solvent were placed into a round bottom flask (25 cc) and stirred 45 minutes at room temperature. After completion of the reaction, the solvent was distilled off under reduced pressure, and the resulting oily substance was crystallized from hexane to obtain N-(2-fluoro-4-chloro-5-cyclopentyloxyphenyl)-N',N'-{N''-(4-fluorophenyl)diethyleneimino} -3,4,5,6-tetrahydrophthalamide as white crystals (0. 651 g, 87.3% yield).

Melting point: 116°–118° C.

400MHz $^1$H-NMR (CDCl$_3$,TMS,ppm): δ1.52(2H,m), 1.68(4H,m), 1.76(6H,m), 2.37(4H,m), 2.67–3.14(4H,m), 3.40–4.14(4H,m), 4.59(1H,m), 6.73(1H,ddd,$J_{HF}$=6.8Hz and J=6.8 and 2.3Hz), 6.76(1H,ddd, $J_{HF}$=6.8Hz and J=6.8 and 2.3Hz), 6.93(1H,ddd, $J_{HF}$=12.9Hz and J=6.8 and 2.3Hz), 6.94(1H, ddd, $J_{HF}$=12.9Hz and J=6.8 and 2.3Hz), 7.12(1H, d,$J_{HF}$=10.2Hz), 8.04(1H,d,$J_{HF}$=7.2Hz), 8.23(1H,brs).

IR (KBr disk, cm$^{-1}$): 830, 1000, 1175, 1190, 1218, 1238, 1252, 1285, 1405, 1438, 1490, 1510, 1528, 1618, 1678, 2840, 2870, 2950, 3330.

EXAMPLE 80

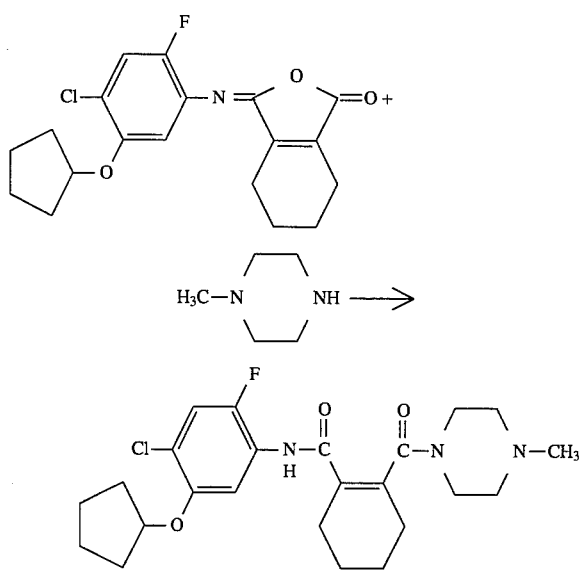

N-(2-Fluoro-4-chloro-5-cyclopentyloxyphenyl)- 3,4,5,6-tetrahydroisophthalimide (0.490 g, 1.35 mmol), N-methylpiperazine (0.222 g, 2.22 mmol), and benzene (8 ml) as a solvent were placed into a round bottom flask (25 cc) and stirred 30 minutes at room temperature. After completion of the reaction, the solvent was distilled off under reduced pressure, and the resulting oily substance were crystallized from hexane to obtain N-(2-fluoro-4-chloro- 5-cyclopentyloxyphenyl)-N',N'-(N''-methyldiethyleneimino)- 3,4,5,6-tetrahydrophthalamide as white crystals (0.530 g, 84.6% yield). The melting point and the spectral data thereof are shown in Example 49.

EXAMPLE 81

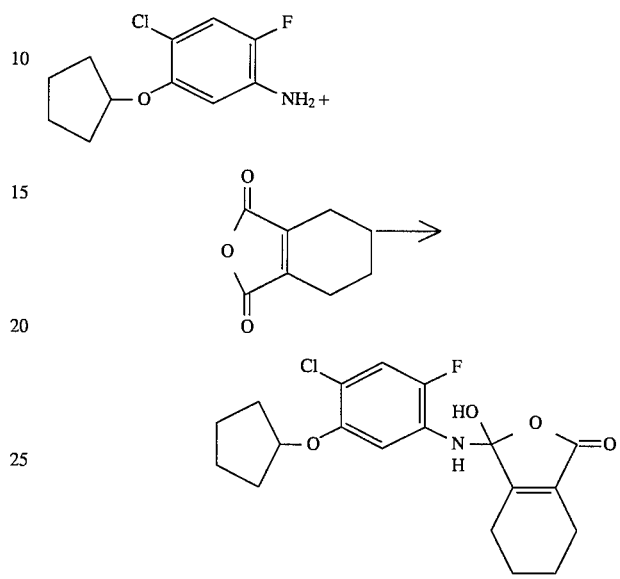

2-Fluoro-4-chloro-5-cyclopentyloxyaniline (12.3 g, 53.6 mmol), 3,4,5,6-tetrahydrophthalic anhydride (8.15 g, 53.6 mmol), and acetic acid (20 ml) and hexane (20 ml) as solvents were placed in a round bottom flask (100 cc) and stirred at room temperature for 1 hour. After completion of the reaction, the precipitated crystals were isolated by filtration. The crystals were washed with hexane and thoroughly dried to obtain an N-(2-fluoro-4-chloro-5-cyclopentyloxyphenyl)- 3,4,5,6-tetrahydroisophthalimidohydroxy compound as white crystals (16.1 g, 78.8% yield).

Melting point: 98.0°–99.0° C.

$^1$H-NMR (CDCl$_3$,TMS,ppm): δ1.61(2H,m), 1.81(4H,m), 1.86(6H, m), 2.42(4H,m), 3.60(2H,brs), 4.75(1H,m), 6.36(1H,d,$J_{HF}$=8.2Hz), 6.98(1H,d,$J_{HF}$=10.4Hz).

IR (KBr disk, cm$^{-1}$): 3250, 2950, 1700, 1670, 1630, 1610, 1510, 1420, 1390, 1285, 1260, 1190, 870, 720.

Elementary Analysis (calcd.; C$_{19}$H$_{21}$FNO$_4$,%): C; 59.78(59.76), H; 5.64(5.55), N; 3.62(3.67).

EXAMPLE 82

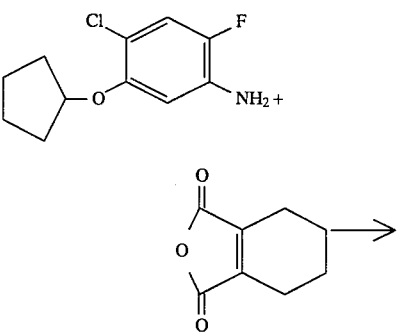

-continued

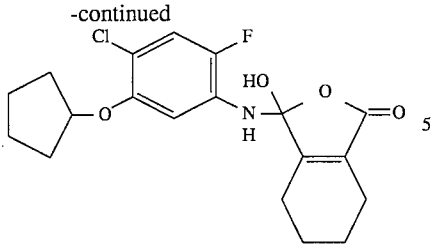

2-Fluoro-4-chloro-5-cyclopentyloxyaniline (3.47 g, 15.1 mmol), 3,4,5,6-tetrahydrophthalic anhydride (2.30 g, 15.1 mmol), and acetone (30 ml) as a solvent were placed into a round bottom flask (50 cc) and stirred 2 hours and 30 minutes at 45° C. After completion of the reaction, the mixture was poured into 2N hydrochloric acid (30 ml), and the precipitated crystals were isolated by filtration and thoroughly dried. The crystals were further washed with hexane to obtain an N-(2-fluoro-4-chloro-5-cyclopentyloxyphenyl)- 3,4,5,6-tetrahydrophthalimidehydroxy compound as white crystals (4.88 g, 84.6% yield). The spectral data, etc. thereof are shown in Example 81.

EXAMPLE 83

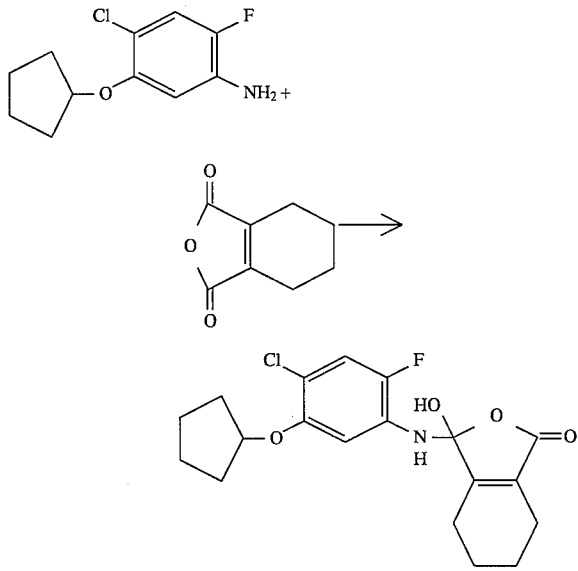

2-Fluoro-4-chloro-5-cyclopentyloxyaniline (2.56 g, 11.2 mmol), 3,4,5,6-tetrahydrophthalic anhydride (1.72 g, 11.3 mol) and benzene (10 ml) as a solvent were placed into a round bottom flask (50 cc) and stirred one hour at room temperature. After completion of the reaction, the reaction mixture was poured into 2N hydrochloric acid (20 ml) and extracted with ethyl acetate (20 ml×3 portions). The organic layer was dried over anhydrous magnesium sulfate, and, after removing the drying agent, the solvent was distilled off under reduced pressure. Upon measuring the NMR spectrum of the resulting crude product, absorptions assigned to N-(2-fluoro-4-chloro-5 -cyclopentyloxypheyl)-3,4,5,6-tetrahydrophthalamic acid represented by the general formula (VII') were confirmed in addition to the object product, N-(2-fluoro-4-chloro-5-cyclopentyoxyphenyl)- 3,4,5,6-tetrahydroisophthalimidohydroxy compound. The spectral data are shown below and are characterized in that the two protons on the phenyl ring are markedly shifted to a low magnetic filed, as compared with the isoimidohydroxy compound.

$^1$H-NMR (CDCL$_3$+DMSO-d$_6$, TMS, pp): δ1.83 (12H,m), 2.21–2.67 (4H, m), 4.75(1H,m), 7.10(1H,d,J$_{HF}$=10.5Hz), 8.02(1H,d, J$_{HF}$=7.5Hz).

Then, the resulting crude product was recrystallized from ethyl acetate/hexane to obtain an N-(2-fluoro-4-chloro-5-cyclopentyloxyphenyl)-3,4,5,6-tetrahydroisophthalimidohydroxy compound as white crystals (3.54 g, 83.1% yield). In this product, phthalamic acid was not observed. The spectral data, etc. are shown in Example 81.

EXAMPLE 84

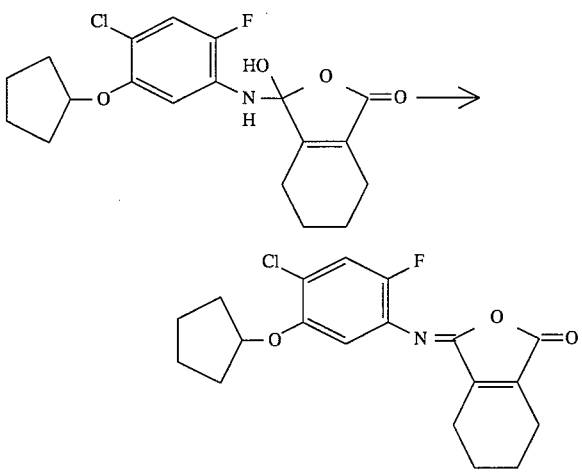

2-Fluoro-4-chloro-5-cyclopentyloxyaniline (3.50 g, 15.2 mmol) was placed into a round bottom flask (100 cc), and acetic acid (15 ml) was added thereto to dissolve it. Then, 3,4,5,6-tetrahydrophthalic anhydride (2.50 g, 16.4 mmol) was added thereto under ice-cooling, and the mixture was stirred for 15 minutes. After completion of the reaction, the mixture was poured into 2N hydrochloric acid (20 ml) and extracted with ethyl acetate (30 ml×3 portions). The organic layer was dried over anhydrous magnesium sulfate, and, after removing the drying agent, the solvent was distilled off under reduced pressure. The resulting crude product (production of a small amount of N-(2-fluoro-4-chloro-5-cyclopentyloxyphenyl)-3,4,5,6-tetrahydrophthalamic acid in the crude product was confirmed by NMR) was recrystallized from ethyl acetate/hexane to obtain an N-(2-fluoro-4-chloro-5-cyclopentyloxyphenyl)-3,4,5,6-tetrahydroisophthalimidohydroxy compound as white crystals (4.08 g, 70.1% yield). The spectral data, etc. thereof are shown in Example 81.

EXAMPLE 85

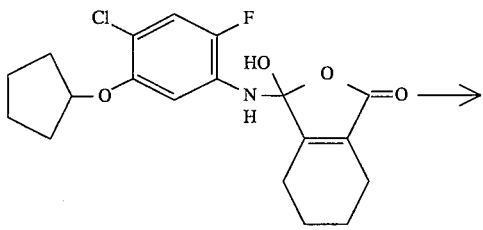

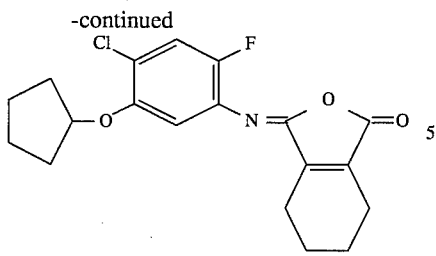

An N-(2-fluoro-4-chloro-5-cyclopentyloxyphenyl)- 3,4,5,6-tetrahydroisophthalimidohydroxy compound (5.00 g, 13.1 mmol) and benzene (20 ml) as a solvent were placed into a round bottom flask (100 cc) and dissolved. To the solution was added N,N'-dicyclohexylcarbodiimide (2.70 g, 13.1 mmol) under ice cooling, and the temperature of the mixture was slowly elevated to room temperature, followed by stirring for 24 hours. After completion of the reaction, the precipitated N,N'-dicyclohexylurea was removed by filtration through Celite, and the filtrate was distilled off under reduced pressure to obtain a crude product. The product was isolated and purified using silica gel column (ethyl acetate/hexane=1/7) to obtain N-( 2-fluoro-4-chloro-5-cyclopentyloxyphenyl)-3,4,5,6-tetrahydroisophthalimide as light yellow crystals (3,09 g, 64.8% yield).

Melting point: 98.0°–99.0° C.

$^1$H-NMR (CDCl$_3$,TMS,ppm): δ1.64(2H,m), 1.84(2H,m), 1.90(8H, m), 2.42(2H,m), 2.59(2H,m), 4.80(1H,m), 6.86(1H, d, J$_{HF}$=7.2Hz), 7.15(1H,d, J$_{HF}$=9.6Hz).

IR (KBr disk, cm$^{-1}$): 2950, 2890, 1810, 1780, 1680, 1660, 1495, 1390, 1265, 1190, 1020, 970, 900, 860, 850.

Elementary Analysis (Calcd values; C$_{19}$H$_{19}$ClFNO$_3$,%: C; 62.84(62.73), H; 5.28(5.26), N; 3.84(3.85).

MS(m/e, relative intensity): 366(M$^+$+3,0.47), 3.65(M$^+$+2, 2.80), 364(M$^+$+1,1.80), 363(M$^+$,7.95), 295(100), 216(3.15), 108(14.38), 79(32.18), 69(10.71), 41(49.27).

EXAMPLE 86

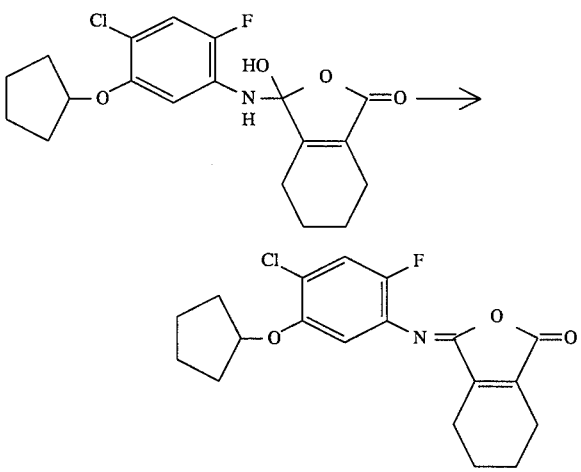

An N-(2-fluoro-4-chloro-5-cyclopentyloxyphenyl)- 3,4,5,6-tetrahydroisophthalimidohydroxy compound (5.80 g, 15.2 mmol) and chloroform (30 ml) as a solvent were placed into a round bottom flask (100 cc) and dissolved. To the solution was added N,N'-dicyclohexylcarbodiimide (3.20 g, 15.5 mmol) under ice cooling, and the temperature of the mixture was slowly elevated to room temperature, followed by stirring for 24 hours. After completion of the reaction, the precipitated N,N'-dicyclohexylurea was removed by filtration through Celite, and the filtrate was distilled off under reduced pressure to obtain a crude product. The product was isolated and purified using silica gel column (ethyl acetate/hexane=1/6) to obtain N-(2-fluoro-4-chloro-5-cyclopentyloxyphenyl)-3,4,5,6-tetrahydroisophthalimide as light yellow crystals (3,59 g, 64.9% yield). The spectral data, etc. are shown in Example 85.

EXAMPLE 87

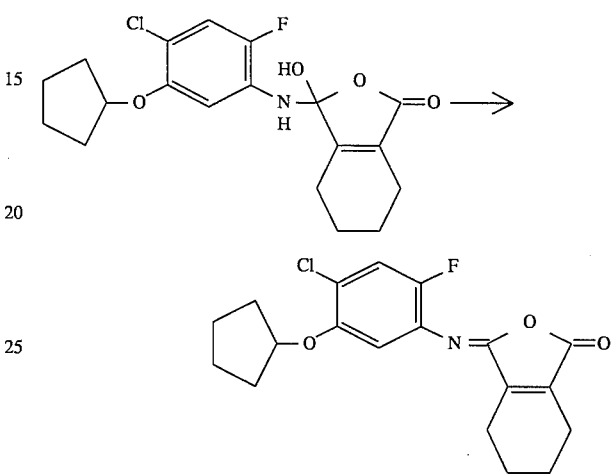

An N-(2-fluoro-4-chloro-5-cyclopentyloxyphenyl)- 3,4,5,6-tetrahydroisophthalimidohydroxy compound (8.00 g, 20.9 mmol), N,N'-dicyclohexylcarbodiimide (4.32 g, 20.9 mmol) and toluene (80 ml) as a solvent were placed into a round bottom flask (100 cc) and stirred at room temperature for 24 hours. After completion of the reaction, the precipitated N,N'-dicyclohexylurea was removed by filtration through Celite, and the filtrate was distilled off under reduced pressure to obtain a crude product. The product was isolated and purified using silica gel column (ethyl acetate/hexane= 1/7) to obtain N-(2-fluoro-4-chloro- 5-cyclopentyloxyphenyl)-3,4,5,6-tetrahydroisophthalimide as light yellow crystals (2.57 g, 33.7% yield). The spectral data, etc. are shown in Example 85.

EXAMPLE 88

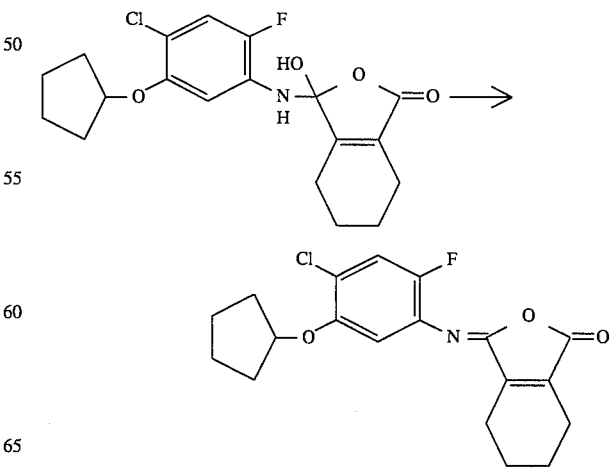

An N-(2-fluoro-4-chloro-5-cyclopentyloxyphenyl)- 3,4,5,6-tetrahydroisophthalimidohydroxy compound (3.00 g, 7.86 mmol) and benzene (20 ml) as a solvent were placed into a round bottom flask (100 cc) and dissolved. To the solution was added N,N'-diisopropylcarbodiimide (1.30 g, 10.3 mmol) under ice cooling, and the temperature of the mixture was slowly elevated to room temperature, followed by stirring for 24 hours. After completion of the reaction, the precipitated N,N'-diisopropylurea was removed by filtration through Celite, and the filtrate was distilled off under reduced pressure to obtain a crude product. The product was isolated and purified using silica gel column (ethyl acetate/hexane=1/5) to obtain N-(2-fluoro-4-chloro-5-cyclopentyloxyphenyl)-3,4,5,6-tetrahydroisophthalimide as light yellow crystals (1.08 g, 37.8% yield). The spectral data, etc. are shown in Example 85.

EXAMPLE 89

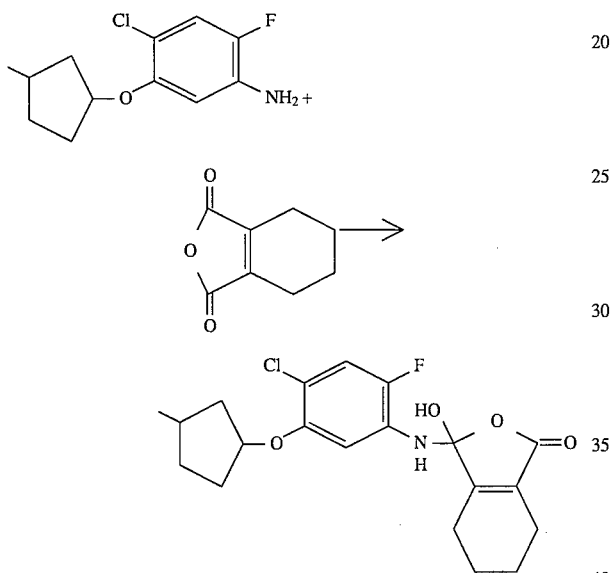

2-Fluoro-4-chloro-5-(3-methylcyclopentyl)oxyaniline (2.80 g, 11.5 mmol), 3,4,5,6-tetrahydrophthalic anhydride (1.74 g, 11.4 mmol) and acetone (50 ml) as a solvent were placed into a round bottom flask (100 cc) and stirred for 45° C. for 7 hours. After completion of the reaction, the reaction mixture was poured into 1N hydrochloric acid (50 ml), and extracted with ethyl acetate (50 ml×3 portions). The organic layer was dried over anhydrous magnesium sulfate, and, after removing the drying agent, the solvent was distilled off under reduced pressure. The resulting crude product was recrystallized from ether/hexane to obtain an N-{2-fluoro-4-chloro-5-(3-methylcyclopentyl)oxyphenyl}-3,4,5,6-tetrahydroisophthalimidohydroxy compound as white crystals (2.90 g, 63.8% yield).

Melting point: 83.0°–85.0° C.

$^1$H-NMR (CDCl$_3$,TMS,ppm): δ1.02 and 1.09(total 3H, each d, J=6.7 and 6.7Hz), 1.1–1.5(2H,m), 1.81(6H,m), 1.9–2.12(2H,m), 2.27(1H,m), 2.43(4H,m), 3.75(2H, brs), 4.64 and 4.68 (total 1H, each ), 6.340 and 6.343(total 1H, each d, J$_{HF}$=8.2 and 8.2Hz), 6.993 and 6.997 (total 1H, each d, J$_{HF}$=10.4 and 10.4Hz).

IR (KBr disk, cm$^{-1}$): 3200, 2925, 2850, 1690, 1630, 1600, 1530, 1480, 1400, 1280, 1250, 1180, 860.

Elementary Analysis (Calcd values; C$_{20}$H$_{23}$ClFNO$_4$, % ): C; 60.63(60.68), H; 5.99(5.86), N; 3.59(3.54).

EXAMPLE 90

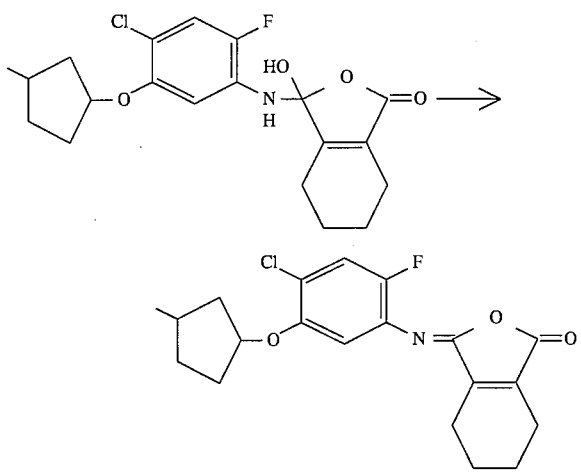

An N-{2-fluoro-4-chloro-5-(3-methylcyclopentyl)oxyphenyl}-3,4,5,6-tetrahydroisophthalimidohydroxy compound (3.00 g, 7.58 mmol) and chloroform (30 ml) as a solvent were placed into a round bottom flask (100 cc) and dissolved. To the solution was added N,N'-dicyclohexylcarbodiimide (1.56 g, 7.56 mmol) under ice cooling, and the temperature of the mixture was slowly elevated to room temperature, followed by stirring for 24 hours. After completion of the reaction, the precipitated N,N'-dicyclohexylurea was removed by filtration through Celite, and the filtrate was distilled off under reduced pressure to obtain a crude product. The product was isolated and purified using silica gel column (ethyl acetate/hexane=1/8) to obtain N-{2-fluoro-4-chloro-5-(3-metylcyclopentyl)oxyphenyl}-3,4,5,6-tetrahydroisophthalimide as light yellow crystals (0.21 g, 7.3% yield).

Melting point: 100.0°–101.0° C.

$^1$H-NMR (CDCl$_3$,TMS,ppm): δ1.03 and 1.10(total 3H, each d, J=4.2 and 6.7Hz), 1.15–1.50(2H,m), 1.83(4H,m), 1.97(2H,m), 4.70 and 4.75(total 1H,m), 6.83 and 6.85 (total 1H, each d, J$_{HF}$=7.14 and 7.15Hz), 7.14 and 7.17 (total 1H, each d, J$_{HF}$=9.63 and 9.63Hz).

IR (KBr disk, cm$^{-1}$): 2950, 1790, 1680, 1500, 1395, 1270, 1180, 1020, 910, 880, 850.

Elementary Analysis (Calcd values; C$_{20}$H$_{21}$ClFNO$_3$, %): C; 63.56(63.57), H; 5.78(5.61), N; 3.82(3.71)

MS(m/e, relative intensity): 380(M$^+$+3,0.25), 379(M$^+$+2, 2.05), 378(M$^+$+1,1.40), 377(M+,6.06), 295(100), 224(3.83), 143(3.80), 108(11.66), 107(10.0), 99(6.29), 79(26.92), 56 (26.64), 55 (36.29), 41(37.10).

EXAMPLE 91

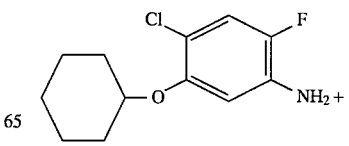

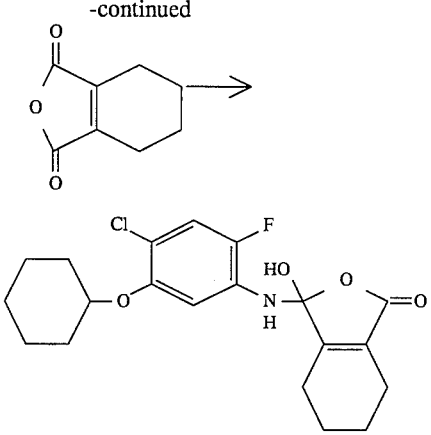

2-Fluoro-4-chloro-5-cyclohexyloxyaniline (1.64 g, 6.73 mmol), 3,4,5,6-tetrahydrophthalic anhydride (1.02 g, 6.70 mmol) and acetone (25 ml) as a solvent were placed into a round bottom flask (50 cc) and stirred for 45° C. for 7 hours. After completion of the reaction, the reaction mixture was poured into 1N hydrochloric acid (50 ml), and extracted with ethyl acetate (30 ml×3 portions). The organic layer was dried over anhydrous magnesium sulfate, and, after removing the drying agent, the solvent was distilled off under reduced pressure. The resulting crude product was recrystallized from ether/hexane to obtain an N-(2-fluoro-4-chloro-5-cyclohexyloxyphenyl)-3,4,5,6-tetrahydroisophthalimidohydroxy compound as greyish white crystals (1.89 g, 70.9% yield).

Melting point: 81.0°–83.0° C.

$^1$H-NMR (CDCl$_3$,TMS,ppm): δ1.33(3H,m), 1.58(3H,m), 1.81(6H, m), 1.93(2H,m), 2.43(4H,m), 3.70(2H,brs), 4.11(1H, m), 6.41(1H,d, J$_{HF}$=8.3Hz), 7.00(1H,d, J$_{HF}$=10.4Hz).

IR (KBr disk, cm$^{-1}$): 3200, 2920, 1690, 1630, 1540, 1490, 1410, 1280, 1260, 1190, 950.

Elementary Analysis (Calcd values; C$_{20}$H$_{23}$ClFNO$_4$): C; 60.45(60.68), H; 5.88(5.86), N; 3.46(3.54).

EXAMPLE 92

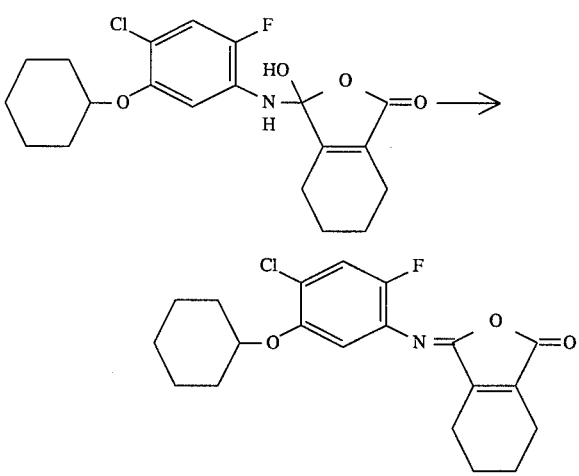

An N-(2-fluoro-4-chloro-5-cyclohexyloxyphenyl)- 3,4,5,6-tetrahydroisophthalimidohydroxy compound (3.50 g, 8.84 mmol) and chloroform (60 ml) as a solvent were placed into a round bottom flask (100 cc) and dissolved. To the solution was added N,N'-dicyclohexylcarbodiimide (1.82 g, 8.82 mmol) under ice cooling, and the temperature of the mixture was slowly elevated to room temperature, followed by stirring for 24 hours. After completion of the reaction, the precipitated N,N'-dicyclohexylurea was removed by filtration through Celite, and the filtrate was distilled off under reduced pressure to obtain a crude product. The product was isolated and purified using silica gel column (ethyl acetate/hexane=1/10) to obtain N-(2-fluoro-4-chloro-5-cyclohexyloxyphenyl)-3,4,5,6-tetrahydroisophthalimide as light yellow crystals (2.19 g, 65.6% yield).

Melting point: 78.0°–80.0° C.

$^1$H-NMR (CDCl$_3$,TMS,ppm): δ1.35(2H,m), t.53(1H,m), 1.61(3H, m), 1.83(6H,m), 1.94(2H,m), 2.42(2H,m), 2.57(2H, m), 4.19(1H,m), 6.87(1H,d,J$_{HF}$=7.2Hz), 7.15(1H, d, J$_{HF}$=9.7Hz).

IR (KBr disk, cm$^{-1}$): 2900, 1770, 1665, 1490, 1270, 1190, 1050, 1015, 890, 840.

Elementary Analysis (Calcd values; C$_{20}$H$_{21}$ClFNO$_3$, %): C; 63.76(63.57), H; 5.70(5.61), N; 3.91(3.71).

MS(m/e, relative intensity): 380(M$^+$+3,0.26), 379(M$^+$+2, 2.20), 378(M$^+$+1,1.53), 377 (M$^+$, 6.44), 297 (33.59), 296(16.72), 295(100), 108(11.74), 79(27.21), 54(11.89), 34(36.06).

EXAMPLE 93

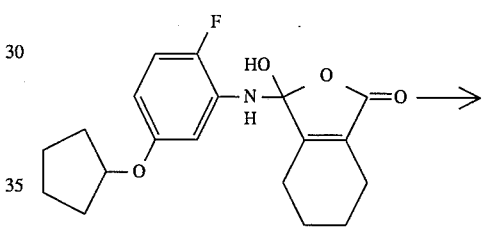

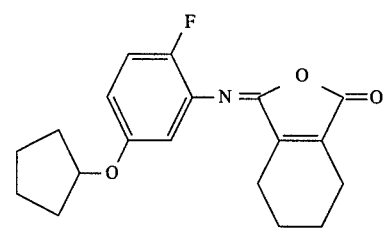

An N-(2-fluoro-4-chloro-5-cyclopentyloxyphenyl)- 3,4,5, 6-tetrahydroisophthalimidohydroxy compound (813 mg, 2.34 mmol) and chloroform (5 ml) as a solvent were placed into a round bottom flask (25 cc) and dissolved. To the solution was added N,N'-dicyclohexylcarbodiimide (483 mg, 2.34 mmol) under ice cooling, and the mixture was stirred for 30 minutes. Then, the temperature of the mixture was slowly elevated to room temperature, followed by stirring for 18 hours. After completion of the reaction, the precipitated N,N-dicyclohexylurea was removed by filtration through Celite, and the filtrate was distilled off under reduced pressure to obtain a crude product (932 mg) as a red oily substance. The product was isolated and purified using silica gel column (ethyl acetate/hexane=1/9) to obtain the desired N-(2-fluoro-5-cyclopentyloxyphenyl)- 3,4,5,6-tetrahydroisophthalimide as a yellow oily substance (583 g, 1.77 mmol, 75.5% yield).

$^1$H-NMR (CDCl$_3$,TMS,ppm): δ1.44–1.97(12H,m), 2.27–2.64(4H,m), 4.69(1H,m), 6.82(1H,d,J=6.6Hz), 6.74–6.97(2H,m).

REFERENCE EXAMPLE 1

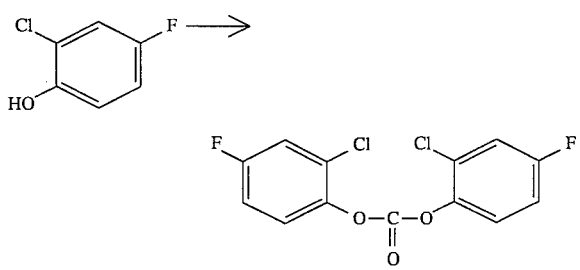

2-Chloro-4-fluorophenol (4.4 Kg, 30 mol), triethylbenzylammonium chloride (17.1 g) and methylene chloride (7 liters) were placed in a 20L three-necked flask equipped with a stirrer and a dropping funnel and cooled in an ice bath. Then, a 5N aqueous sodium hydroxide solution (6 liters) was slowly added thereto, followed by stirring vigorously. Then, trichloromethyl chloroformate (885 ml, 7.35 mol) was added dropwise thereto slowly over about 6 hours at room temperature, and, after dropwise addition, the reaction solution was stirred overnight. After completion of the reaction, the organic layer was separated, and the aqueous layer was extracted with methylene chloride (1000 ml×2 portions). The organic layers were combined, washed with a 1N aqueous sodium hydroxide solution (4 liters) and water (5 liters), and dried over anhydrous magnesium sulfate. After removing the drying agent by filtration, the solvent was distilled off from the organic layer under reduced pressure to obtain bis(2-chloro-4-fluorophenyl)carbonate as a white solid (4.9 Kg, 15.4 mol, 100% yield).

Melting point: 91.0°–92.0° C.

$^1$H-NMR (CDCl$_3$,TMS,ppm): δ6.87–7.4(6H,m).

IR (KBr disk, cm$^{-1}$): 1180, 1250, 1290, 1500, 1605, 1780.

REFERENCE EXAMPLE 2

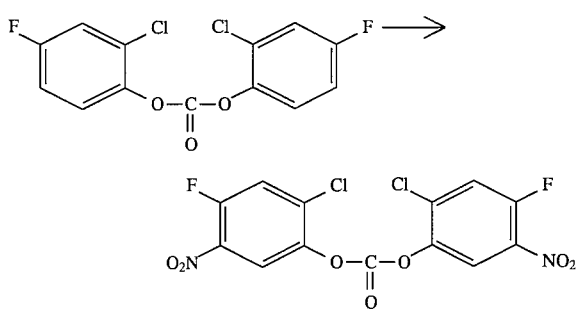

Bis(2-chloro-4-fluorophenyl)carbonate (801 g, 2.5 mol) was placed in a 5L three-necked flask equipped with a dropping funnel and a stirrer, and sulfuric acid (98%, 2000 ml) was added thereto, followed by thoroughly stirring. Then, while vigorously stirring, a mixed acid prepared from nitric acid (60%, 400 ml) and sulfuric acid (98%, 400 ml) was dropwise added thereto from the dropping funnel slowly so as not to elevate the reaction temperature over 7 hours. Aftr dropwise addition, the reaction mixture was further stirred vigorously for one hour, and cold water (5000 ml) was added thereto to obtain a precipitated white solid of bis(2-chloro-4-fluoro-5-nitrophenyl)carbonate (1026 g, 2.5 mol, 100% yield). The product can be isolated purely as white needle crystals by recrystallization from toluene or ethyl acetate.

Melting point: 165.0°–165.5° C.

$^1$H-NMR (CDCl$_3$,TMS,ppm): δ7.58(2H,d, J$_{HF}$=9.9Hz), 8.25(2H,d, J$_{HF}$=8.3Hz).

IR (KBr disk, cm$^{-1}$): 1180, 1240, 1355, 1495, 1540, 1605, 1797.

REFERENCE EXAMPLE 3

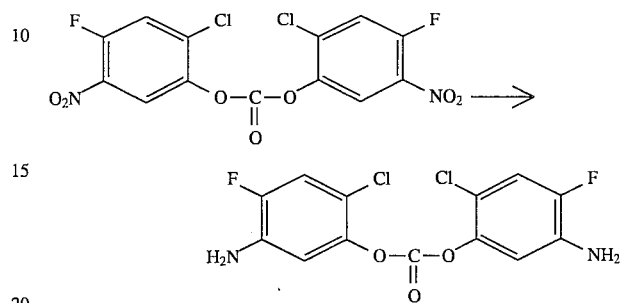

Bis(2-chloro-4-fluoro-5-nitrophenyl)carbonate (1.2 Kg, 2.9 mol), toluene (7 liters) as a solvent and 5% Pd/C (200 g) as a catalyst were placed in a 10L three-necked flask equipped with a stirrer, and hydrogen gas was introduced while vigorously stirring. Heat generated as the reaction proceeded, and the reaction temperature was maintained at 60° to 70° C. by introducing hydrogen at such a rate that the hydrogen gas did not discharge from the system. After completion of the reaction, the reaction mixture was heated (60°–70° C.), and the catalyst was separated by filtration. The organic layer of the filtrate was separated and dried over anhydrous magnesium sulfate. The drying agent was separated by filtration, and the solvent was distilled off under reduced pressure to obtain bis(2-chloro-4-fluoro-5-aminophenyl)carbonate as a white solid (1.01Kg, 2.89 mol, 99.6% yield).

Melting point: 136.0°–137.0° C.

$^1$H-NMR (CDCl$_3$, TMS, pp): δ3.83 (4H, brs), 6.71 (2H, d, J$_{HF}$=8.5Hz), 7.08 (2H, d, J$_{HF}$=10.5Hz).

IR (KBr disk, cm$^{-1}$): 1155, 1190, 1235, 1260, 1510, 1640, 1780, 3500.

REFERENCE EXAMPLE 4

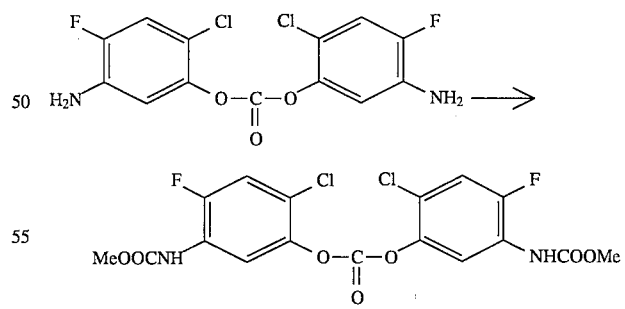

Bis(2-chloro-4-fluoro-5-aminophenyl)carbonate (1.75 Kg, 5.0 mol), potassium carbonate (1.04 Kg, 7.5 mol) and toluene (6 liters) as a solvent were placed in a 10L three-necked flask equipped with a stirrer and a dropping funnel. To the resulting solution was added dropwise methyl chloroformate (770 ml, 9.9 mol), and the mixture was stirred at 60°–70° C. (a bath temperature) for 5 hours. After completion of the reaction, the reaction mixture was filtered, washed with toluene, 1N hydrochloric acid and water, and thoroughly dried to obtain bis(2-chloro-4-fluoro- 5-methoxycarbonylaminophenyl)carbonate as a white solid (2.10 Kg, 4.51 mol, 90.2% yield).

Melting point: 212.0°–214.0° C.

$^1$H-NMR (CDCl$_3$,TMS,ppm): δ3.80(6H,s), 6.87(2H,brs), 7.19(2H, d, J$_{HF}$=10.2Hz), 8.22 (2H, d, J$_{HF}$=8.3Hz).

IR (KBr disk, cm$^{-1}$): 1217, 1240, 1420, 1490, 1553, 1630, 1740, 1790.

REFERENCE EXAMPLE 5

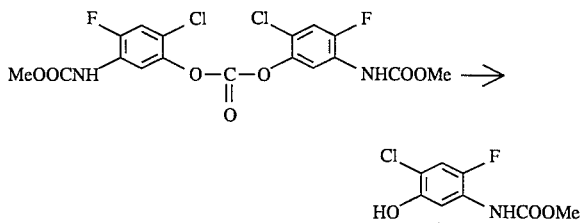

Bis(2-chloro-4-fluoro-5-methoxycarbonylaminophenyl)carbonate (1.28 Kg, 2.76 mol), potassium carbonate (286 g, 2.05 mol) and methanol (2.5 liters) as a solvent were placed in a three-necked flask (5L) and stirred while heating at 50° C. for 1.5 hours. After completion of the reaction, the reaction mixture cooled to room temperature was added to 1N hydrochloric acid (10 liters)/ice (5 Kg) while stirring. The precipitated white solid was filtered and thoroughly dried to obtain methyl N-(2-fluoro-4-chloro- 5-hydroxyphenyl)carbamate (1.20 Kg, 5.46 mol, 99.0% yield).

Melting point: 140.0°–141.0° C.

$^1$H-NMR(CDCl$_3$, TMS, ppm): δ3.79 (3H, s), 5.53 (1H, s), 6.75 (1H, brs), 7.05(1H,d,J$_{HF}$=10.5Hz), 7.82(1H,d,J$_{HF}$=7.5Hz).

IR(KBr disk, cm$^{-1}$): 1250, 1430, 1560, 1630, 1717.

REFERENCE EXAMPLE 6

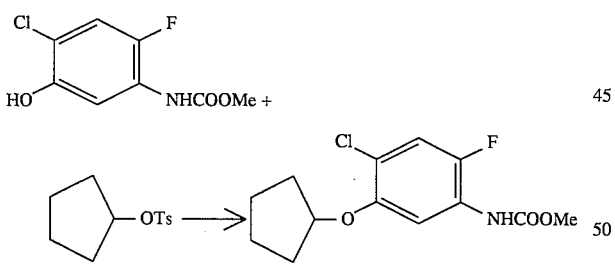

Methyl N-(2-fluoro-4-chloro-5-hydroxyphenyl)carbamate (1.64 Kg, 7.47 mol), cyclopentyl-p-toluenesulfonate (1.80 Kg, 7.48 mol), potassium carbonate (1.03 Kg, 7.46 mol) and potassium iodide (12.3 g, 1.0 mol %) were placed in a 10L three-necked flask equipped with a stirrer and a Dimroth funnel, and, after adding acetone (7.5 liters) as a solvent thereto, the mixture was refluxed under heating for 4 hours. After completion of the reaction, the reaction solution was taken out, and 0.5N hydrochloric acid (20 liters) was added thereto while vigorously stirring. The precipitated methyl N-(2-fluoro- 4-chloro-5-cyclopentyloxyphenyl)carbamate as a white solid (2.0 Kg, 6.95 mol, 93.1% yield) was isolated by filtration and thoroughly dired.

Melting point: 120.0°–123.0° C.

$^1$H-NMR(CDCl$_3$,TMS,ppm): δ1.40–2.10(8H,m), 3.77(3H,s), 4.77(1H,m), 6.82(1H,brs), 7.07(1H,d,J$_{HF}$=10.5Hz), 7.83(1H, d, J$_{HF}$=7.5Hz).

IR(KBr disk, cm$^{-1}$): 1190, 1255, 1415, 1500, 1535, 1714.

REFERENCE EXAMPLE 7

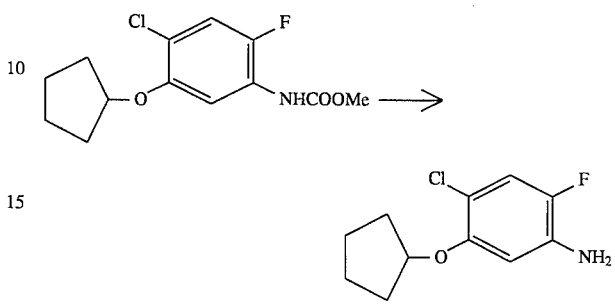

A 4N potassium hydroxide aqueous solution (4.75 liters) was added to an ethanol solution (3 liters) of methyl N-(2-fluoro-4-chloro-5-cyclopentyloxyphenyl)carbamate (2.25 Kg, 7.85 mol), followed by refluxing under heating for 5 hours. After completion of the reaction, the reaction solution was cooled to room temperature, water (5 liters) was added thereto, and the mixture was extracted with toluene (5 liters×2 portions). The organic layer was washed with water and dried over anhydrous magnesium sulfate. The drying agent was separated by filtration, and the filtrate was distilled off under reduced pressure to obtain 2-fluoro-4-chloro-5-cyclopentyloxyaniline as an oily substance (1.75 Kg, 7.62 mol, 98.3% yield). *Boiling point:* 143°–145° C./1.5 mmHg.

$^1$H-NMR(CDCl$_3$,TMS,ppm): δ1.40–2.00(8H,m), 3.72(2H,brs), 4.67(1H,m), 6.39(1H,d,J$_{HF}$=9.0Hz), 7.04(1H, d, J$_{HF}$=11.0Hz).

IR(neat, cm$^{-1}$): 1185, 1245, 1420, 1510, 1630, 3400, 3500.

REFERENCE EXAMPLE 8

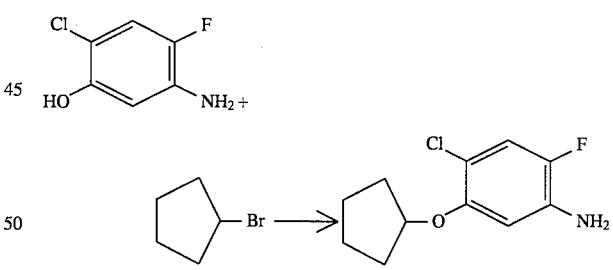

2-Chloro-4-fluoro-5-aminophenol (1.02 g, 6.28 mmol), potassium carbonate (1.72 g, 12.4 mmol), potassium iodide (4.0 mg, 0.024 mmol) and N,N-dimethylformamide (5 ml) as a solvent were placed in a two-necked round bottom flask (25 cc) and stirred at 80° C. for one hour. Then, cyclopentyl bromide (1.00 g, 6.71 mmol) was added thereto, followed by stirring at 80° C. for further 2 hours. After completion of the reaction, the reaction solution was cooled to room temperature, water (20 ml) was added thereto, and the mixuture was extracted with toluene (20 ml×3 portions). The organic layers were combined, washed with water (10 ml) and a saturated aqueous sodium chloride solution (10 ml) and dried over magnesium sulfate. After removing the drying agent, the solvent was distilled off under reduced pressure to obtain 2-fluoro-4-chloro-5-cyclopentyloxyaniline (1.43 g, 6.23 mmol, 99.0% yield). *Boiling point:* 143°–145° C./1.5 mmHg.

$^1$H-NMR(CDCl$_3$,TMS,ppm): δ1.40–2.00(8H,m), 3.72(2H, s), 4.67(1H,m), 6.39(1H,d,J$_{HF}$=9.0Hz), 7.04(1H,d, J$_{HF}$=11.0Hz).

IR(neat, cm$^{-1}$): 3500, 3400, 1630, 1510, 1420, 1245, 1185.

REFERENCE EXAMPLE 9

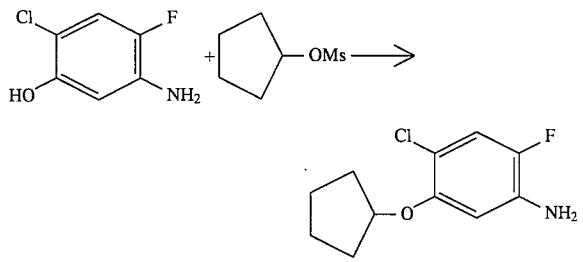

A solution of 2-chloro-4-fluoro-5-aminophenol (10.0 g, 61.9 mmol), cyclopentylmethane sulfonate (10.3 g, 62.9 mmol) and tetrabutylammonium bromide (0.51 g, 1.58 mmol) in toluene (50 ml) was prepared in a 500 cc three-necked flask equipped with a stirrer. Then, a 48% aqueous sodium hydroxide solution (30 ml) was added slowly thereto, followed by stirring while heating at 80° C. for 2 hours. After completion of the reaction, the reaction solution was cooled to room temperature, water (150 ml) was added thereto, and the mixture was extracted with toluene (50 ml×2 portions). The organic layers were combined, washed with water (100 ml×2 portions), and the solvent was distilled off under reduced pressure to obtain 2-fluoro-4-chloro-5-cyclopentyloxyaniline (13.5 g, 59.0 mmol, 95.2% yield, HPLC purity: 98.6%).

REFERENCE EXAMPLE 10

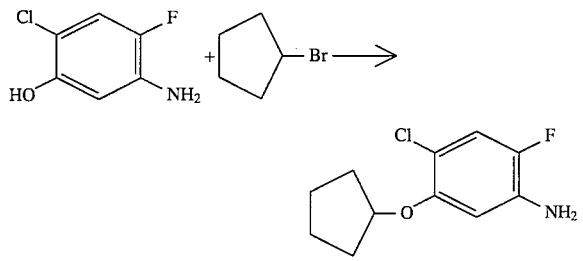

A solution of 2-chloro-4-fluoro-5-aminophenol (75.0 g, 0.464 mol), cyclopentyl bromide (76.3 g, 0.512 mol), tetrabutylammonium bromide (3.03 g, 9.41 mmol) and potassium iodide (776 mg, 4.67 mmol) in toluene (500 ml) was prepared in a 2000 cc three-necked flask equipped with a stirrer. Then, a 40% aqueous sodium hydroxide solution (500 ml) was added slowly thereto, followed by stirring while heating at 80° C. (a warm bath: 85°–90° C.) for 7 hours. After completion of the reaction, the reaction solution was cooled to room temperature, water (500 ml) was added thereto, and the mixture was extracted with toluene (400 ml×2 portions). The organic layers were combined, washed with water (100 ml) and a saturated aqueous sodium chloride solution (100 ml) and dried over anhydrous magnesium sulfate. After removing the drying agent, the solvent was distilled off under reduced pressure to obtain 2-fluoro-4-chloro-5-cyclopentyloxyaniline (87.2 g, 0.380 mol, 81.8% yield).

REFERENCE EXAMPLE 11

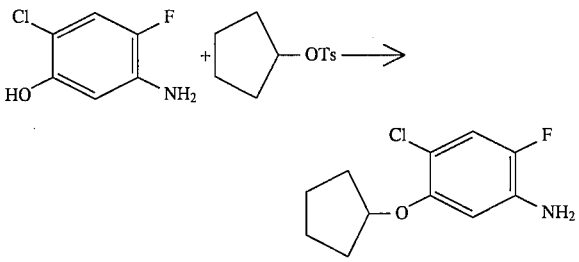

A solution of 2-chloro-4-fluoro-5-aminophenol (1.02 g, 6.29 mmol), cyclopentyl p-toluenesulfonate (1.56 g, 6.50 mmol), tetrabutylammonium bromide (242 mg, 0.75 mmol) and potassium iodide (262 mg, 1.57 mmol) in toluene (20 ml) was prepared in a 50 cc three-necked round bottom flask equipped with a stirrer. Then, a 40% aqueous sodium hydroxide solution (20 ml) was added slowly thereto, followed by stirring while heating at 100° C. for 2 hours. After completion of the reaction, the reaction solution was cooled to room temperature, water (10 ml) was added thereto, and the mixture was extracted with ethyl acetate (20 ml×3 portions). The organic layers were combined, washed with water (10 ml) and a saturated aqueous sodium chloride solution (10 ml) and dried over anhydrous magnesium sulfate. After removing the drying agent, the solvent was distilled off under reduced pressure to obtain 2-fluoro-4-chloro-5-cyclopentyloxyaniline (1.44 g, 6.27 mmol, 99.6% yield).

REFERENCE EXAMPLE 12

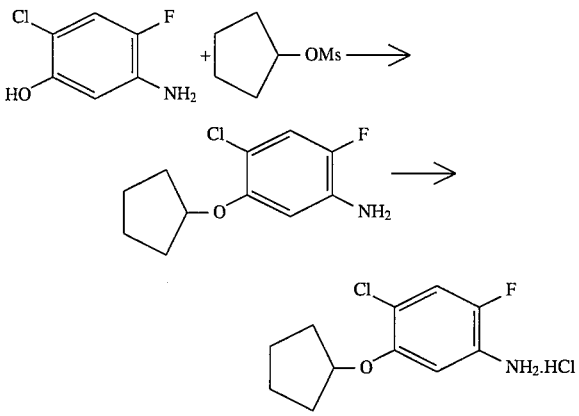

A solution of 2-chloro-4-fluoro-5-aminophenol (1.62 g, 10.0 mmol), cyclopentyl methanesulfonate (1.70 g, 10.4 mmol), tetrabutylammonium bromide (327 mg, 1.01 mmol) and potassium iodide (333 mg, 2.00 mmol) in toluene (10 ml) was prepared in a round bottom flask (50 cc). Then, a 48% aqueous sodium hydroxide solution (7.5 ml) was added slowly thereto, followed by stirring while heating at 80° C. for 1 hours. After completion of the reaction, the reaction solution was cooled to room temperature, water (10 ml) was added thereto, and the mixture was extracted with toluene (20 ml×2 portions). The organic layers were combined, washed with water (10 ml) and a saturated aqueous sodium chloride solution (10 ml), and concentrated hydrochloric acid (1.2 ml) was added to the resulting toluene solution, followed by thoroughly stirring to precipitate 2-fluoro-4-chloro-5-cyclopentyloxyaniline hydrochloride. The resulting white solid was isolated by filtration, washed with ethyl acetate and then toluene, and dried. (Yield, 2.33 g, 8.74 mmol, 87.4% yield).

Melting point: 145.0°–147.0° C.

$^1$H-NMR(CDCl$_3$+DMSO-d$_6$,TMS,ppm): δ1.40–2.10(8H, m), 4.74(1H, m), 7.20(1H, d, J$_{HF}$=9.0Hz), 7.57(1H, d, J$_{HF}$=6.0Hz), 10.40(3H,brs).

IR(Kbr disk, cm$^{-1}$): 2850, 2610, 1500, 1200, 875.

Free 2-fluoro-4-chloro-5-cyclopentyloxyaniline could be obtained by adding an aqueous sodium hydroxide solution to the resulting hydrochloride, followed by extracting with toluene.

REFERENCE EXAMPLE 13

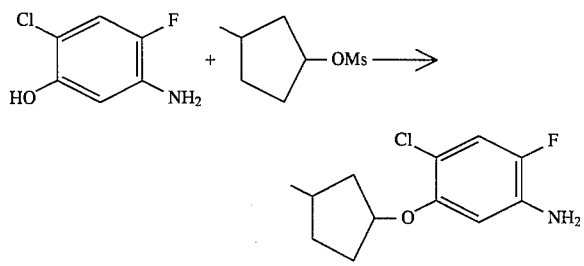

A solution of 2-chloro-4-fluoro-5-aminophenol (3.00 g, 18.6 mmol), 3-methylcyclopentyl p-toluenesulfonate (4.60 g, 18.6 mmol), tetrabutylammonium bromide (300 mg, 0.93 mmol) and potassium iodide (300 mg, 1.81 mmol) in toluene (30 ml) was prepared in a 200 cc three-necked round bottom flask equipped with a stirrer. Then, a 48% aqueous sodium hydroxide solution (30 ml) was added slowly thereto, followed by stirring while heating at 100° C. for 48 hours. After completion of the reaction, the reaction solution was cooled to room temperature, water (50 ml) was added thereto, and the mixture was extracted with ethyl acetate (30 ml×3 portions). The organic layers were combined, washed with water (10 ml) and a saturated aqueous sodium chloride solution (10 ml) and dried over anhydrous magnesium sulfate. After removing the drying agent, the solvent was distilled off under reduced pressure to obtain 2-fluoro-4-chloro-5-(3-methylcyclopentyl)oxyaniline (1.94 g, 7.96 mmol, 42.9% yield) as a brown oily substance.

$^1$H-NMR(CDCl$_3$,TMS,ppm): δ1.02 and 1.10(total 3H, each d, J=6.0Hz), 1.22–2.58(7H, m), 3.75(2H, brs), 4.65(1H, m), 6.33(1H,d,J$_{HF}$=8.0Hz), 6.98(1H,d, J$_{HF}$=10.0Hz).

REFERENCE EXAMPLE 14

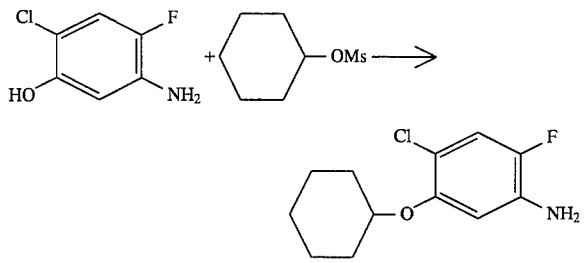

A solution of 2-chloro-4-fluoro-5-aminophenol (1.03 g, 6.40 mmol), cyclohexyl p-toluenesulfonate (1.69 g, 6.66 mmol), tetrabutylammonium bromide (124 mg, 0.38 mmol) and potassium iodide (100 mg, 0.60 mmol) in toluene (15 ml) was prepared in a 100 cc round bottom flask equipped with a stirrer. Then, a 40% aqueous sodium hydroxide solution (15 ml) was added slowly thereto, followed by stirring while heating at 100° C. for 48 hours. After completion of the reaction, the reaction solution was cooled to room temperature, water (10 ml) was added thereto, and the mixture was extracted with ethyl acetate (20 ml×3 portions). The organic layers were combined, washed with water (10 ml) and a saturated aqueous sodium chloride solution (10 ml) and dried over anhydrous magnesium sulfate. After removing the drying agent, the solvent was distilled off under reduced pressure to obtain a crude product (1.06 g). The product was isolated and purified by silica gel column chromatography (ethyl acetate/hexane=1/9) to obtain 2-fluoro-4-chloro-5-cyclohexyloxyaniline (0.75 g, 3.08 mmol, 48.1% yield) as a colorless oily substance.

$^1$H-NMR(CDCl$_3$, TMS, ppm): δ1.15–2.06 (10H, m), 3.46 (1H, brs), 3.95–4.25(1H,m) 6.39(1H,d, J$_{HF}$=9.0Hz), 6.97(1H, d, J$_{HF}$=11.5Hz).

IR(neat, cm$^{-1}$): 3500, 3400, 2940, 2860, 1630, 1505, 1240, 1190.

REFERENCE EXAMPLE 15

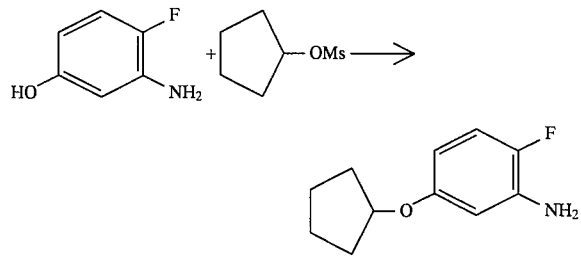

A solution of 3-amino-4-fluorophenol (1.00 g, 7.87 mmol), cyclopentyl methanesulfonate (1.29 g, 7.87 mmol), and tetrabutylammonium bromide (127 mg, 0.394 mmol) in toluene (20 ml) was prepared in a round bottom flask (50 cc). Then, a 48% aqueous sodium hydroxide solution (10 ml) was added slowly thereto, followed by stirring while heating at 80° C. for 3 hours. After completion of the reaction, the reaction solution was cooled to room temperature, water (20 ml) was added thereto, and the mixture was extracted with toluene (20 ml×3 portions). The organic layers were combined and washed with water (20 ml×2 portions). The solvent was distilled off under reduced pressure from the resulting toluene solution to obtain 2-fluoro-5-cyclopentyloxyaniline (660 mg, 3.38 mmol, 43% yield).

$^1$H-NMR(CDCl$_3$,TMS,ppm): δ1.40–2.10(8H,m), 3.85(2H,brs), 4.72(1H,m) 6.24–6.55(3H,m), 6.73(1H,dd, J=5.6 and 9.2Hz).

REFERENCE EXAMPLE 16

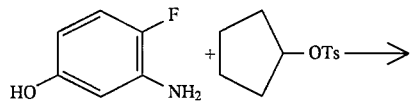

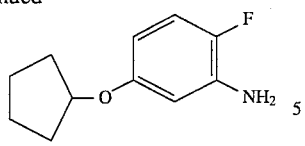

A solution of 3-amino-4-fluorophenol (1.00 g, 7.87 mmol), cyclopentyl p-toluenesulfonate (1.92 g, 7.99 mmol), tetrabutylammonium bromide (127 mg, 0.394 mmol) and potassium iodide (64 mg, 0.39 mmol) in toluene (10 ml) was prepared in a round bottom flask (50 cc). Then, a 48% aqueous sodium hydroxide solution (10 ml) was added slowly thereto, followed by stirring while heating at 80° C. for 3 hours. After completion of the reaction, the reaction solution was cooled to room temperature, water (30 ml) was added thereto, and the mixture was extracted with toluene (20 ml×2 portions). The organic layers were combined, washed with water (20 ml) and a saturated aqueous sodium chloride solution (20 ml). The solvent was distilled off under reduced pressure from the resulting toluene solution. The resulting crude produce was isolated and purified by silica gel column chromatography (developing solvent: hexane/ ethyl acetate=9/1)to obtain the desired 2-fluoro- 5-cyclopentyloxyaniline (1.24 g, 6.33 mmol, 80.5% yield).

REFERENCE EXAMPLE 17

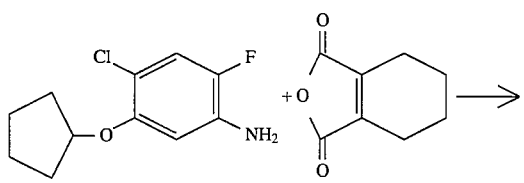

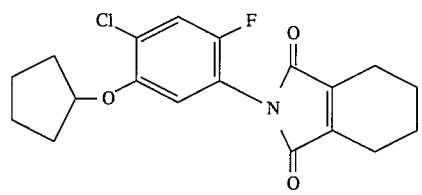

A solution of 2-fluoro-4-chloro-5-cyclopentyloxyaniline (0.50 g, 2.18 mmol) and 3,4,5,6-tetrahydrophthalic anhydride (0.398 g, 2.61 mmol) in ethyl acetate (3.0 ml) was stirred under refluxing for 3 hours. Water (20 ml) was added to the resulting reaction solution, and the mixture was extracted with ethyl acetate (20 ml×3). After drying the organic layer, the solvent was distilled off under reduced pressure, and the resulting light yellow oily substance was purified by silica gel column chromatography (developing solvent: hexane/ethyl acetate=8/1) to obtain N-(2-fluoro-4-chloro-5-cyclopentyloxyphenyl)-3,4,5,6-tetrahydrophathalimide as a colorless transparent oily substance (0.513 g, 1.41 mmol, 65% yield). The product was recrystallized by adding ethanol (1.0 ml) thereto to obtain the product as a white solid.

Melting point: 69.0°–75.2° C.

$^{1}$H-NMR(CDCl$_3$,TMS,ppm): δ1.30–2.10(12H,m), 2.40(4H,m), 4.68(1H,m) 6.75(1H,d,J$_{HF}$=7.0Hz), 7.20(1H,d, J$_{HF}$=9.0Hz).

IR(Kbr disk, cm$^{-1}$): 1200, 1385, 1430, 1505, 1725.

REFERENCE EXAMPLE 18

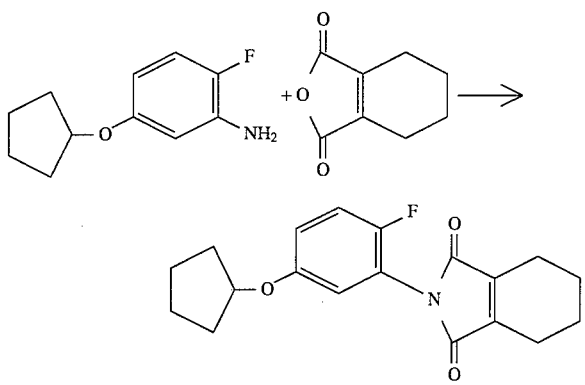

2-Fluoro-5-cyclopentyloxyaniline (330 mg, 1.69 mmol), 3,4,5,6-tetrahydrophthalic anhydride (258 mg, 1.70 mmol) and acetic acid (10 ml) as a solvent were placed in a round bottom flask (50 cc) followed by heating under refluxing for 5 hours. After completion of the reaction, the reaction solution was cooled to room temperature, water was added thereto, and the mixture was extracted with ethyl acetate (20 ml×3 portions). The organic layers were combined, and, after washing with water and a saturated aqueous sodium chloride solution, dried over anhydrous magnesium sulfate. After removing the drying agent, the solvent was distilled off under reduced pressure. The resulting dark red oily substance (345 mg) was isolated and purified by silica gel column chromatography (developing solvent: hexane/ethyl acetate=4/1) to obtain the derired N-(2-fluoro-5-cyclopentyloxyphenyl)-3,4,5,6-tetrahydrophthalimide as a light yellow oily substance (171 mg, 0.575 mmol, 34% yield).

$^{1}$H-NMR(CDCl$_3$,TMS,ppm): δ1.39–2.04(12H,m), 2.15(4H,m), 4.73(1H,m) 6.42–6.83(3H,m).

REFERENCE EXAMPLE 19

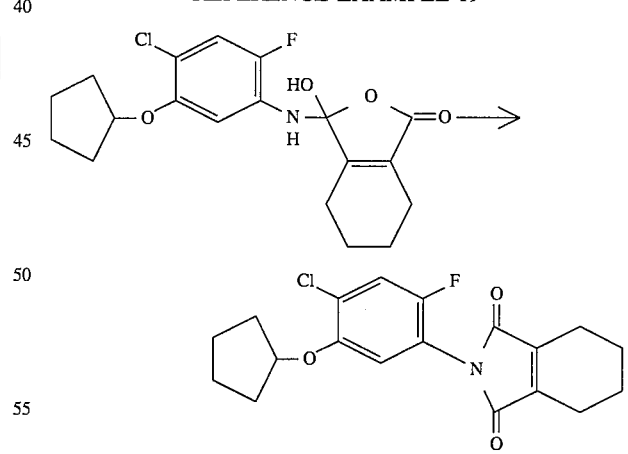

Acetic acid (50 ml) was added to an N-(2-fluoro-4-chloro-5-cyclopentyloxy)-3,4,5,6,-tetrahydroisophalimidohydroxy compound (19.1 g, 50.0 mmol), followed by stirring under heat-refluxing for 5 hours. After completion of the reaction, the reaction solution was poured into ice water, and the mixture was extracted with toluene (100 ml×2 portions). The organic layer was washed with water and dried over anhydrous magneisum sulfate. After removing the drying agent, a crude product obtained after distilling off the solvent under reduced pressure was recrystallized from methanol/hexane to obtain N-(2-fluoro-4-chloro-5-cyclopentyloxyphenyl)- 3,4,5,6-tetrahydrophthalimide (11.4 g, 62.3% yield). The spectral data, etc. are shown in Reference Example 17.

Examples of compounds of the present invention which can be prepared according to the processes described in Examples and Reference Examples illustrated above are shown in Tables 1 to 8.

TABLE 1

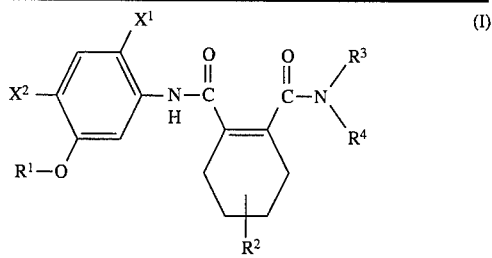

Tetrahydrophthalamide Derivatives represented by General Formula (I)

| No. | $X^1$ | $X^2$ | $R^1$ | $R^2$ | $R^3$ | $R^4$ |
|---|---|---|---|---|---|---|
| 1 | F | Cl | cyclopentyl | H | propyl | H |
| 2 | F | Cl | cyclopentyl | H | isopropyl | H |
| 3 | F | Cl | cyclopentyl | H | butyl | H |
| 4 | F | Cl | cyclopentyl | H | isobutyl | H |
| 5 | F | Cl | 3-methyl-cyclopentyl | H | isobutyl | H |
| 6 | F | Cl | cyclopentyl | H | neopentyl | H |
| 7 | F | Cl | cyclopentyl | H | hexyl | H |
| 8 | F | Cl | 3-methyl-cyclopentyl | H | hexyl | H |
| 9 | F | Cl | cyclopentyl | H | octyl | H |
| 10 | F | Cl | cyclopentyl | H | decyl | H |
| 11 | F | Cl | cyclopentyl | H | methyl | methyl |
| 12 | F | Cl | cyclopentyl | H | cyclohexyl | H |
| 13 | F | Cl | cyclopentyl | H | 2-methyl-cyclohexyl | H |
| 14 | F | Cl | cyclopentyl | H | exo-norbornyl | H |
| 15 | F | Cl | cyclopentyl | H | (−)-cis-myrtanyl | H |
| 16 | F | Cl | cyclopentyl | H | $-(CH_2)_4-$ | |
| 17 | F | Cl | cyclopentyl | H | $-(CH_2)_5-$ | |

TABLE 2

Tetrahydrophthalamide Derivatives represented by General Formula (I)

| No. | $X^1$ | $X^2$ | $R^1$ | $R^2$ | $R^3$ | $R^4$ |
|---|---|---|---|---|---|---|
| 18 | F | Cl | cyclopentyl | H | $-(CH_2)_6-$ | |
| 19 | F | Cl | cyclopentyl | H | $-CH_2CH_2OCH_2CH_2-$ | |
| 20 | F | Cl | cyclopentyl | H | benzyl | H |
| 21 | F | Cl | cyclopentyl | H | 2-chlorobenzyl | H |
| 22 | F | Cl | cyclopentyl | H | 4-methylbenzyl | H |
| 23 | F | Cl | cyclopentyl | H | 4-methoxybenzyl | H |
| 24 | F | Cl | cyclopentyl | H | R-(+)-1-phenylethyl | H |
| 25 | F | Cl | cyclopentyl | H | S-(−)-1-phenylethyl | H |
| 26 | F | Cl | cyclopentyl | H | (±)-1-phenylethyl | H |
| 27 | F | Cl | 3-methyl-cyclopentyl | H | R-(+)-1-phenylethyl | H |
| 28 | F | Cl | cyclohexyl | H | S-(+)-1-phenylethyl | H |
| 29 | F | Cl | cyclopentyl | H | R-(+)-(1-naphthyl)ethyl | H |
| 30 | F | Cl | cyclopentyl | H | S-(−)-1-(1-naphthyl)-ethyl | H |
| 31 | F | Cl | cyclopentyl | H | 2-(3,4-dimethoxyphenyl)-ethylhomoveratryl | H |
| 32 | F | Cl | cyclopentyl | H | 2-naphthylmethyl | H |

TABLE 2-continued

Tetrahydrophthalamide Derivatives represented by General Formula (I)

| No. | $X^1$ | $X^2$ | $R^1$ | $R^2$ | $R^3$ | $R^4$ |
|---|---|---|---|---|---|---|
| 33 | F | Cl | cyclopentyl | H | 2-pyridylmethyl | H |
| 34 | F | Cl | cyclopentyl | H | furfuryl | H |
| 35 | F | Cl | cyclopentyl | H | propargyl | H |
| 36 | F | Cl | cyclopentyl | H | H | H |
| 37 | F | Cl | cyclopentyl | H | methyl | H |

TABLE 3

Tetrahydrophthalamide Derivatives represented by General Formula (I)

| No. | $X^1$ | $X^2$ | $R^1$ | $R^2$ | $R^3$ | $R^4$ |
|---|---|---|---|---|---|---|
| 38 | F | Cl | cyclopentyl | H | ethyl | H |
| 39 | F | Cl | cyclopentyl | H | sec-butyl | H |
| 40 | F | Cl | cyclopentyl | H | 2-methoxyethyl | H |
| 41 | F | Cl | cyclopentyl | H | 2-aminocyclohexyl | H |
| 42 | F | Cl | cyclopentyl | H | 2-aminocyclohexyl | H |
| 43 | F | Cl | cyclopentyl | H | 1-ethoxycarbonyl-4-piperidyl | H |
| 44 | F | Cl | cyclopentyl | H | 2-phenylethyl | H |
| 45 | F | Cl | cyclopentyl | H | $-CH_2SCH_2CH_2-$ | |
| 46 | F | Cl | cyclopentyl | H | $-CH_2C(Me_2)CH_2CH_2CH_2-$ | |
| 47 | F | Cl | cyclopentyl | H | $-CH_2CH(Me)CH_2CH(Me)CH_2-$ | |
| 48 | F | Cl | 3-methyl-cyclopentyl | H | $-CH_2CH_2OCH_2CH_2-$ | |
| 49 | F | Cl | cyclopentyl | H | $-CH_2CH_2N(Me)CH_2CH_2-$ | |
| 50 | F | Cl | cyclopentyl | H | $-CH_2CH(Me)NHCH(Me)CH_2-$ | |
| 51 | F | Cl | cyclopentyl | H | ethyl | propyl |
| 52 | F | Cl | cyclopentyl | H | 2-bromoethyl | H |
| 53 | F | Cl | cyclopentyl | H | 2-hydroxyethyl | H |
| 54 | F | Cl | cyclopentyl | H | 2-hydroxyethyl | ethyl |
| 55 | F | Cl | cyclopentyl | H | 2-chloroethyl | 2-chloroethyl |
| 56 | F | Cl | cyclopentyl | H | 1-methoxycarbonyl-2-methylpropyl | H |

TABLE 4

Tetrahydrophthalamide Derivatives represented by General Formula (I)

| No. | $X^1$ | $X^2$ | $R^1$ | $R^2$ | $R^3$ | $R^4$ |
|---|---|---|---|---|---|---|
| 57 | F | Cl | cyclopentyl | H | benzyl | methyl |
| 58 | F | Cl | cyclopentyl | H | cumyl | H |
| 59 | F | Cl | cyclopentyl | H | 4-methylcumyl | H |
| 60 | F | Cl | cyclopentyl | H | 4-fluorocumyl | H |
| 61 | F | Cl | cyclopentyl | H | 3-fluorocumyl | H |
| 62 | F | Cl | cyclopentyl | H | 4-chlorocumyl | H |
| 63 | F | Cl | cyclopentyl | H | 3-chlorocumyl | H |
| 64 | F | Cl | cyclopentyl | H | 4-bromocumyl | H |
| 65 | F | Cl | cyclopentyl | H | 3-trifluoromethylcumyl | H |
| 66 | F | Cl | cyclopentyl | H | 1-phenyl-1-methylpropyl | H |
| 67 | F | Cl | cyclopentyl | H | 1-(4-chlorophenyl)-1- | H |

TABLE 4-continued

Tetrahydrophthalamide Derivatives represented by General Formula (I)

| No. | $X^1$ | $X^2$ | $R^1$ | $R^2$ | $R^3$ | $R^4$ |
|---|---|---|---|---|---|---|
| 68 | F | Cl | cyclopentyl | H | allyl methylpropyl | allyl |
| 69 | F | Cl | cyclopentyl | H | 4-fluorophenyl | H |
| 70 | F | Cl | cyclopentyl | H | 4-chlorophenyl | H |
| 71 | F | Cl | cyclopentyl | H | 4-methylphenyl | H |
| 72 | F | Cl | cyclopentyl | H | 4-tert-butylphenyl | H |
| 73 | F | Cl | cyclopentyl | H | 4-(4-fluorophenyl)- | H |

TABLE 5

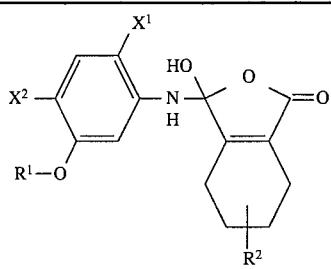

(V')

Tetrahydroisophthalimidohydroxy Derivatives represented by General Formula (V')

| No. | $X^1$ | $X^2$ | $R^1$ | $R^2$ |
|---|---|---|---|---|
| 74 | F | H | cyclopentyl | H |
| 75 | F | H | cyclopentyl | H |
| 76 | F | H | 2-methylcyclopentyl | H |
| 77 | F | H | 3-methylcyclopentyl | H |
| 78 | F | H | cyclohexyl | H |
| 79 | F | H | 2-methylcyclohexyl | H |
| 80 | F | H | cycloheptyl | H |
| 81 | F | H | cyclooctyl | H |
| 82 | F | F | cyclopropyl | H |
| 83 | F | F | cyclopentyl | H |
| 84 | F | F | 2-methylcyclopentyl | H |
| 85 | F | F | 3-methylcyclopentyl | H |
| 86 | F | F | cyclohexyl | H |
| 87 | F | F | 2-methylcyclohexyl | H |
| 88 | F | F | cycloheptyl | H |
| 89 | F | F | cyclooctyl | H |
| 90 | F | Cl | cyclopropyl | H |
| 91 | F | Cl | cyclopentyl | H |

TABLE 6

Tetrahydroisophthalimidohydroxy Derivatives represented by General Formula (V')

| No. | $X^1$ | $X^2$ | $R^1$ | $R^2$ |
|---|---|---|---|---|
| 92 | F | Cl | 2-methylcyclopentyl | H |
| 93 | F | Cl | 3-methylcyclopentyl | H |
| 94 | F | Cl | cyclohexyl | H |
| 95 | F | Cl | 2-methylcyclohexyl | H |
| 96 | F | Cl | cycloheptyl | H |
| 97 | F | Cl | cyclooctyl | H |
| 98 | F | Br | cyclopropyl | H |
| 99 | F | Br | cyclopentyl | H |
| 100 | F | Br | 2-methylcyclopentyl | H |
| 101 | F | Br | 3-methylcyclopentyl | H |
| 102 | F | Br | cyclohexyl | H |
| 103 | F | Br | 2-methylcyclohexyl | H |
| 104 | F | Br | cycloheptyl | H |
| 105 | F | Br | cyclooctyl | H |
| 106 | Cl | Cl | cyclopropyl | H |
| 107 | Cl | Cl | 2-methylcyclopentyl | H |
| 108 | Cl | Cl | 3-methylcyclopentyl | H |

TABLE 6-continued

Tetrahydroisophthalimidohydroxy Derivatives represented by General Formula (V')

| No. | $X^1$ | $X^2$ | $R^1$ | $R^2$ |
|---|---|---|---|---|
| 109 | Cl | Cl | cyclohexyl | H |
| 110 | Cl | Br | cyclopentyl | H |
| 111 | Cl | Br | 3-methylcyclopentyl | H |

TABLE 7

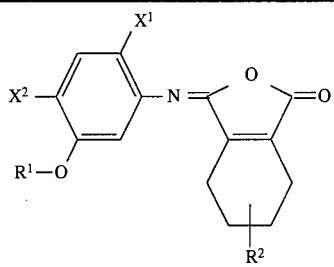

(V")

Tetrahydroisophthalimide Derivatives represented by General Formula (V")

| No. | $X^1$ | $X^2$ | $R^1$ | $R^2$ |
|---|---|---|---|---|
| 112 | F | H | cyclopropyl | H |
| 113 | F | H | cyclopentyl | H |
| 114 | F | H | 2-methylcyclopentyl | H |
| 115 | F | H | 3-methylcyclopentyl | H |
| 116 | F | H | cyclohexyl | H |
| 117 | F | H | 2-methylcyclohexyl | H |
| 118 | F | H | cycloheptyl | H |
| 119 | F | H | cyclooctyl | H |
| 120 | F | F | cyclopropyl | H |
| 121 | F | F | cyclopentyl | H |
| 122 | F | F | 2-methylcyclopentyl | H |
| 123 | F | F | 3-methylcyclopentyl | H |
| 124 | F | F | cyclohexyl | H |
| 125 | F | F | 2-methylcyclohexyl | H |
| 126 | F | F | cycloheptyl | H |
| 127 | F | F | cyclooctyl | H |
| 128 | F | Cl | cyclopropyl | H |
| 129 | F | Cl | cyclopentyl | H |
| 130 | F | Cl | 2-methylcyclopentyl | H |

TABLE 8

Tetrahydroisophthalimide Derivatives represented by General Formula (V")

| No. | $X^1$ | $X^2$ | $R^1$ | $R^2$ |
|---|---|---|---|---|
| 131 | F | Cl | 3-methylcyclopentyl | H |
| 132 | F | Cl | cyclohexyl | H |
| 133 | F | Cl | 2-methylcyclohexyl | H |
| 134 | F | Cl | cycloheptyl | H |
| 135 | F | Cl | cyclooctyl | H |
| 136 | F | Br | cyclopropyl | H |
| 137 | F | Br | cyclopentyl | H |
| 138 | F | Br | 2-methylcyclopentyl | H |
| 139 | F | Br | 3-methylcyclopentyl | H |
| 140 | F | Br | cyclohexyl | H |
| 141 | F | Br | 2-methylcyclohexyl | H |
| 142 | F | Br | cycloheptyl | H |
| 143 | F | Br | cyclooctyl | H |
| 144 | Cl | Cl | cyclopentyl | H |
| 145 | Cl | Cl | 2-methylcyclopentyl | H |
| 146 | Cl | Cl | 3-methylcyclopentyl | H |
| 147 | Cl | Cl | cyclohexyl | H |
| 148 | Cl | Br | cyclopentyl | H |
| 149 | Cl | Br | 3-methylcyclopentyl | H |

The thus-obtained compounds of the present invention have excellent performance as a herbicide as described above.

In using the compounds of the present invention as a herbicide, the compounds per se can be used, but generally they can be used as a herbicide by mixing with one or more auxiliary agents. Generally, it is preferable to use them by incorporating various carriers, fillers, solvent, surface active agents, stabilizers, etc. as auxiliary agents, and formulating into preparations in the form of a wettable powder, an emulsion, a powder, a granule, and a flowable agent by a usual method.

As the solvent which is one of the auxiliary agents in the herbicide containing the compound of the present invention as an active ingredient, water, alcohols, ketones, ethers, aliphatic and aromatic hydrocarbons, halogenated hydrocarbons, acidamides, esters and nitriles are suitable, and one of these solvents or a mixture of two or more solvents can be used.

As the filler, mineral powders, for example, clays such as kaolin, bentonite, etc., talcs such as talc, pyrophylite, etc., and oxides such as diatomaceous earth, white carbon, etc., and vegetable powders such as soybean powder, CMC, etc. can be used. Also, a surface active agent may be used as a spreading agent, a dispersing agent, an emulsifying agent and a penetrating agent. Examples of the surface active agents inclcude nonionic surface active agents, cationic surface active agents and amphoteric surface active agents. One of these surface active agents or a mixture of two or more thereof can be used depending upon the utility thereof.

Preferred methods for using the herbicide containing the compound of the present invention as an active ingredient include a soil treatment, a water surface treatment, and stem-foliar treatment, and a particularly excellent effect can be achieved by application prior to germination to a germ stage.

Further, the herbicide containing the compound of the present invention as an active ingredient can be used in admixture with or together with other active ingredients which do not adversely affect the herbicidal activity of the present active ingredient, for example, other herbicidal agents, insecticidal agents, antimicrobial agents, plant growth controlling agents, etc.

Hereinafter, the present invention is further illustrated by the preparation examples of the herbicidal agents containing the compound of the present invention as an active ingredient, and the test examples studying herbicidal effects by the present herbicide. In these examples, part is part by weight.

PREPARATION EXAMPLE 1

Emulsion

20 Parts of the compound of the present invention, 35 parts of xylene, 40 parts of cyclohexanone and 5 parts of Sorbol 9000A (produced by Toho Chemical Industry Co., Ltd.) were uniformly mixed to prepare an emulsion. For other compounds of the present invention, emulsions were obtained by the same procedure as described above.

PREPARATION EXAMPLE 2

Wettable Powder

A mixture of 50 parts of the compound of the present invention, 25 parts of diatomaceous earth, 22 parts of clay and 3 parts of Lunox R100C (produced by Toho Chemical Industy Co., Ltd.) was mixed and ground to prepare a wettable powder.

PREPARATION EXAMPLE 3

Granules

A mixture of 5 parts of the compound of the present invention, 35 parts of bentonite, 55 parts of talc and 5 parts of sodium ligninsulfonate was uniformly mixed and ground, thereafter water was added thereto, followed by kneading. The mixture was granulated by an extrusion granulator, dried, and sieved to obtain granules. For other compounds of the present invention, granules were obtained by the same procedure as described above.

The herbicidal effects of the compounds of the present invention represented by the general formula (I) were investigated according to the methods shown in the following Test Examples using the preparations prepared in accordance with the procedure illustrated as above. The herbicidal effects on the test plants and the detrimental effects by the agent on the test crops were determined according to the criterions shown below (Table 9).

TABLE 9

| Rating Criterions | |
|---|---|
| Percent Inhibition of Growth | |
| 1 | 0% |
| 2 | 25% |
| 3 | 50% |
| 4 | 75% |
| 5 | 100% |

As control compounds, a commercially available compound (A) was used with respect to the effects by the soil pretreatment in the paddy field, and a commercially available compound (B) was used with respect to the effects by the soil treatment in the field and the effects by the stem-foliar treatment. By using the same preparation procedure and treating method, the herbicidal activity and the detrimental effect by the agent on the crops thereof were investigated on the same rating criterions as above, and the results obtained are shown in Tables.

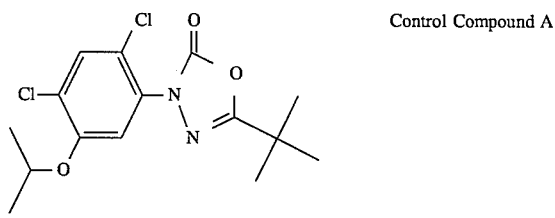

Control Compound A

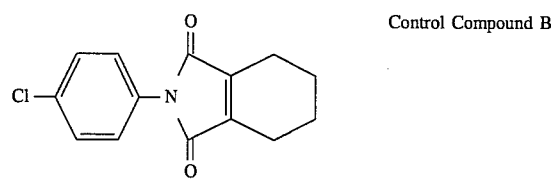

Control Compound B

TEST EXAMPLE 1

Effects on Paddy Field Weeds

Soil of a paddy field was filled in a pot of 1/10000 are, and seeds of *Echinochloa oryzicola, Cyperus difformis, Monochoria vaginalis, Scirpus juncoides, Eleocharis acicularis* and other annual broad leaf weeds, and rice seedlings at a 2.5-leaf stage (Species: Koshihikari) were seeded or transplanted, and the pot was maintained in the submerged condition. After one day, the wettable powder or the emulsion of the compound of the present invention prepared according to the preparation example was diluted, and the pot was treated dropwise at a predetermined dose per are. On the 15th day after the treatment, the herbicidal effect on the test plants and the detrimental effect by the agent on the rice plant were investigated on the rating criterions in 1 to 5 ranks, and the results shown in Tables 10 to 23 were obtained.

TABLE 10

Effects by Soil Pretreatment in Paddy Field Soil

| Compound No. | Amount Applied (g/a) | Herbicidal Effects | | | | | | (1) |
|---|---|---|---|---|---|---|---|---|
| | | (2) | (3) | (4) | (5) | (6) | (7) | (8) |
| 1 | 2.5 | 5 | 5 | 5 | 5 | 4.5 | | 1.2 |
| | 1.0 | 4.7 | 4.5 | 5 | 5 | 3.8 | | 1 |
| | 0.5 | 4.5 | 4 | 5 | 5 | 2.5 | | 1 |
| | 0.25 | 3.5 | 3 | 5 | 5 | 2 | | 1 |
| 2 | 0.5 | 5 | 5 | 5 | 5 | 5 | | 1.5 |
| | 0.25 | 5 | 5 | 5 | 5 | 4.9 | | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 11

Effects by Soil Pretreatment in Paddy Field Soil

| Compound No. | Amount Applied (g/a) | Herbicidal Effects | | | | | | (1) |
|---|---|---|---|---|---|---|---|---|
| | | (2) | (3) | (4) | (5) | (6) | (7) | (8) |
| 3 | 0.5 | 5 | 5 | 5 | 5 | 5 | | 2 |
| | 0.25 | 5 | 5 | 5 | 5 | 4.9 | | 1 |
| 4 | 1.0 | 5 | 5 | 5 | 5 | 5 | | 1.5 |
| | 0.5 | 5 | 5 | 5 | 5 | 4.8 | | 1.3 |
| | 0.25 | 5 | 5 | 5 | 5 | 4.7 | | 1.2 |
| 5 | 5.0 | 4 | 5 | 5 | 5 | 2.5 | | 1 |
| | 2.5 | 3 | 4.8 | 4.8 | 5 | 1.5 | | 1 |
| 6 | 1.0 | 5 | 5 | 5 | 5 | 5 | | 1.1 |
| | 0.5 | 4.9 | 5 | 5 | 5 | 4.8 | | 1 |
| | 0.25 | 4.8 | 5 | 4.9 | 4.9 | 4.5 | | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 12

Effects by Soil Pretreatment in Paddy Field Soil

| Compound No. | Amount Applied (g/a) | Herbicidal Effects | | | | | | (1) |
|---|---|---|---|---|---|---|---|---|
| | | (2) | (3) | (4) | (5) | (6) | (7) | (8) |
| 7 | 1.0 | 5 | 5 | 5 | 5 | 5 | | |
| | 0.5 | 5 | 5 | 5 | 5 | 4.9 | 4.9 | 1.2 |

TABLE 12-continued

Effects by Soil Pretreatment in Paddy Field Soil

| Compound No. | Amount Applied (g/a) | Herbicidal Effects | | | | | | (1) |
|---|---|---|---|---|---|---|---|---|
| | | (2) | (3) | (4) | (5) | (6) | (7) | (8) |
| | 0.25 | 4.9 | 5 | 5 | 5 | 4.9 | 4 | 1 |
| 8 | 1.0 | 5 | 5 | 5 | 5 | 3 | 1.5 | |
| | 0.5 | 5 | 5 | 5 | 5 | 4.5 | 3 | 1.2 |
| | 0.25 | 4.9 | 5 | 4.9 | 4.8 | 4 | 2 | 1 |
| 9 | 1.0 | 5 | 5 | 5 | 5 | 5 | 4.9 | 1.5 |
| | 0.5 | 5 | 5 | 5 | 5 | 5 | 4 | 1.2 |
| | 0.25 | 5 | 5 | 5 | 5 | 4.8 | 4 | 1.1 |
| 11 | 0.5 | 5 | 5 | 5 | 5 | 5 | 5 | |
| | 0.25 | 5 | 5 | 5 | 5 | 5 | 5 | 1.5 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 13

Effects by Soil Pretreatment in Paddy Field Soil

| Compound No. | Amount Applied (g/a) | Herbicidal Effects | | | | | | (1) |
|---|---|---|---|---|---|---|---|---|
| | | (2) | (3) | (4) | (5) | (6) | (7) | (8) |
| 12 | 0.5 | 5 | 5 | 5 | 5 | 4.9 | | 1.2 |
| | 0.25 | 5 | 5 | 5 | 5 | 4.8 | | 1 |
| 13 | 1.0 | 5 | 5 | 5 | 5 | 4.9 | | |
| | 0.5 | 5 | 5 | 5 | 5 | 4.8 | | 1.2 |
| | 0.25 | 4 | 4.8 | 4.9 | 4.8 | 4 | | 1 |
| 14 | 1.0 | 5 | 5 | 5 | 5 | 5 | 5 | 1.3 |
| | 0.5 | 5 | 5 | 5 | 5 | 4.9 | 4.8 | 1.3 |
| | 0.25 | 4.9 | 5 | 5 | 5 | 4.8 | 4.8 | 1.1 |
| 15 | 1.0 | 5 | 5 | 5 | 5 | 4.9 | 4.9 | 1.1 |
| | 0.5 | 5 | 5 | 5 | 5 | 4.8 | 4.5 | 1 |
| | 0.25 | 4.9 | 5 | 5 | 5 | 4 | 4 | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 14

Effects by Soil Pretreatment in Paddy Field Soil

| Compound No. | Amount Applied (g/a) | Herbicidal Effects | | | | | | (1) |
|---|---|---|---|---|---|---|---|---|
| | | (2) | (3) | (4) | (5) | (6) | (7) | (8) |
| 16 | 0.5 | 5 | 5 | 5 | 5 | 5 | 5 | 1.2 |
| | 0.25 | 5 | 5 | 5 | 5 | 5 | 4.5 | 1 |
| 17 | 0.5 | 5 | 5 | 5 | 5 | 5 | 5 | 1.5 |
| | 0.25 | 5 | 5 | 5 | 5 | 5 | 5 | 1.5 |
| 18 | 0.5 | 5 | 5 | 5 | 5 | 4.9 | | 1.2 |
| | 0.25 | 5 | 5 | 5 | 5 | 4.5 | | 1.1 |
| 19 | 0.25 | 5 | 5 | 5 | 5 | 5 | 4.8 | 1.2 |
| | 0.1 | 5 | 5 | 5 | 5 | 4.5 | 3 | 1.1 |
| 20 | 1.0 | 5 | 5 | 5 | 5 | 5 | | 1.2 |
| | 0.5 | 5 | 5 | 5 | 5 | 4.9 | | 1.2 |
| | 0.25 | 5 | 5 | 5 | 5 | 4.8 | | 1 |

(1) Detrimental Effects by Agent

TABLE 14-continued

Effects by Soil Pretreatment in Paddy Field Soil

| Compound No. | Amount Applied (g/a) | Herbicidal Effects (2) | (3) | (4) | (5) | (6) | (7) | (1) (8) |
|---|---|---|---|---|---|---|---|---|

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 15

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 21 | 1.0 | 5 | 5 | 5 | 5 | 5 | | 1.1 |
|  | 0.5 | 5 | 5 | 5 | 5 | 4.9 | | 1.1 |
|  | 0.25 | 5 | 5 | 5 | 5 | 4.8 | | 1 |
| 22 | 1.0 | 5 | 5 | 5 | 5 | 4.9 | | 1 |
|  | 0.5 | 5 | 5 | 5 | 5 | 4.8 | | 1 |
|  | 0.25 | 5 | 5 | 5 | 5 | 4.8 | | 1 |
| 24 | 1.0 | 5 | 5 | 5 | 5 | 5 | 4.5 | 1.2 |
|  | 0.5 | 5 | 5 | 5 | 5 | 4.9 | 4.5 | 1 |
|  | 0.25 | 5 | 5 | 5 | 5 | 4.9 | 4 | 1 |
| 25 | 1.0 | 5 | 5 | 5 | 5 | 3.6 | 4 | 1.2 |
|  | 0.5 | 4.9 | 5 | 5 | 5 | 3.5 | 3.5 | 1.1 |
|  | 0.25 | 4.8 | 5 | 5 | 5 | 3.5 | 3 | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 16

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 26 | 1.0 | 4.8 | 5 | 5 | 5 | 4.9 | 3 | 1 |
|  | 0.5 | 4.5 | 5 | 5 | 5 | 4.8 | 3 | 1 |
|  | 0.25 | 5 | 4 | 4.8 | 4.9 | 4 | 2 | 1 |
| 27 | 1.0 | 4 | 5 | 4.9 | 5 | 3 | 2 | 1 |
| 28 | 1.0 | 5 | 5 | 5 | 5 | 4.9 | 4.8 | 1 |
|  | 0.5 | 5 | 5 | 5 | 5 | 4.8 | 4 | 1 |
|  | 0.25 | 4.9 | 4.9 | 5 | 4.9 | 4.5 | 4 | 1 |
| 31 | 1.0 | 5 | 5 | 5 | 5 | 4.5 | 4.5 | 1.1 |
|  | 0.5 | 4.5 | 4.8 | 4.8 | 5 | 3 | 3 | 1 |
|  | 0.25 | 3 | 4 | 4 | 4 | 2 | 2 | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 17

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 33 | 2.5 | 5 | 5 | 5 | 5 | 4.8 | 4.9 | 1.1 |
|  | 1.0 | 4.9 | 5 | 5 | 5 | 4 | 4 | 1 |
|  | 0.5 | 4 | 4.5 | 4.8 | 4.8 | 3 | 3 | 1 |
| 35 | 1.0 | 5 | 5 | 5 | 5 | 4 | | 1 |
|  | 0.5 | 3.5 | 5 | 5 | 5 | 3 | | 1 |
|  | 0.25 | 2 | 4 | 4 | 4 | 1 | | 1 |
| 36 | 0.5 | 5 | 5 | 5 | 5 | 4.9 | 5 | |
|  | 0.25 | 5 | 5 | 5 | 5 | 4.8 | 4.9 | 1.5 |
| 37 | 1.0 | 5 | 5 | 5 | 5 | 4.9 | 5 | 1.5 |
|  | 0.5 | 5 | 5 | 5 | 5 | 4.9 | 5 | 1.3 |
|  | 0.25 | 5 | 5 | 5 | 5 | 4.7 | 4.8 | 1.1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 18

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 38 | 0.5 | 5 | 5 | 5 | 5 | 5 | 4.7 | |
|  | 0.25 | 5 | 5 | 5 | 5 | 4.9 | 4.5 | 1.5 |
| 39 | 1.0 | 5 | 5 | 5 | 5 | 5 | 2 | 1.2 |
|  | 0.5 | 5 | 5 | 5 | 5 | 4.8 | 2 | 1 |
|  | 0.25 | 5 | 4.9 | 5 | 5 | 4 | 1.5 | 1 |
| 40 | 1.0 | 4.9 | 4.9 | 5 | 5 | 4.5 | 4 | 1.2 |
|  | 0.5 | 4.9 | 4.8 | 5 | 5 | 3.5 | 3 | 1.2 |
| 41 | 1.0 | 2 | 4.5 | 4.9 | 5 | 3 | 1.5 | 1 |
| 43 | 2.5 | 5 | 5 | 5 | 5 | 2 | 2 | 1.1 |
|  | 1.0 | 4 | 5 | 5 | 5 | 1.5 | 1.5 | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 19

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 44 | 1.0 | 5 | 5 | 5 | 5 | 4.9 | 5 | 1.2 |
|  | 0.5 | 5 | 5 | 5 | 5 | 4.7 | 4.9 | 1.1 |
|  | 0.25 | 5 | 5 | 5 | 5 | 4.5 | 4.8 | 1.1 |
| 45 | 0.5 | 5 | 5 | 5 | 5 | 4.9 | 5 | 1.5 |
|  | 0.25 | 5 | 5 | 5 | 5 | 4.9 | 4.9 | 1.3 |
| 46 | 0.5 | 5 | 5 | 5 | 5 | 4.8 | 5 | 1.6 |
|  | 0.25 | 5 | 5 | 5 | 5 | 4.8 | 4.9 | 1.3 |
| 47 | 0.5 | 5 | 5 | 5 | 5 | 5 | 5 | 1.5 |
|  | 0.25 | 5 | 5 | 5 | 5 | 5 | 5 | 1.3 |

(1) Detrimental Effects by Agent
(2) *Echinochloa oryzicola*

TABLE 19-continued

Effects by Soil Pretreatment in Paddy Field Soil

| Compound No. | Amount Applied (g/a) | Herbicidal Effects (2) | (3) | (4) | (5) | (6) | (7) | (1) (8) |
|---|---|---|---|---|---|---|---|---|

(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 20

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 48 | 1.0 | 5 | 5 | 5 | 5 | 4.9 | 4.9 | |
|    | 0.5 | 5 | 5 | 5 | 5 | 4.8 | 4.8 | 1.5 |
|    | 0.25 | 5 | 5 | 5 | 5 | 4.7 | 4.5 | 1.2 |
| 49 | 0.5 | 5 | 5 | 5 | 5 | 5 | 5 | 1.6 |
|    | 0.25 | 5 | 5 | 5 | 5 | 4.9 | 5 | 1.4 |
| 50 | 0.5 | 5 | 5 | 5 | 5 | 5 | 5 | |
|    | 0.25 | 5 | 5 | 5 | 5 | 4.9 | 4.9 | 1.5 |
| 51 | 0.5 | 5 | 5 | 5 | 5 | 4.9 | 4.8 | 1.2 |
|    | 0.25 | 5 | 5 | 5 | 5 | 4.5 | 4.7 | 1.1 |
| 52 | 0.5 | 5 | 5 | 5 | 5 | 5 | 5 | 1.5 |
|    | 0.25 | 5 | 5 | 5 | 5 | 5 | 5 | 1.3 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 21

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 54 | 0.5 | 5 | 5 | 5 | 5 | 5 | 5 | 1.4 |
|    | 0.25 | 5 | 5 | 5 | 5 | 4.9 | 4.9 | 1.3 |
| 55 | 1.0 | 5 | 5 | 5 | 5 | 5 | 5 | 1.2 |
|    | 0.5 | 5 | 5 | 5 | 5 | 4.8 | 4.5 | 1.1 |
|    | 0.25 | 4.5 | 5 | 5 | 5 | 4.7 | 4.2 | 1 |
| 57 | 1.0 | 5 | 5 | 5 | 5 | 5 | 5 | |
|    | 0.5 | 5 | 5 | 5 | 5 | 5 | 5 | 1.5 |
|    | 0.25 | 5 | 5 | 5 | 5 | 5 | 4.9 | 1.3 |
| 58 | 2.0 | 4 | 5 | 5 | 5 | 3.5 | 4.8 | 1.3 |
|    | 1.0 | 3.8 | 4.9 | 4.9 | 5 | 3 | 3 | 1.1 |
| 61 | 2.0 | 2.5 | 3 | 3.5 | 5 | 2 | 2 | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 22

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 65 | 2.0 | 3 | 4.9 | 5 | 5 | 3 | 3 | 1 |
|    | 1.0 | 2 | 4.8 | 4.9 | 5 | 2 | 2 | 1 |
| 67 | 1.0 | 5 | 5 | 5 | 5 | 4.9 | 4 | 1.5 |
|    | 0.5 | 4.9 | 5 | 5 | 5 | 4.5 | 3.5 | 1.1 |
|    | 0.25 | 3.5 | 5 | 5 | 5 | 4 | 3 | 1 |
| 68 | 0.5 | 5 | 5 | 5 | 5 | 5 | 5 | 1.4 |
|    | 0.25 | 5 | 5 | 5 | 5 | 4.9 | 4.9 | 1.2 |
| 69 | 1.0 | 5 | 5 | 5 | 5 | 4.9 | 4.9 | 1.2 |
|    | 0.5 | 4.9 | 5 | 5 | 5 | 4 | 4.8 | 1.2 |
|    | 0.25 | 4.9 | 5 | 5 | 4.9 | 4 | 4 | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TABLE 23

Effects by Soil Pretreatment in Paddy Field Soil

| Compound No. | Amount Applied (g/a) | (2) | (3) | (4) | (5) | (6) | (7) | (1) (8) |
|---|---|---|---|---|---|---|---|---|
| 70 | 2.0 | 3 | 5 | 5 | 5 | 3.5 | 3.5 | 1.5 |
|    | 1.0 | 2 | 5 | 5 | 5 | 2 | 3 | 1.2 |
| 72 | 1.0 | 4.9 | 5 | 5 | 5 | 4.8 | 4.8 | 1.2 |
|    | 0.5 | 4.8 | 5 | 4.9 | 5 | 4.5 | 4.5 | 1.1 |
|    | 0.25 | 4 | 4.9 | 4.9 | 4.8 | 3.5 | 4 | 1 |
| 73 | 0.5 | 5 | 5 | 5 | 5 | 4.8 | 5 | 1.5 |
|    | 0.25 | 5 | 5 | 5 | 5 | 4.8 | 5 | 1.3 |
| A  | 1.0 | 5 | 5 | 5 | 5 | 4.8 | 4.8 | 1.3 |
|    | 0.5 | 4.8 | 5 | 5 | 5 | 4.5 | 4.8 | 1.1 |
|    | 0.25 | 4 | 5 | 4.9 | 5 | 4 | 4.5 | 1 |

(1) Detrimental Effects by Agent
(2) *Echinochloa oryzicola*
(3) *Cyperus difformis*
(4) Other Annual Broad Leaf Weeds
(5) *Monochoria veginalis*
(6) *Scirpus juncoides*
(7) *Eleocharis acicularis*
(8) Rice plant, 2.5-Leaf Stage

TEST EXAMPLE 2

Effects by Field Soil Treatment

Field soil was filled in a vat having an area of 10×10 cm$^2$ and a depth of 5 cm, and seeds of *Echinochloa crus-galli, Digitalia ciliaris, Amaranthus viridis, Chenopodium album* and corn were seeded, and a covering soil of 0.5 cm was put on the seeds. Next day, the wettable powder or the emulsion of the compound of the present invention prepared according to the preparation example was diluted and applied over the covering soil at a predetermined dose per are. On the 15th day after treatment, the herbicidal effects on the test weeds and the detrimental effects by the agent on the corn were investigated in the same manner as in Test Example 1.

The results obtained are shown in Tables 24 to 30.

TABLE 24

Effects by Soil Treatment in Field

| Compound No. | Amount Applied (g/a) | Herbicidal Effects (2) | (3) | (4) | (5) | (1) (6) |
|---|---|---|---|---|---|---|
| 1 | 20.0 | 3.8 | 4 | 5 | 5 | 1.2 |
|  | 10.0 | 3 | 3.8 | 5 | 5 | 1 |
| 2 | 20.0 | 3 | 3.8 | 5 | 4.5 | 1.2 |
|  | 10.0 | 2 | 2.5 | 4.8 | 3 | 1 |

(1) Detrimental Effects by Agent
(2) *Echinochloa crus-galli*
(3) *Digitalia ciliaris*
(4) *Amaranthus viridis*
(5) *Chenopodium album*
(6) Corn

TABLE 25

Effects by Soil Treatment in Field

| Compound No. | Amount Applied (g/a) | Herbicidal Effects (2) | (3) | (4) | (5) | (1) (6) |
|---|---|---|---|---|---|---|
| 3 | 20.0 | 3 | 4.7 | 5 | 5 | 1 |
|  | 10.0 | 3 | 4.3 | 5 | 5 | 1 |
|  | 5.0 | 3 | 4.3 | 5 | 5 | 1 |
| 4 | 10.0 | 3 | 4 | 5 | 5 | 1.5 |
|  | 5.0 | 2.8 | 2 | 5 | 4.5 | 1 |
| 11 | 20.0 | 3 | 5 | 5 | 5 |  |
|  | 10.0 | 2.5 | 4.9 | 5 | 5 | 1.3 |
|  | 5.0 | 2 | 4.8 | 4.9 | 4.9 | 1 |
| 14 | 10.0 | 3 | 4.8 | 5 | 5 | 1.7 |
| 16 | 10.0 | 3.8 | 4.7 | 5 | 5 |  |
|  | 5.0 | 3 | 4.5 | 4.5 | 4.9 | 1.5 |

(1) Detrimental Effects by Agent
(2) *Echinochloa crus-galli*
(3) *Digitalia ciliaris*
(4) *Amaranthus viridis*
(5) *Chenopodium album*
(6) Corn

TABLE 26

Effects by Soil Treatment in Field

| Compound No. | Amount Applied (g/a) | Herbicidal Effects (2) | (3) | (4) | (5) | (1) (6) |
|---|---|---|---|---|---|---|
| 17 | 10.0 | 3 | 4 | 5 | 5 | 1.5 |
|  | 5.0 | 2.5 | 3 | 5 | 4.8 | 1.5 |
| 18 | 10.0 | 2.5 | 3.5 | 5 | 4.9 | 1.7 |
| 19 | 20.0 | 4.9 | 5 | 5 | 5 |  |
|  | 10.0 | 4.3 | 4.9 | 5 | 5 | 1.1 |
|  | 5.0 | 3.8 | 4.2 | 5 | 5 | 1 |
| 21 | 20.0 | 3 | 4 | 5 | 4.8 | 1.1 |
| 24 | 20.0 | 3 | 3.5 | 4.5 | 5 |  |
|  | 10.0 | 2 | 2 | 4 | 5 | 1.7 |
| 25 | 10.0 | 2.5 | 4.2 | 5 | 5 | 1.5 |

(1) Detrimental Effects by Agent
(2) *Echinochloa crus-galli*
(3) *Digitalia ciliaris*
(4) *Amaranthus viridis*
(5) *Chenopodium album*
(6) Corn

TABLE 27

Effects by Soil Treatment in Field

| Compound No. | Amount Applied (g/a) | Herbicidal Effects (2) | (3) | (4) | (5) | (1) (6) |
|---|---|---|---|---|---|---|
| 28 | 10.0 | 2 | 3.5 | 4 | 5 | 1.5 |
| 36 | 10.0 | 4.7 | 5 | 5 | 5 | 1.7 |
|  | 5.0 | 4.5 | 4.8 | 5 | 5 | 1.1 |
| 37 | 10.0 | 4.5 | 4.6 | 5 | 5 |  |
|  | 5.0 | 4.3 | 4.5 | 5 | 5 | 1.2 |
| 38 | 10.0 | 4.5 | 4.5 | 5 | 5 | 1.2 |
|  | 5.0 | 3.5 | 4 | 5 | 5 | 1 |
| 39 | 10.0 | 2 | 3.8 | 5 | 5 | 1.2 |
| 40 | 20.0 | 4.6 | 4.9 | 5 | 5 | 1.1 |
|  | 10.0 | 4 | 4 | 5 | 4.9 | 1 |

(1) Detrimental Effects by Agent
(2) *Echinochloa crus-galli*
(3) *Digitalia ciliaris*
(4) *Amaranthus viridis*
(5) *Chenopodium album*
(6) Corn

TABLE 28

Effects by Soil Treatment in Field

| Compound No. | Amount Applied (g/a) | Herbicidal Effects (2) | (3) | (4) | (5) | (1) (6) |
|---|---|---|---|---|---|---|
| 44 | 20.0 | 4.5 | 4.5 | 5 | 5 | 1 |
|  | 10.0 | 3.2 | 4.5 | 5 | 5 | 1 |
|  | 5.0 | 2 | 3 | 4.8 | 4.9 | 1 |
| 45 | 10.0 | 4.5 | 4.5 | 5 | 5 | 1.2 |
|  | 5.0 | 3.5 | 4.5 | 5 | 5 | 1 |
| 46 | 10.0 | 4.5 | 4.5 | 5 | 5 | 1.1 |
|  | 5.0 | 3.5 | 4.2 | 5 | 5 | 1 |
| 47 | 10.0 | 4.7 | 4.5 | 5 | 5 | 1 |
|  | 5.0 | 4.2 | 3.5 | 4.9 | 5 | 1 |
| 48 | 10.0 | 4.8 | 4.9 | 5 | 5 | 1.5 |
|  | 5.0 | 4.5 | 4.8 | 5 | 5 | 1.2 |

(1) Detrimental Effects by Agent
(2) *Echinochloa crus-galli*
(3) *Digitalia ciliaris*
(4) *Amaranthus viridis*
(5) *Chenopodium album*
(6) Corn

TABLE 29

Effects by Soil Treatment in Field

| Compound No. | Amount Applied (g/a) | Herbicidal Effects (2) | (3) | (4) | (5) | (1) (6) |
|---|---|---|---|---|---|---|
| 49 | 10.0 | 4.5 | 4.5 | 5 | 5 | 1 |
|  | 5.0 | 3.8 | 4 | 5 | 5 | 1 |
| 50 | 10.0 | 4.8 | 4.8 | 5 | 5 | 1 |
|  | 5.0 | 4.5 | 3.8 | 5 | 4.9 | 1 |
| 52 | 10.0 | 4.2 | 4.8 | 5 | 5 | 1.5 |
|  | 5.0 | 3.8 | 4.8 | 5 | 5 | 1.2 |
| 53 | 20.0 | 3.5 | 2.5 | 5 | 4.9 | 1 |
| 54 | 10.0 | 3.2 | 4.7 | 4.8 | 5 | 1.2 |
|  | 5.0 | 2.5 | 3.2 | 4.8 | 4.9 | 1 |
| 55 | 10.0 | 3.2 | 4.5 | 5 | 4.8 | 1 |
|  | 5.0 | 2.7 | 4 | 4.5 | 4.8 | 1 |

(1) Detrimental Effects by Agent
(2) *Echinochloa crus-galli*
(3) *Digitalia ciliaris*
(4) *Amaranthus viridis*

TABLE 29-continued

Effects by Soil Treatment in Field

| Compound No. | Amount Applied (g/a) | Herbicidal Effects (2) | (3) | (4) | (5) | (1) (6) |
|---|---|---|---|---|---|---|

(5) *Chenopodium album*
(6) Corn

TABLE 30

Effects by Soil Treatment in Field

| Compound No. | Amount Applied (g/a) | Herbicidal Effects (2) | (3) | (4) | (5) | (1) (6) |
|---|---|---|---|---|---|---|
| 57 | 10.0 | 4 | 4.9 | 5 | 5 | 1.5 |
|  | 5.0 | 3 | 4.8 | 5 | 5 | 1.2 |
| 68 | 10.0 | 4.9 | 4.8 | 5 | 5 | 1.3 |
|  | 5.0 | 4.2 | 4.6 | 5 | 5 | 1.1 |
| 72 | 10.0 | 2 | 2 | 4.5 | 3.5 | 1.1 |
| 73 | 10.0 | 3.8 | 2.5 | 5 | 5 | 1.5 |
|  | 5.0 | 3.5 | 2 | 4.8 | 5 | 1.1 |
| B | 10.0 | 2.5 | 2.5 | 3 | 4 | 1.2 |
|  | 5.0 | 2 | 2 | 3 | 3 | 1.2 |

(1) Detrimental Effects by Agent
(2) *Echinochloa crus-galli*
(3) *Digitalia ciliaris*
(4) *Amaranthus viridis*
(5) *Chenopodium album*
(6) Corn

TEST EXAMPLE 3

Effects by Stem-Foliar Treatment

A field soil was packed in a vat having an surface area of 10×10 cm², and a depth of 5 cm, and seeds of *Echinochloa crus-galli, Digitalia ciliaris, Amaranthus viridis, Chenopodium album* and corn were seeded. After 15 days, the wettable powder or the emulsion of the compound of the present invention prepared according to the preparation example was diluted, adjusted to a predetermined concentration, and the stem-foliar portion of the grown plant was spray treated at a liquid amount of 20 liters per are. On the 10th day after the treatment, the herbicidal effects on the tested weeds and the detrimental effects by the agent on the corn were investigated in the same manner as in Test Example 1. The results obtained are shown in Tables 31 to 42.

TABLE 31

Effects by Stem-Foliar Treatment

| Compound No. | Amount Applied ppm | Herbicidal Effects (1) | (2) | (3) | (4) |
|---|---|---|---|---|---|
| 1 | 1000 | 5 | 5 | 5 | 5 |
|  | 200 | 5 | 4.9 | 5 | 5 |
|  | 50 | 3 | 3.5 | 4.8 | 5 |
| 2 | 1000 | 4.9 | 5 | 5 | 5 |
|  | 200 | 3 | 4 | 5 | 5 |
|  | 50 | 2.5 | 3 | 4.8 | 5 |

(1) *Echinochloa crus-galli*
(2) *Digitalia ciliaris*

TABLE 31-continued

Effects by Stem-Foliar Treatment

| Compound No. | Amount Applied ppm | Herbicidal Effects (1) | (2) | (3) | (4) |
|---|---|---|---|---|---|

(3) *Amaranthus viridis*
(4) *Chenopodium album*

TABLE 32

Effects by Stem-Foliar Treatment

| Compound No. | Amount Applied ppm | Herbicidal Effects (1) | (2) | (3) | (4) |
|---|---|---|---|---|---|
| 3 | 1000 | 5 | 5 | 5 | 5 |
|  | 200 | 4.8 | 4.8 | 5 | 5 |
|  | 50 | 3.5 | 4.5 | 5 | 5 |
| 4 | 500 | 5 | 5 | 5 | 5 |
|  | 100 | 3.5 | 4.8 | 5 | 5 |
| 6 | 500 | 4 | 4.9 | 5 | 5 |
|  | 100 | 3 | 3 | 4.9 | 5 |
| 7 | 500 | 5 | 5 | 5 | 5 |
|  | 100 | 4 | 4.5 | 5 | 5 |
| 8 | 500 | 5 | 5 | 5 | 5 |
|  | 100 | 3 | 4.5 | 4.9 | 5 |

(1) *Echinochloa crus-galli*
(2) *Digitalia ciliaris*
(3) *Amaranthus viridis*
(4) *Chenopodium album*

TABLE 33

Effects by Stem-Foliar Treatment

| Compound No. | Amount Applied ppm | Herbicidal Effects (1) | (2) | (3) | (4) |
|---|---|---|---|---|---|
| 9 | 500 | 5 | 5 | 5 | 5 |
|  | 100 | 4.8 | 5 | 5 | 5 |
| 11 | 200 | 5 | 4.9 | 5 | 5 |
|  | 50 | 4.8 | 4.9 | 5 | 5 |
| 12 | 1000 | 5 | 4.9 | 5 | 5 |
|  | 200 | 3 | 3 | 5 | 5 |
| 13 | 500 | 3 | 3 | 4 | 4 |
|  | 100 | 1.8 | 2 | 2 | 2 |
| 14 | 500 | 4.8 | 4.8 | 5 | 5 |
|  | 100 | 3 | 3 | 4.5 | 5 |

(1) *Echinochloa crus-galli*
(2) *Digitalia ciliaris*
(3) *Amaranthus viridis*
(4) *Chenopodium album*

TABLE 34

Effects by Stem-Foliar Treatment

| Compound No. | Amount Applied ppm | Herbicidal Effects (1) | (2) | (3) | (4) |
|---|---|---|---|---|---|
| 15 | 1000 | 4 | 4.8 | 5 | 5 |
|  | 200 | 2 | 4 | 3.5 | 5 |
| 16 | 500 | 5 | 5 | 5 | 5 |
|  | 100 | 4.7 | 4.8 | 5 | 5 |
| 17 | 500 | 5 | 5 | 5 | 5 |
|  | 100 | 5 | 4.6 | 5 | 5 |
| 18 | 500 | 4.9 | 4.9 | 5 | 5 |

TABLE 34-continued

Effects by Stem-Foliar Treatment

| Compound No. | Amount Applied ppm | Herbicidal Effects | | | |
|---|---|---|---|---|---|
| | | (1) | (2) | (3) | (4) |
| 19 | 100 | 3.5 | 3 | 5 | 5 |
| | 200 | 5 | 5 | 5 | 5 |
| | 50 | 5 | 5 | 5 | 5 |

(1) *Echinochloa crus-galli*
(2) *Digitalia ciliaris*
(3) *Amaranthus viridis*
(4) *Chenopodium album*

TABLE 35

Effects by Stem-Foliar Treatment

| Compound No. | Amount Applied ppm | Herbicidal Effects | | | |
|---|---|---|---|---|---|
| | | (1) | (2) | (3) | (4) |
| 20 | 1000 | 5 | 5 | 5 | 5 |
| | 200 | 3 | 3 | 4.9 | 5 |
| | 50 | 1.5 | 2 | 4.8 | 4.9 |
| 21 | 1000 | 5 | 5 | 5 | 5 |
| | 200 | 3.2 | 3.5 | 5 | 5 |
| | 50 | 1.8 | 2 | 4 | 4.8 |
| 22 | 1000 | 4 | 4.9 | 5 | 5 |
| | 200 | 2.3 | 3 | 5 | 5 |
| 23 | 1000 | 3 | 4 | 5 | 5 |
| | 200 | 2 | 2.5 | 5 | 5 |
| 26 | 500 | 2.5 | 4 | 4.9 | 5 |
| | 100 | 1.5 | 2.8 | 2.8 | 4.5 |

(1) *Echinochloa crus-galli*
(2) *Digitalia ciliaris*
(3) *Amaranthus viridis*
(4) *Chenopodium album*

TABLE 36

Effects by Stem-Foliar Treatment

| Compound No. | Amount Applied ppm | Herbicidal Effects | | | |
|---|---|---|---|---|---|
| | | (1) | (2) | (3) | (4) |
| 27 | 500 | 4 | 4.8 | 5 | 5 |
| 28 | 500 | 2.5 | 3.5 | 4 | 5 |
| 31 | 500 | 3.8 | 4.7 | 5 | 5 |
| | 100 | 2.5 | 3 | 4 | 5 |
| 33 | 500 | 4 | 4.9 | 5 | 5 |
| | 100 | 2 | 3.5 | 4 | 5 |
| 34 | 500 | 4.5 | 4.5 | 5 | 5 |
| | 100 | 3 | 3 | 3.5 | 3.5 |
| 35 | 500 | 3 | 3.8 | 5 | 5 |
| | 100 | 2 | 2 | 4.5 | 4.2 |

(1) *Echinochloa crus-galli*
(2) *Digitalia ciliaris*
(3) *Amaranthus viridis*
(4) *Chenopodium album*

TABLE 37

Effects by Stem-Foliar Treatment

| Compound No. | Amount Applied ppm | Herbicidal Effects | | | |
|---|---|---|---|---|---|
| | | (1) | (2) | (3) | (4) |
| 36 | 100 | 5 | 4.9 | 5 | 5 |
| | 25 | 4.9 | 4.9 | 5 | 5 |
| 37 | 500 | 4 | 4.9 | 5 | 5 |
| | 100 | 3.2 | 4.5 | 4.9 | 5 |
| 38 | 500 | 3.8 | 4.3 | 4.9 | 5 |
| | 100 | 3.5 | 4.3 | 4.5 | 5 |
| 39 | 500 | 2.5 | 3.5 | 4.5 | 5 |
| 40 | 100 | 2.2 | 3.2 | 4.7 | 4.8 |
| 41 | 500 | 2 | 4 | 5 | 5 |
| 42 | 500 | 2 | 3 | 5 | 5 |

(1) *Echinochloa crus-galli*
(2) *Digitalia ciliaris*
(3) *Amaranthus viridis*
(4) *Chenopodium album*

TABLE 38

Effects by Stem-Foliar Treatment

| Compound No. | Amount Applied ppm | Herbicidal Effects | | | |
|---|---|---|---|---|---|
| | | (1) | (2) | (3) | (4) |
| 44 | 1000 | 4.6 | 5 | 5 | 5 |
| | 200 | 4 | 4.8 | 5 | 5 |
| | 50 | 3.2 | 4.8 | 5 | 5 |
| 45 | 100 | 5 | 5 | 5 | 5 |
| | 25 | 4.8 | 4.8 | 5 | 5 |
| 46 | 100 | 5 | 5 | 5 | 5 |
| | 25 | 4.8 | 4.9 | 5 | 5 |
| 47 | 500 | 5 | 5 | 5 | 5 |
| | 100 | 4.3 | 4.5 | 5 | 5 |
| 48 | 500 | 5 | 5 | 5 | 5 |
| | 100 | 4.9 | 5 | 5 | 5 |

(1) *Echinochloa crus-galli*
(2) *Digitalia ciliaris*
(3) *Amaranthus viridis*
(4) *Chenopodium album*

TABLE 39

Effects by Stem-Foliar Treatment

| Compound No. | Amount Applied ppm | Herbicidal Effects | | | |
|---|---|---|---|---|---|
| | | (1) | (2) | (3) | (4) |
| 49 | 500 | 5 | 5 | 5 | 5 |
| | 100 | 5 | 5 | 5 | 5 |
| 50 | 100 | 5 | 5 | 5 | 5 |
| | 25 | 4.9 | 4.9 | 5 | 5 |
| 51 | 500 | 5 | 4.9 | 5 | 5 |
| | 100 | 4.5 | 3.7 | 5 | 5 |
| 52 | 100 | 5 | 5 | 5 | 5 |
| | 25 | 4.8 | 4.7 | 5 | 5 |
| 53 | 1000 | 4.7 | 5 | 5 | 5 |
| | 200 | 4.7 | 5 | 5 | 5 |

(1) *Echinochloa crus-galli*
(2) *Digitalia ciliaris*
(3) *Amaranthus viridis*
(4) *Chenopodium album*

TABLE 40

Effects by Stem-Foliar Treatment

| Compound No. | Amount Applied ppm | Herbicidal Effects | | | |
|---|---|---|---|---|---|
| | | (1) | (2) | (3) | (4) |
| 54 | 100 | 4.9 | 4.9 | 5 | 5 |
| | 25 | 4 | 4 | 4.9 | 5 |
| 55 | 500 | 4.8 | 4.9 | 5 | 5 |
| | 100 | 4.5 | 4.5 | 5 | 5 |
| 57 | 500 | 5 | 5 | 5 | 5 |
| | 100 | 4.8 | 4.9 | 5 | 5 |
| 58 | 500 | 4.8 | 4.9 | 5 | 5 |
| | 100 | 3 | 3.5 | 4.8 | 5 |
| 59 | 500 | 4 | 4 | 5 | 5 |
| 64 | 500 | 2 | 3 | 5 | 5 |

(1) *Echinochloa crus-galli*
(2) *Digitalia ciliaris*
(3) *Amaranthus viridis*
(4) *Chenopodium album*

TABLE 41

Effects by Stem-Foliar Treatment

| Compound No. | Amount Applied ppm | Herbicidal Effects | | | |
|---|---|---|---|---|---|
| | | (1) | (2) | (3) | (4) |
| 65 | 500 | 4.5 | 4.9 | 5 | 5 |
| | 100 | 3 | 3.5 | 5 | 5 |
| 67 | 500 | 4.9 | 5 | 5 | 5 |
| | 100 | 3.8 | 4.8 | 5 | 5 |
| 68 | 100 | 5 | 5 | 5 | 5 |
| | 25 | 4.3 | 4.3 | 4.9 | 5 |
| 69 | 500 | 4.9 | 5 | 5 | 5 |
| | 100 | 3.5 | 4.5 | 5 | 5 |
| 70 | 500 | 4.8 | 5 | 5 | 5 |
| | 100 | 4.5 | 4.8 | 4.9 | 5 |

(1) *Echinochloa crus-galli*
(2) *Digitalia ciliaris*
(3) *Amaranthus viridis*
(4) *Chenopodium album*

TABLE 42

Effects by Stem-Foliar Treatment

| Compound No. | Amount Applied ppm | Herbicidal Effects | | | |
|---|---|---|---|---|---|
| | | (1) | (2) | (3) | (4) |
| 71 | 500 | 4.7 | 5 | 5 | 5 |
| | 100 | 3.5 | 4 | 5 | 5 |
| 72 | 500 | 4.9 | 4.8 | 5 | 5 |
| | 100 | 3.5 | 3 | 5 | 5 |
| 73 | 100 | 5 | 5 | 5 | 5 |
| | 25 | 4.9 | 4.9 | 5 | 5 |

(1) *Echinochloa crus-galli*
(2) *Digitalia ciliaris*
(3) *Amaranthus viridis*
(4) *Chenopodium album*

Further, the herbicidal effects of the compounds of the present invention represented by the general formulae (V') and (V") were investigated according to the methods shown in the following Test Examples 4 to 6 using the preparations prepared according to the procedures illustrated in Preparation Examples 1 to 3. The herbicidal effects on the test plants and the detrimental effects by the agent on the test crops were determined according to the criterions described below (Table 43).

TABLE 43

Rating Criteria

| (1): (2) | (3): (4) |
|---|---|
| 0: 81–100 | –: No Detrimental Effect |
| 1: 61–80 | +: Very Slight Detrimental Effect |
| 2: 41–60 | ++: Slight Detrimental Effect |
| 3: 21–40 | +++: Medium Detrimental Effect |
| 4: 6–20 | ++++: Severe Detrimental Effect |
| 5: 0–5 | x: Withering |

(1) Degree of Herbirical Effect
(2) Proportion of Residual Amount (%)
(3) Detrimental Effects by Agent
(4) Proportion of Growth Amount As control compounds, the compounds shown in Table 44 were used, and the herbicidal activity and the detrimental effects by the agent on the crops thereof were investigated based on the criterions shown in Table 43 using the same preparation procedure and the treatment method as those in the compounds of the present invention, and the results obtained are shown in Tables 45 to 49.

TABLE 44

| | Comparative Control Agent | |
|---|---|---|
| Symbol of Compound | Chemical Structure Formula | Remarks |
| C | [structure: 2,4-dichloro-5-isopropoxyphenyl oxadiazolone] | Ronstar |
| D | [structure: 4-chlorophenyl-N=C tetrahydrophthalimide-like] | Compound disclosed in Specification of Japanese Patent Publication (KOKAI) No. 53-23962 |
| E | [structure: 4-chloro-2-fluoro-5-methoxyphenyl derivative] | Compound disclosed in Specification of Japanese Patent Publication (KOKAI) No. 59-70682 |
| F | [structure: 4-chloro-2-fluoro-5-propargyloxyphenyl derivative] | Compound disclosed in Specification of Japanese Patent Publication (KOKAI) No. 59-70682 |

TEST EXAMPLE 4

Effects on Paddy Field Weeds

Soil of a paddy field was filled in a pot of 1/5000 are, and seeds of *Echinochloa oryzicola, Monochoria vaginalis, Scirpus juncoides, Eleocharis acicularis* and other annual broad leaf weeds, and rice seedlings at a 2 to 3-leaf stage (Species: Koshihikari) were seeded or transplanted, and the pot was maintained under the submerged condition. After one day, the wettable powder or the emulsion of the compound of the present invention prepared according to the preparation example was diluted, and the pot was treated dropwise at a predetermined dose per are. On the 15th day after the treatment, the herbicidal effect on the test plants and the detrimental effect by the agent on the rice plant were investigated on the rating criterions shown in Table 43, and the results shown in Tables 45 and 46 were obtained.

TABLE 45

| | | Effects by Pretreatment of Soil in Paddy Field Soil | | | | | |
|---|---|---|---|---|---|---|---|
| Compound No. | Amount Applied g/a | Herbicidal Effects | | | | | (1) |
| | | (2) | (3) | (4) | (5) | (6) | (7) |
| 10 | 2.0 | 5 | 5 | 5 | 5 | 5 | — |
| | 1.0 | 5 | 5 | 5 | 3 | 3 | — |
| | 0.5 | 4 | 5 | 5 | 0 | 1 | — |
| 12 | 2.0 | 5 | 5 | 5 | 3 | 5 | ++ |
| | 1.0 | 5 | 5 | 5 | 3 | 5 | —+ |
| | 0.5 | 4 | 5 | 5 | 3 | 4 | — |
| 13 | 2.0 | 5 | 5 | 5 | 3 | 5 | + |
| | 1.0 | 5 | 5 | 5 | 3 | 5 | —+ |
| | 0.5 | 4 | 5 | 5 | 3 | 5 | — |
| 42 | 2.0 | 5 | 5 | 5 | 5 | 5 | —+ |
| | 1.0 | 5 | 5 | 5 | 5 | 5 | —+ |
| | 0.5 | 4 | 5 | 5 | 5 | 5 | —+ |
| 44 | 2.0 | 5 | 5 | 5 | 5 | 5 | + |
| | 1.0 | 5 | 5 | 5 | 5 | 5 | + |
| | 0.5 | 4 | 5 | 5 | 5 | 5 | —+ |

(1) Detrimental Effects by Agent
(2) *Echinochloa oryzicola*
(3) *Monochoria vaginalis*
(4) Other Annual Broad Leaf Weeds

TABLE 45-continued

Effects by Pretreatment of Soil in Paddy Field Soil

| Compound No. | Amount Applied g/a | Herbicidal Effects (2) | (3) | (4) | (5) | (6) | (1) (7) |
|---|---|---|---|---|---|---|---|

(5) *Eleocharis sicularis*
(6) *Scirpus juncoides*
(7) Rice Plant

TABLE 46

Effects by Pretreatment of Soil in Paddy Field Soil

| Compound No. | Amount Applied g/a | Herbicidal Effects (2) | (3) | (4) | (5) | (6) | (1) (7) |
|---|---|---|---|---|---|---|---|
| 45 | 2.0 | 5 | 5 | 5 | 5 | 5 | + |
|    | 1.0 | 5 | 5 | 5 | 5 | 5 | —+ |
|    | 0.5 | 5 | 5 | 5 | 5 | 5 | —+ |
| C  | 2.0 | 5 | 5 | 5 | 5 | 5 | —+ |
|    | 1.0 | 5 | 5 | 5 | 5 | 5 | — |
|    | 0.5 | 5 | 5 | 5 | 4 | 4 | — |
| D  | 2.0 | 5 | 5 | 5 | 5 | 5 | + |
|    | 1.0 | 3 | 5 | 5 | 5 | 4 | —+ |
|    | 0.5 | 2 | 5 | 5 | 5 | 4 | — |
| E  | 2.0 | 5 | 5 | 5 | 5 | 5 | ++ |
|    | 1.0 | 5 | 5 | 5 | 5 | 5 | + |
|    | 0.5 | 4 | 5 | 5 | 5 | 5 | —+ |
| F  | 2.0 | 5 | 5 | 5 | 5 | 5 | + |
|    | 1.0 | 5 | 5 | 5 | 5 | 5 | —+ |
|    | 0.5 | 5 | 5 | 5 | 5 | 5 | — |

(1) Detrimental Effects by Agent
(2) *Echinochloa oryzicola*
(3) *Monochoria vaginalis*
(4) Other Annual Broad Leaf Weeds
(5) *Eleocharis sicularis*
(6) *Scirpus juncoides*
(7) Rice Plant

TEST EXAMPLE 5

Effects by Field Soil Treatment

Field soil was filled in a vat having an area of 10×10 cm² and a depth of 5 cm, and seeds of *Echinochloa crus-galli, Digitalia ciliaris, Amaranthus viridis, Chenopodium album* and corn were seeded, and a covering soil of 0.5 cm was put on the seeds. Next day, the wettable powder or the emulsion of the compound of the present invention prepared according to the preparation example was diluted and applied over the covering soil at a predetermined dose per are. On the 15th day after treatment, the herbicidal effects on the test weeds and the detrimental effects by the agent on the corn were investigated on the rating criterions shown in Table 43, and the results shown in Table 47 were obtained.

TABLE 47

Effects in Field Soil Treatment

| Compound No. | Amount Applied g/a | Herbicidal Effects (1) | (2) | (3) | (4) | Detrimental Effects by Agents Corn |
|---|---|---|---|---|---|---|
| 10 | 10.0 | 0 | 1 | 5 | 3 | — |
|    | 5.0  | 0 | 0 | 3 | 1 | — |
| 12 | 10.0 | 0 | 0 | 1 | 0 | — |
|    | 5.0  | 0 | 0 | 0 | 0 | — |
| 13 | 10.0 | 1 | 0 | 1 | 1 | — |
|    | 5.0  | 0 | 0 | 0 | 0 | — |
| 42 | 10.0 | 3 | 5 | 5 | 5 | —+ |
|    | 5.0  | 2 | 3 | 5 | 5 | — |
| 44 | 10.0 | 1 | 1 | 5 | 0 | — |
|    | 5.0  | 1 | 0 | 4 | 0 | — |
| 45 | 20.0 | 3 | 2 | 5 | 5 | — |
|    | 10.0 | 2 | 1 | 5 | 3 | — |
| C  | 10.0 | 3 | 5 | 5 | 5 | +++ |
|    | 5.0  | 1 | 4 | 5 | 5 | —+ |
| D  | 10.0 | 0 | 1 | 0 | 1 | — |
|    | 5.0  | 0 | 0 | 0 | 0 | — |
| E  | 10.0 | 5 | 5 | 5 | 5 | — |
|    | 5.0  | 3 | 2 | 5 | 5 | — |
| F  | 10.0 | 5 | 4 | 5 | 5 | + |
|    | 5.0  | 4 | 2 | 5 | 5 | —+ |

(1) *Echinochloa crus-galli*
(2) *Digitalia ciliaris*
(3) *Amaranthus viridis*
(4) *Chenopodium album*

TEST EXAMPLE 6

Effects by Stem-Foliar Treatment

A field soil was packed in a vat having an surface area of 10×10 cm², and a depth of 5 cm, and seeds of *Echonochloa crus-galli, Digitalia ciliaris, Amaranthus viridis, Chenopodium album* and corn were seeded. After 15 days, the wettable powder or the emulsion of the compound of the present invention prepared according to the preparation example was diluted, adjusted to a predetermined concentration, and the stem-foliar portion of the grown plant was spray treated at a liquid amount of 20 liters per are. On the 10th day after the treatment, the herbicidal effects on the tested weeds and the detrimental effects by the agent on the corn were investigated on the rating criterions shown in Table 43, and the results shown in Tables 48 and 49 were obtained.

TABLE 48

Effects by Stem-Foliar Treatment

| Compound No. | Amount Applied ppm | Herbicidal Effects (1) | (2) | (3) | (4) | Detrimental Effects by Agents Corn |
|---|---|---|---|---|---|---|
| 91  | 500 | 5 | 5 | 5 | 5 | x |
|     | 100 | 3 | 3 | 5 | 5 | +++ |
|     | 25  | 1 | 2 | 5 | 5 | + |
| 93  | 500 | 4 | 5 | 5 | 5 | x |
|     | 100 | 2 | 3 | 5 | 5 | x |
|     | 25  | 1 | 1 | 3 | 5 | ++++ |
| 94  | 500 | 5 | 5 | 5 | 5 | x |
|     | 100 | 1 | 3 | 5 | 5 | x |
|     | 25  | 1 | 1 | 2 | 5 | ++++ |
| 129 | 500 | 5 | 5 | 5 | 5 | x |
|     | 100 | 5 | 5 | 5 | 5 | x |
|     | 25  | 3 | 1 | 5 | 5 | ++ |
| 131 | 500 | 5 | 5 | 5 | 5 | x |
|     | 100 | 5 | 4 | 5 | 5 | ++++ |

TABLE 48-continued

| Compound No. | Amount Applied ppm | Herbicidal Effects (1) | (2) | (3) | (4) | Detrimental Effects by Agents Corn |
|---|---|---|---|---|---|---|
| | 25 | 4 | 4 | 5 | 5 | +++ |

(1) *Echinochloa crus-galli*
(2) *Digitalia ciliaris*
(3) *Amaranthus viridis*
(4) *Chenopodium album*

TABLE 49

| Compound No. | Amount Applied ppm | Herbicidal Effects (1) | (2) | (3) | (4) | Detrimental Effects by Agents Corn |
|---|---|---|---|---|---|---|
| 132 | 500 | 5 | 5 | 5 | 5 | x |
| | 100 | 5 | 5 | 5 | 5 | x |
| | 25 | 4 | 4 | 5 | 5 | ++++ |
| C | 500 | 5 | 5 | 5 | 5 | x |
| | 100 | 5 | 5 | 5 | 5 | x |
| | 25 | 2 | 4 | 4 | 5 | ++ |
| D | 1000 | 5 | 5 | 5 | 5 | x |
| | 500 | 5 | 5 | 5 | 5 | x |
| | 100 | 2 | 3 | 3 | 3 | ++++ |
| E | 500 | 5 | 5 | 5 | 5 | x |
| | 100 | 5 | 5 | 5 | 5 | x |
| | 25 | 5 | 5 | 5 | 5 | ++++ |
| F | 500 | 5 | 5 | 5 | 5 | ++++ |
| | 100 | 5 | 5 | 5 | 5 | ++++ |
| | 25 | 4 | 4 | 5 | 5 | + |

(1) *Echinochloa crus-galli*
(2) *Digitalia ciliaris*
(3) *Amaranthus viridis*
(4) *Chenopodium album*

We claim:

1. A compound represented by the general formula (V):

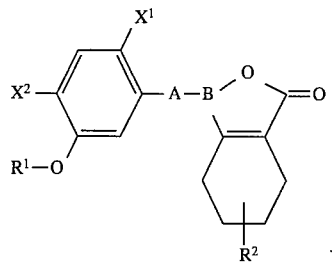

(V)

wherein $X^1$ represents a halogen atom, $X^2$ represents a hydrogen atom or a halogen atom, $R^1$ represents a substituted or unsubstituted cycloakyl group having from 3 to 8 carbon atoms, A—B represents NH—C(OH) or N═C, and $R^2$ represents a hydrogen atom, a chlorine atom or a methyl group.

2. A compound as claimed in claim 1, wherein $X^1$ represents a fluorine atom, $X^2$ represents a chlorine atom, and $R^1$ represents a cyclopentyl group.

3. A herbicide containing, as an active ingredient, a compound represented by the general formula (V):

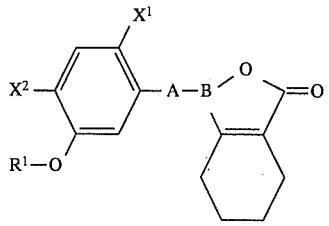

(V)

wherein $X^1$ represents a halogen atom, $X^2$ represents a hydrogen atom or a halogen atom, $R^1$ represents a substituted or unsubstituted cycloakyl group having from 3 to 8 carbon atoms, A—B represents NH—C(OH) or N═C, and $R^2$ represents a hydrogen atom, a chlorine atom or a methyl group.

4. A herbicide containing, as an active ingredient, a compound as claimed in claim 3, wherein $X^1$ is a fluorine atom, $X^2$ is a chlorine atom, and $R^1$ is a cyclopentyl group.

* * * * *